United States Patent
Kohm et al.

(10) Patent No.: US 7,998,208 B2
(45) Date of Patent: Aug. 16, 2011

(54) PERCUTANEOUS SPINAL IMPLANTS AND METHODS

(75) Inventors: Andrew C. Kohm, Burlingame, CA (US); Hugues F. Malandain, Mountain View, CA (US)

(73) Assignee: Kyphon Sarl, Neuchatel (CH)

( * ) Notice: Subject to any disclaimer, the term of this patent is extended or adjusted under 35 U.S.C. 154(b) by 1174 days.

(21) Appl. No.: 11/693,502

(22) Filed: Mar. 29, 2007

(65) Prior Publication Data

US 2008/0027433 A1 Jan. 31, 2008

Related U.S. Application Data

(63) Continuation-in-part of application No. 11/454,153, filed on Jun. 16, 2006, which is a continuation-in-part of application No. PCT/US2006/005580, filed on Feb. 17, 2006, which is a continuation-in-part of application No. 11/059,526, filed on Feb. 17, 2005, now abandoned, which is a continuation-in-part of application No. 11/252,879, filed on Oct. 19, 2005, which is a continuation-in-part of application No. 11/252,880, filed on Oct. 19, 2005, now abandoned.

(60) Provisional application No. 60/695,836, filed on Jul. 1, 2005.

(51) Int. Cl.
*A61F 2/44* (2006.01)

(52) U.S. Cl. .................. 623/17.11; 606/279; 606/86 A

(58) Field of Classification Search ................. 606/279, 606/86 A, 99, 159, 167, 170; 623/17.11–17.16, 623/1.11, 1.12, 1.18, 1.23

See application file for complete search history.

(56) References Cited

U.S. PATENT DOCUMENTS

| | | |
|---|---|---|
| 2,677,369 A | 5/1954 | Knowles |
| 3,486,505 A | 12/1969 | Morrison |
| 3,648,691 A | 3/1972 | Lumb et al. |
| 4,011,602 A | 3/1977 | Rybicki et al. |
| 4,257,409 A | 3/1981 | Bacal et al. |
| 4,554,914 A | 11/1985 | Kapp et al. |
| 4,573,454 A | 3/1986 | Hoffman |
| 4,604,995 A | 8/1986 | Stephens et al. |
| 4,686,970 A | 8/1987 | Dove et al. |
| 4,827,918 A | 5/1989 | Olerud |
| 4,997,432 A | 3/1991 | Keller |
| 5,011,484 A | 4/1991 | Breard |
| 5,047,055 A | 9/1991 | Bao et al. |
| 5,092,866 A | 3/1992 | Breard et al. |
| 5,201,734 A | 4/1993 | Cozad et al. |
| 5,306,275 A | 4/1994 | Bryan |

(Continued)

FOREIGN PATENT DOCUMENTS

DE 2821678 A1 11/1979

(Continued)

OTHER PUBLICATIONS

Benzel et al., "Posterior Cervical Interspinous Compression Wiring and Fusion for Mid to Low Cervical Spinal Injuries," J. Neurosurg., Jun. 1989, pp. 893-899, vol. 70.

(Continued)

*Primary Examiner* — Eduardo C Robert
*Assistant Examiner* — Tara R Carter

(57) ABSTRACT

An apparatus includes an elongate member including a cutting edge disposed at a distal end portion of the elongate member. The cutting edge is configured to cut a portion of an implant when the elongate member moves relative to the implant.

12 Claims, 43 Drawing Sheets

U.S. PATENT DOCUMENTS

| | | | |
|---|---|---|---|
| 5,356,423 A * | 10/1994 | Tihon et al. | 623/1.15 |
| 5,360,430 A | 11/1994 | Lin | |
| 5,366,455 A | 11/1994 | Dove | |
| 5,415,661 A | 5/1995 | Holmes | |
| 5,437,672 A | 8/1995 | Alleyne | |
| 5,454,812 A | 10/1995 | Lin | |
| 5,456,689 A * | 10/1995 | Kresch et al. | 606/180 |
| 5,496,318 A | 3/1996 | Howland et al. | |
| 5,545,170 A | 8/1996 | Hart | |
| 5,599,279 A | 2/1997 | Slotman et al. | |
| 5,609,634 A | 3/1997 | Voydeville | |
| 5,628,756 A | 5/1997 | Barker, Jr. et al. | |
| 5,645,599 A | 7/1997 | Samani | |
| 5,674,295 A | 10/1997 | Ray et al. | |
| 5,676,702 A | 10/1997 | Ratron | |
| 5,690,649 A | 11/1997 | Li | |
| 5,810,815 A | 9/1998 | Morales | |
| 5,836,948 A | 11/1998 | Zucherman et al. | |
| 5,860,977 A | 1/1999 | Zucherman et al. | |
| 5,976,186 A | 11/1999 | Bao et al. | |
| 6,022,376 A | 2/2000 | Assell et al. | |
| 6,042,582 A | 3/2000 | Ray | |
| 6,048,342 A | 4/2000 | Zucherman et al. | |
| 6,068,630 A | 5/2000 | Zucherman et al. | |
| 6,083,225 A | 7/2000 | Winslow et al. | |
| 6,113,602 A | 9/2000 | Sand | |
| 6,132,464 A | 10/2000 | Martin | |
| 6,159,212 A | 12/2000 | Schoedinger, III et al. | |
| 6,171,339 B1 | 1/2001 | Houfburg et al. | |
| 6,174,311 B1 | 1/2001 | Branch et al. | |
| 6,224,607 B1 | 5/2001 | Michelson | |
| 6,241,729 B1 | 6/2001 | Estes et al. | |
| 6,245,107 B1 * | 6/2001 | Ferree | 606/279 |
| 6,261,296 B1 | 7/2001 | Aebi et al. | |
| 6,261,586 B1 | 7/2001 | McKay | |
| 6,293,949 B1 | 9/2001 | Justis et al. | |
| 6,336,930 B1 * | 1/2002 | Stalcup et al. | 606/284 |
| 6,352,537 B1 | 3/2002 | Strnad | |
| 6,364,883 B1 | 4/2002 | Santilli | |
| 6,402,750 B1 | 6/2002 | Atkinson et al. | |
| 6,440,169 B1 | 8/2002 | Elberg et al. | |
| 6,451,019 B1 | 9/2002 | Zucherman et al. | |
| 6,554,833 B2 | 4/2003 | Levy et al. | |
| 6,565,570 B2 | 5/2003 | Sterett et al. | |
| 6,582,433 B2 | 6/2003 | Yun | |
| 6,626,944 B1 | 9/2003 | Taylor | |
| 6,645,207 B2 | 11/2003 | Dixon et al. | |
| 6,652,533 B2 | 11/2003 | O'Neil | |
| 6,676,665 B2 | 1/2004 | Foley et al. | |
| 6,695,842 B2 | 2/2004 | Zucherman et al. | |
| 6,709,435 B2 | 3/2004 | Lin | |
| 6,723,126 B1 | 4/2004 | Berry | |
| 6,733,534 B2 | 5/2004 | Sherman | |
| 6,752,832 B2 | 6/2004 | Neumann | |
| 6,761,720 B1 | 7/2004 | Senegas | |
| 6,835,205 B2 | 12/2004 | Atkinson et al. | |
| 6,946,000 B2 | 9/2005 | Senegas et al. | |
| 7,041,136 B2 | 5/2006 | Goble et al. | |
| 7,048,736 B2 | 5/2006 | Robinson et al. | |
| 7,087,083 B2 | 8/2006 | Pasquet et al. | |
| 7,163,558 B2 | 1/2007 | Senegas et al. | |
| 7,201,751 B2 | 4/2007 | Zucherman et al. | |
| 7,238,204 B2 | 7/2007 | Le Couedic et al. | |
| 7,306,628 B2 | 12/2007 | Zucherman et al. | |
| 7,442,208 B2 | 10/2008 | Mathieu et al. | |
| 7,445,637 B2 | 11/2008 | Taylor | |
| 2002/0143331 A1 | 10/2002 | Zucherman et al. | |
| 2003/0144737 A1 * | 7/2003 | Sherman | 623/17.12 |
| 2003/0153915 A1 | 8/2003 | Nekozuka et al. | |
| 2004/0010312 A1 * | 1/2004 | Enayati | 623/17.11 |
| 2004/0059318 A1 | 3/2004 | Zhang et al. | |
| 2004/0097931 A1 | 5/2004 | Mitchell | |
| 2004/0106927 A1 | 6/2004 | Ruffner et al. | |
| 2004/0230202 A1 | 11/2004 | Tromanhauser et al. | |
| 2004/0249388 A1 | 12/2004 | Michelson | |
| 2005/0010221 A1 | 1/2005 | Dalton | |
| 2005/0010293 A1 | 1/2005 | Zucherman et al. | |
| 2005/0049708 A1 | 3/2005 | Atkinson et al. | |
| 2005/0090824 A1 | 4/2005 | Shluzas et al. | |
| 2005/0113842 A1 | 5/2005 | Bertagnoli et al. | |
| 2005/0119665 A1 | 6/2005 | Keller | |
| 2005/0165398 A1 | 7/2005 | Reiley | |
| 2005/0203512 A1 | 9/2005 | Hawkins et al. | |
| 2005/0203624 A1 | 9/2005 | Serhan et al. | |
| 2005/0228391 A1 | 10/2005 | Levy et al. | |
| 2005/0261768 A1 | 11/2005 | Trieu | |
| 2005/0288672 A1 | 12/2005 | Ferree | |
| 2006/0004447 A1 | 1/2006 | Mastrorio et al. | |
| 2006/0015181 A1 | 1/2006 | Elberg | |
| 2006/0064165 A1 | 3/2006 | Zucherman et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0089654 A1 | 4/2006 | Lins et al. | |
| 2006/0089719 A1 | 4/2006 | Trieu | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0122620 A1 | 6/2006 | Kim | |
| 2006/0136060 A1 | 6/2006 | Taylor | |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0264938 A1 | 11/2006 | Zucherman et al. | |
| 2006/0271044 A1 | 11/2006 | Petrini et al. | |
| 2006/0293662 A1 | 12/2006 | Boyer, II et al. | |
| 2007/0043361 A1 | 2/2007 | Malandain et al. | |
| 2007/0043363 A1 | 2/2007 | Malandain et al. | |
| 2007/0049935 A1 | 3/2007 | Edidin et al. | |
| 2007/0112354 A1 | 5/2007 | Iwasaki et al. | |

FOREIGN PATENT DOCUMENTS

| | | |
|---|---|---|
| DE | 4217660 A1 | 12/1993 |
| EP | 0322334 B1 | 2/1992 |
| EP | 1138268 A1 | 10/2001 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2816197 A1 | 5/2002 |
| JP | 02-224660 | 9/1990 |
| JP | 09-075381 | 3/1997 |
| SU | 988281 | 1/1983 |
| WO | WO 94/26192 | 11/1994 |
| WO | WO 94/26195 | 11/1994 |
| WO | WO 98/20939 | 5/1998 |
| WO | WO 2004/047691 A1 | 6/2004 |
| WO | WO 2005/009300 A1 | 2/2005 |
| WO | WO 2005/044118 A1 | 5/2005 |
| WO | WO 2005/110258 A1 | 11/2005 |
| WO | WO 2007/034516 A1 | 3/2007 |

OTHER PUBLICATIONS

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Taylor et al., "Analyse d'une experience clinique d'un implant postérieur amortissant," Rachis Revue de Pathologie Vertébrate, Oct./Nov. 1999, vol. 11, No. 4-5, Gieda Inter Rachis.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

* cited by examiner

FIG. B

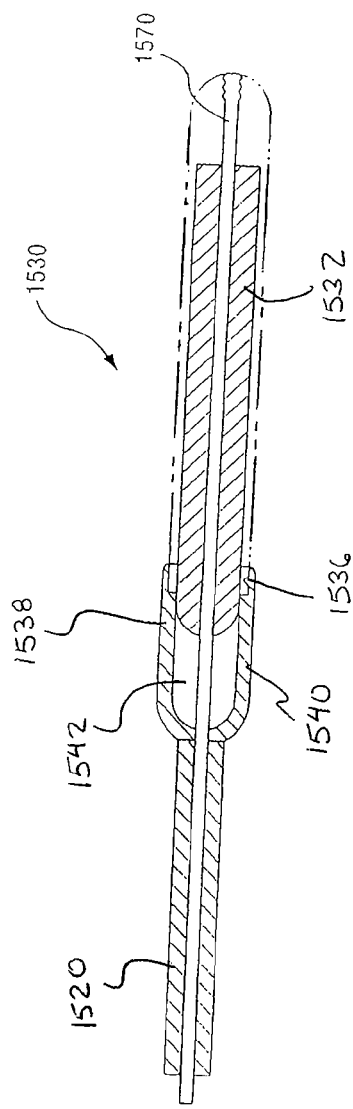
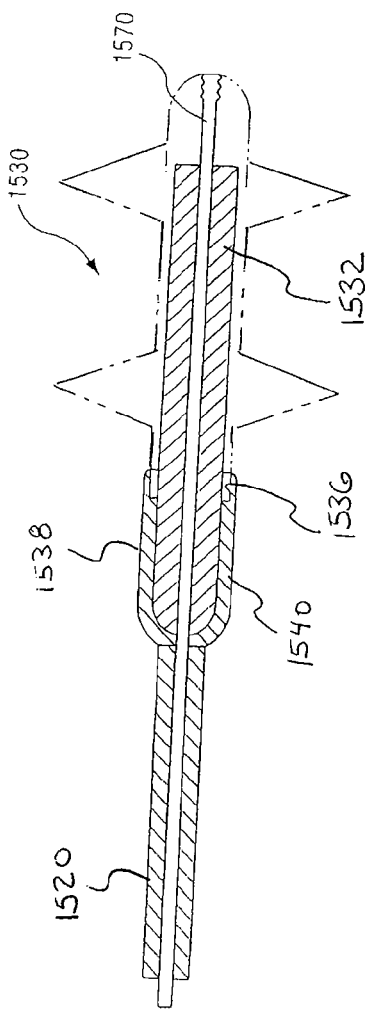

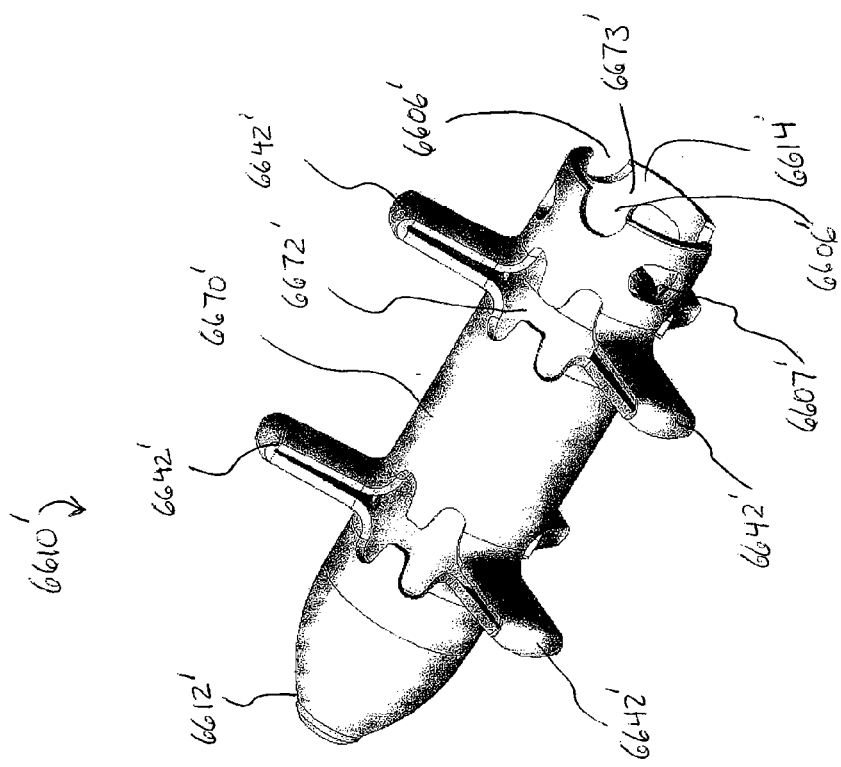
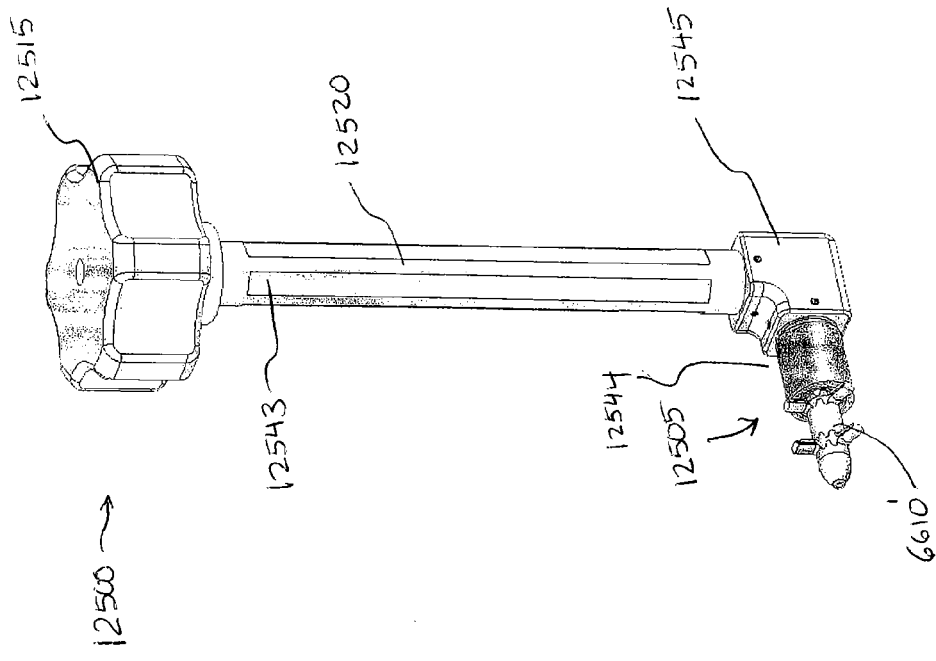

PERCUTANEOUS SPINAL IMPLANTS AND METHODS

CROSS-REFERENCE TO RELATED APPLICATIONS

This application claims priority to and is a continuation-in-part of U.S. patent application Ser. No. 11/454,153, entitled "Apparatus and Method for Treatment of Spinal Conditions," filed Jun. 16, 2006, which is a continuation-in-part of International Patent Application No. PCT/US2006/005580, entitled "Percutaneous Spinal Implants and Methods," filed Feb. 17, 2006, and which is a continuation-in-part of U.S. patent application Ser. No. 11/059,526, entitled "Apparatus and Method for Treatment of Spinal Conditions," filed Feb. 17, 2005 now abandoned, and which is a continuation-in-part of U.S. patent application Ser. No. 11/252,879, entitled "Percutaneous Spinal Implants and Methods," filed Oct. 19, 2005, which claims priority to U.S. Provisional Application Ser. No. 60/695,836, entitled "Percutaneous Spinal Implants and Methods," filed Jul. 1, 2005, and which is a continuation-in-part of U.S. patent application Ser. No. 11/252,880, entitled "Percutaneous Spinal Implants and Methods," filed Oct. 19, 2005 now abandoned, which claims priority to U.S. Provisional Application Ser. No. 60/695,836, entitled "Percutaneous Spinal Implants and Methods," filed Jul. 1, 2005; each of which is incorporated herein by reference in its entirety.

This application is related to U.S. patent application Ser. Nos. 11/693,500 and 11/693,496, each entitled "Percutaneous Spinal Implants and Methods," filed on the same date, each of which is incorporated herein by reference in their entirety.

BACKGROUND

The invention relates generally to the treatment of spinal conditions, and more particularly, to the treatment of spinal compression using percutaneous spinal implants for implantation between adjacent spinous processes.

A back condition that impacts many individuals is spinal stenosis. Spinal stenosis is a progressive narrowing of the spinal canal that causes compression of the spinal cord. Each vertebra in the spinal column has an opening that extends through it. The openings are aligned vertically to form the spinal canal. The spinal cord runs through the spinal canal. As the spinal canal narrows, the spinal cord and nerve roots extending from the spinal cord and between adjacent vertebrae are compressed and may become inflamed. Spinal stenosis can cause pain, weakness, numbness, burning sensations, tingling, and in particularly severe cases, may cause loss of bladder or bowel function, or paralysis. The legs, calves and buttocks are most commonly affected by spinal stenosis, however, the shoulders and arms may also be affected.

Mild cases of spinal stenosis may be treated with rest or restricted activity, non-steroidal anti-inflammatory drugs (e.g., aspirin), corticosteroid injections (epidural steroids), and/or physical therapy. Some patients find that bending forward, sitting or lying down may help relieve the pain. This may be due to bending forward creates more vertebral space, which may temporarily relieve nerve compression. Because spinal stenosis is a progressive disease, the source of pressure may have to be surgically corrected (decompressive laminectomy) as the patient has increasing pain. The surgical procedure can remove bone and other tissues that have impinged upon the spinal canal or put pressure on the spinal cord. Two adjacent vertebrae may also be fused during the surgical procedure to prevent an area of instability, improper alignment or slippage, such as that caused by spondylolisthesis. Surgical decompression can relieve pressure on the spinal cord or spinal nerve by widening the spinal canal to create more space. This procedure requires that the patient be given a general anesthesia as an incision is made in the patient to access the spine to remove the areas that are contributing to the pressure. This procedure, however, may result in blood loss and an increased chance of significant complications, and usually results in an extended hospital stay.

Minimally-invasive procedures have been developed to provide access to the space between adjacent spinous processes such that major surgery is not required. Such known procedures, however, may not be suitable in conditions where the spinous processes are severely compressed. Moreover, such procedures typically involve large or multiple incisions.

Thus, a need exists for improvements in the treatment of spinal conditions such as spinal stenosis.

SUMMARY OF THE INVENTION

Medical devices and related methods for the treatment of spinal conditions are described herein. In some embodiments, an apparatus includes an elongate member including a cutting edge disposed at a distal end portion of the elongate member. The cutting edge is configured to cut a portion of an implant when the elongate member moves relative to the implant.

BRIEF DESCRIPTION OF THE DRAWINGS

FIG. 15 is a cross-sectional view of a portion of the device illustrated in FIG. 11 in a first configuration, taken along line B-B in FIG. 11.

FIG. 16 is a cross-sectional view of a portion of the device illustrated in FIG. 11 in a second configuration, taken along line C-C in FIG. 11.

FIG. 54 is a perspective view of a deployment tool according to an embodiment of the invention.

FIG. 55 is a perspective view of a spinal implant according to an embodiment of the invention.

DETAILED DESCRIPTION

Figure 1:
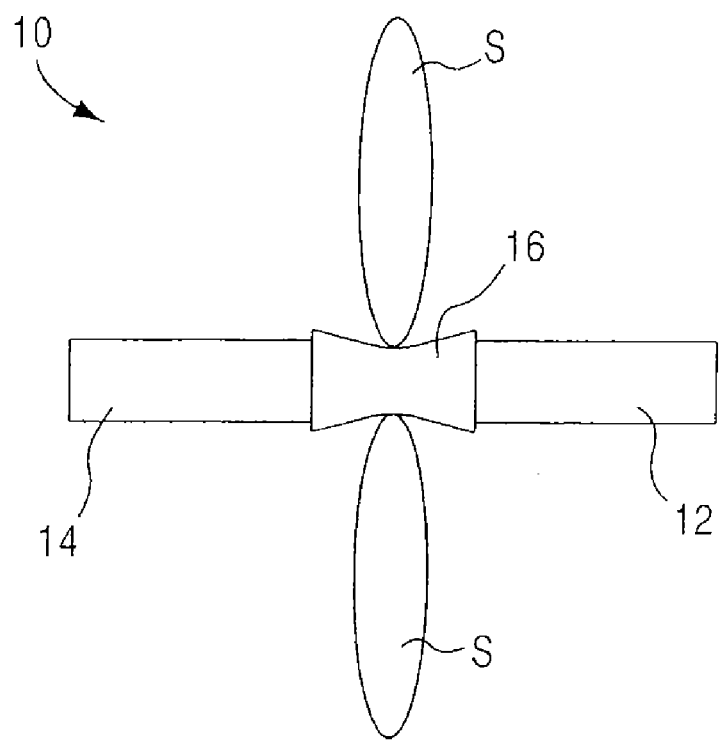
FIG. 1 is a schematic illustration of a posterior view of a medical device according to an embodiment of the invention in a first configuration adjacent two adjacent spinous processes.

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the implant end first inserted inside the patient's body would be the distal end of the implant, while the implant end to last enter the patient's body would be the proximal end of the implant.

In some embodiments, an apparatus includes an elongate member configured to engage a spinal implant and a locking member. The locking member is disposed at a distal end portion of the elongate member. The locking member is configured to move relative to the elongate member between a first position and a second position in a direction substantially perpendicular to a center line of the elongate member. The locking member is configured to allow the distal end portion of the elongate member to move relative to the spinal implant when in the first position. The locking member is configured to couple the distal end portion of the elongate member to the spinal implant when in the second position.

In some embodiments, an apparatus includes an elongate member configured to engage a spinal implant, a sleeve and a locking member. The locking member is disposed at a distal end portion of the elongate member. The locking member is configured to move relative to the elongate member between a first position and a second position in a direction substantially perpendicular to a center line of the elongate member. The locking member is configured to allow the distal end portion of the elongate member to move relative to the spinal implant when in the first position. The locking member is configured complimentarily fit with an opening defined by the spinal implant to couple the distal end portion of the elongate member to the spinal implant when in the second position. The sleeve is disposed about an outer surface of the elongate member and is configured to retain the locking member within the opening when the sleeve is in a first position.

In some embodiments, an apparatus includes a first elongate member configured to engage a spinal implant, a second elongate member movably disposed within the first elongate member, and a locking member. The locking member is disposed at a distal end portion of the elongate member. The locking member is configured to move relative to the first elongate member between a first position and a second position in a direction substantially perpendicular to a center line of the first elongate member. The locking member is configured to allow the distal end portion of the first elongate member to move relative to the spinal implant when in the first position. The locking member is configured to couple the distal end portion of the first elongate member to the spinal implant when in the second position. The second elongate member is configured to move an inner member of the spinal implant relative to a portion of an outer member of the spinal implant when the locking member is in the second position.

In some embodiments, an apparatus includes an elongate member and a locking member. The elongate member has a distal end portion configured to be removably disposed within an interior portion of a spinal implant. The locking member is configured to releasably couple the distal end portion of the elongate member to the spinal implant. The locking member, which can be, for example, a ball, a pin and/or a retaining ring, is configured to be disposed substantially within the interior portion of the spinal implant such that the elongate member moves relative to the spinal implant when the locking member is in a first configuration. The locking member is configured to engage a surface defining the interior portion of the spinal implant such that the elongate member cannot substantially move relative to the spinal implant when the locking member is in a second configuration.

In some embodiments, an apparatus includes an elongate member configured to engage a spinal implant, a locking member and an actuator. The locking member is disposed at a distal end portion of the elongate member and has a first configuration and a second configuration. The locking member is configured to allow the distal end portion of the elongate member to move relative to the spinal implant when in the first configuration. The locking member is configured to couple the distal end portion of the elongate member to the spinal implant when in the second configuration. The actuator is disposed at the distal end portion of the elongate member and is configured to move the locking member from its first configuration to its second configuration when the elongate member engages the spinal implant. The actuator can be any suitable actuator, such as for example, a mechanical actuator (e.g., a spring-loaded actuator), a pneumatic actuator, a hydraulic actuator and/or an electronic actuator.

In some embodiments, an apparatus includes a first elongate member, a second elongate member and a connector. The second elongate member is movably disposed within a distal end portion of the first elongate member. The second elongate member is configured to engage an inner member of a spinal implant disposed within an outer member of the spinal implant. The connector, which is disposed at the distal end portion of the first elongate member, is configured to releasably connect the distal end portion of the first elongate member to the outer member of the spinal implant.

In some embodiments, an apparatus includes an elongate member and a connector disposed at a distal end portion of the elongate member. The connector is configured to rotate relative to the elongate member between a first position and a second position about a center line of the elongate member between a first position and a second position. The connector is configured to allow the distal end portion of the elongate member to move relative to a spinal implant when the connector is in the first position. The connector is configured to connect the distal end portion of the elongate member to the spinal implant when the connector is in the second position. In some embodiments, for example, the connector can include multiple tines configured to complimentarily fit with an opening defined by the spinal implant when the connector is in the second position.

In some embodiments, an apparatus includes and elongate member including a cutting edge disposed at a distal end portion of the elongate member. The cutting edge is configured to cut a portion of a spinal implant when the elongate member moves relative to the spinal implant.

In some embodiments, an apparatus includes and elongate member and a cutting member. The cutting member is coupled to a distal end portion of the first elongate member. The cutting member configured to cut a portion of a spinal implant. In some embodiments, for example, the cutting member can move relative to the elongate member such that the cutting member cuts the portion of the spinal implant.

In some embodiments, a method includes inserting an elongate member into a body. The elongate member defines a center line and has a distal end portion. A locking member is disposed at the distal end portion of the elongate member. The distal end portion of the elongate member is moved into engagement with a spinal implant disposed within the body before the elongate member is inserted into the body. The locking member is moved relative to the elongate member between a first position and a second position in a direction substantially perpendicular to the center line such that the distal end portion of the elongate member is coupled to the spinal implant.

In some embodiments, a method includes inserting an elongate member into a body. A distal end portion of the elongate member is coupled to an outer member of a spinal implant disposed within the body before the elongate member is inserted into the body. An inner member of the spinal implant is moved relative to the outer member of the spinal implant after the distal end portion of the elongate member is coupled to the outer member of the spinal implant.

In some embodiments, a method includes coupling a distal end portion of an elongate member to a spinal implant disposed within a body. A portion of the spinal implant is cut with a cutting edge disposed at the distal end portion of the elongate member. In some embodiments, for example, a retention member of the spinal implant is cut with the cutting edge. In some embodiments, the method further includes deforming the portion of the spinal implant, either plastically or elastically, after it has been cut.

FIG. 1 is a schematic illustration of a medical device according to an embodiment of the invention adjacent two adjacent spinous processes. The medical device 10 includes a proximal portion 12, a distal portion 14 and a central portion 16. The medical device 10 has a first configuration in which it can be inserted between adjacent spinous processes S. The central portion 16 is configured to contact the spinous processes S to prevent over-extension/compression of the spinous processes S. In some embodiments, the central portion 16 does not substantially distract the adjacent spinous processes S. In other embodiments, the central portion 16 does not distract the adjacent spinous processes S.

In the first configuration, the proximal portion 12, the distal portion 14 and the central portion 16 are coaxial (i.e., share a common longitudinal axis). In some embodiments, the proximal portion 12, the distal portion 14 and the central portion 16 define a tube having a constant inner diameter. In other embodiments, the proximal portion 12, the distal portion 14 and the central portion 16 define a tube having a constant outer diameter and/or inner diameter.

Figure 2:
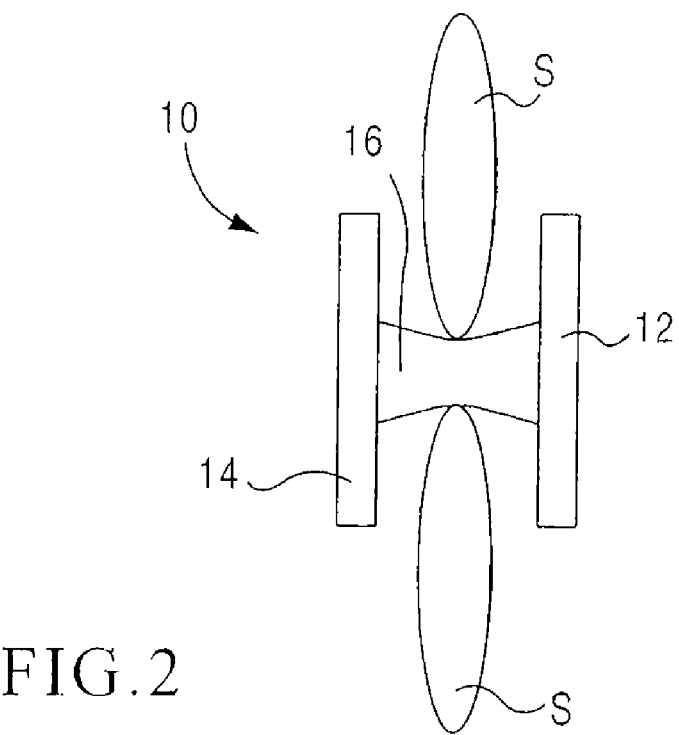
FIG. 2 is a schematic illustration of a posterior view of a medical device according to an embodiment of the invention in a second configuration adjacent two adjacent spinous processes.

The medical device 10 can be moved from the first configuration to a second configuration as illustrated in FIG. 2. In the second configuration, the proximal portion 12 and the distal portion 14 are positioned to limit lateral movement of the device 10 with respect to the spinous processes S. The proximal portion 12 and the distal portion 14 are configured to engage the spinous process (i.e., either directly or through surrounding tissue) in the second configuration. For purposes of clarity, the tissue surrounding the spinous processes S is not illustrated.

In some embodiments, the proximal portion 12, the distal portion 14 and the central portion 16 are monolithically formed. In other embodiments, one or more of the proximal portion 12, the distal portion 14 and the central portion 16 are separate components that can be coupled together to form the medical device 10. For example, the proximal portion 12 and distal portion 14 can be monolithically formed and the central portion can be a separate component that is coupled thereto.

In use, the spinous processes S can be distracted prior to inserting the medical device 10. Distraction of spinous processes is discussed below. When the spinous processes are distracted, a trocar can be used to define an access passage for the medical device 10. In some embodiments, the trocar can be used to define the passage as well as distract the spinous processes S. Once an access passage is defined, the medical device 10 is inserted percutaneously and advanced between the spinous processes, distal end 14 first, until the central portion 16 is located between the spinous processes S. Once the medical device 10 is in place between the spinous processes, the proximal portion 12 and the distal portion 14 are moved to the second configuration, either serially or simultaneously.

In some embodiments, the medical device 10 is inserted percutaneously (i.e., through an opening in the skin) and in a minimally-invasive manner. For example, as discussed in detail herein, the size of portions of the implant is expanded after the implant is inserted between the spinous processes. Once expanded, the size of the expanded portions of the implant is greater than the size of the opening. For example, the size of the opening/incision in the skin may be between 3 millimeters in length and 25 millimeters in length. In some embodiments, the size of the implant in the expanded configuration is between 3 and 25 millimeters.

Figure 3:
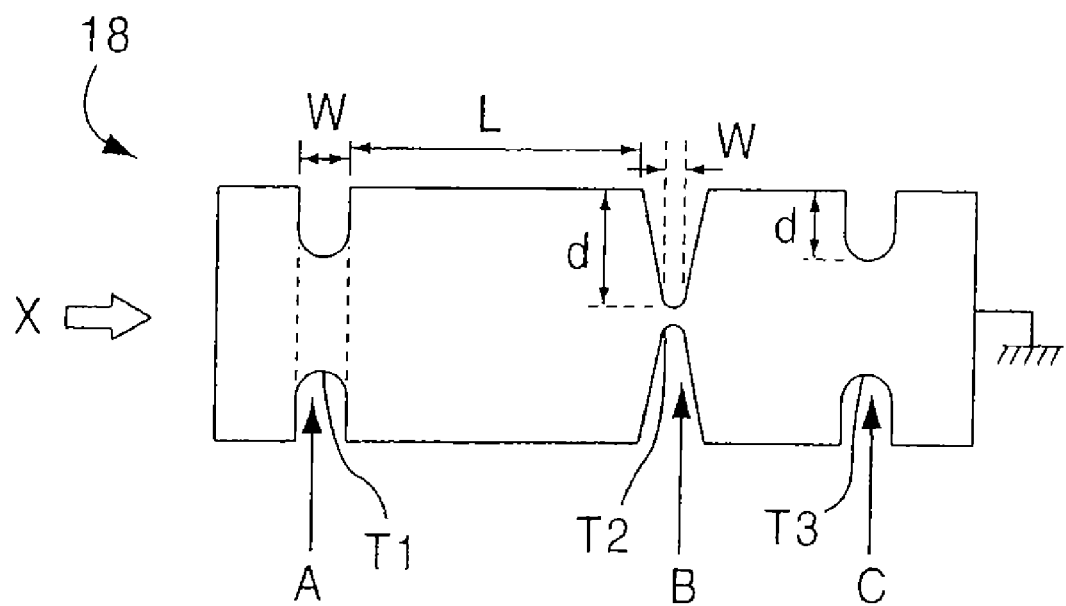
FIG. 3 is a schematic illustration of a deforming element according to an embodiment of the invention in a first configuration.

FIG. 3 is a schematic illustration of a deformable element 18 that is representative of the characteristics of, for example, the distal portion 14 of the medical device 10 in a first configuration. The deformable member 18 includes cutouts A, B, C along its length to define weak points that allow the deformable member 18 to deform in a predetermined manner. Depending upon the depth d of the cutouts A, B, C and the width w of the throats T1, T2, T3, the manner in which the deformable member 18 deforms under an applied load can be controlled and varied. Additionally, depending upon the length L between the cutouts A, B, C (i.e., the length of the material between the cutouts) the manner in which the deformable member 18 deforms can be controlled and varied.

Figure 4:
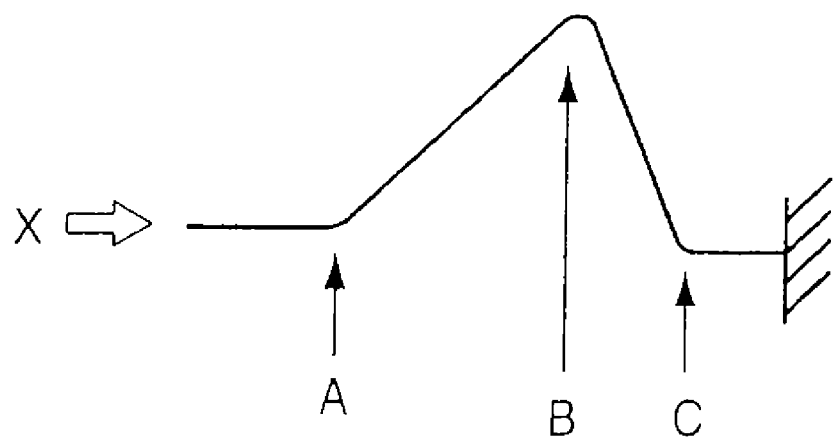
FIG. 4 is a schematic illustration of a side view of the expanding element illustrated in FIG. 3.

FIG. 4 is a schematic illustration of the expansion properties of the deformable member 18 illustrated in FIG. 3. When a load is applied, for example, in the direction indicated by arrow X, the deformable member 18 deforms in a predetermined manner based on the characteristics of the deformable member 18 as described above. As illustrated in FIG. 4, the deformable member 18 deforms most at cutouts B and C due to the configuration of the cutout C and the short distance between cutouts B and C. In some embodiments, the length of the deformable member 18 between cutouts B and C is sized to fit adjacent a spinous process.

The deformable member 18 is stiffer at cutout A due to the shallow depth of cutout A. As indicated in FIG. 4, a smooth transition is defined by the deformable member 18 between cutouts A and B. Such a smooth transition causes less stress on the tissue surrounding a spinous process than a more drastic transition such as between cutouts B and C. The dimensions and configuration of the deformable member 18 can also determine the timing of the deformation at the various cutouts. The weaker (i.e., deeper and wider) cutouts deform before the stronger (i.e., shallower and narrower) cutouts.

Figures 5, 6:
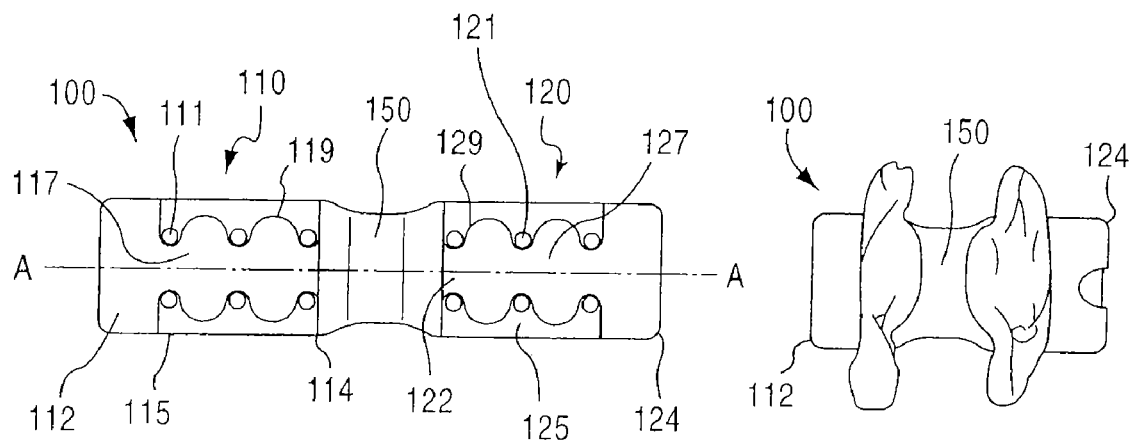
FIG. 5 is a side view of a medical device according to an embodiment of the invention in a first configuration.
FIG. 6 is a side view of the medical device illustrated in FIG. 5 in a second configuration.

FIGS. 5 and 6 illustrate a spinal implant 100 in a first configuration and second configuration, respectively. As shown in FIG. 5, the spinal implant 100 is collapsed in a first configuration and can be inserted between adjacent spinous processes. The spinal implant 100 has a first expandable portion 110, a second expandable portion 120 and a central portion 150. The first expandable portion 110 has a first end 112 and a second end 1140. The second expandable portion 120 has a first end 122 and a second end 124. The central portion 150 is coupled between second end 1140 and first end 122. In some embodiment, the spinal implant 100 is monolithically formed.

The first expandable portion 110, the second expandable portion 120 and the central portion 150 have a common longitudinal axis A along the length of spinal implant 100. The central portion 150 can have the same inner diameter as first expandable portion 110 and the second expandable portion 120. In some embodiments, the outer diameter of the central portion 150 is smaller than the outer diameter of the first expandable portion 110 and the second expandable portion 120.

In use, spinal implant 100 is inserted percutaneously between adjacent spinous processes. The first expandable portion 110 is inserted first and is moved past the spinous processes until the central portion 150 is positioned between the spinous processes. The outer diameter of the central portion 150 can be slightly smaller than the space between the spinous processes to account for surrounding ligaments and tissue. In some embodiments, the central portion directly contacts the spinous processes between which it is positioned. In some embodiments, the central portion of spinal implant 100 is a fixed size and is not compressible or expandable.

The first expandable portion 110 includes expanding members 115, 117 and 119. Between the expanding members 115, 117, 119, openings 111 are defined. As discussed above, the size and shape of the openings 111 influence the manner in which the expanding members 115, 117, 119 deform when an axial load is applied. The second expandable portion 120 includes expanding members 125, 127 and 129. Between the expanding members 125, 127, 129, openings 121 are defined. As discussed above, the size and shape of the openings 121 influence the manner in which the expanding members 125, 127, 129 deform when an axial load is applied.

When an axial load is applied to the spinal implant 100, the spinal implant 100 expands to a second configuration as illustrated in FIG. 6. In the second configuration, first end 112 and second end 1140 of the first expandable portion 110 move towards each other and expanding members 115, 117, 119 project substantially laterally away from the longitudinal axis A. Likewise, first end 122 and second end 124 of the second expandable portion 120 move towards one another and expanding members 125, 127, 129 project laterally away from the longitudinal axis A. The expanding members 115, 117, 119, 125, 127, 129 in the second configuration form projections that extend to positions adjacent to the spinous processes between which the spinal implant 100 is inserted. In the second configuration, the expanding members 115, 117, 119, 125, 127, 129 inhibit lateral movement of the spinal implant 100, while the central portion 150 prevents the adjacent spinous processes from moving together any closer than the distance defined by the diameter of the central portion 150.

Figure 7:
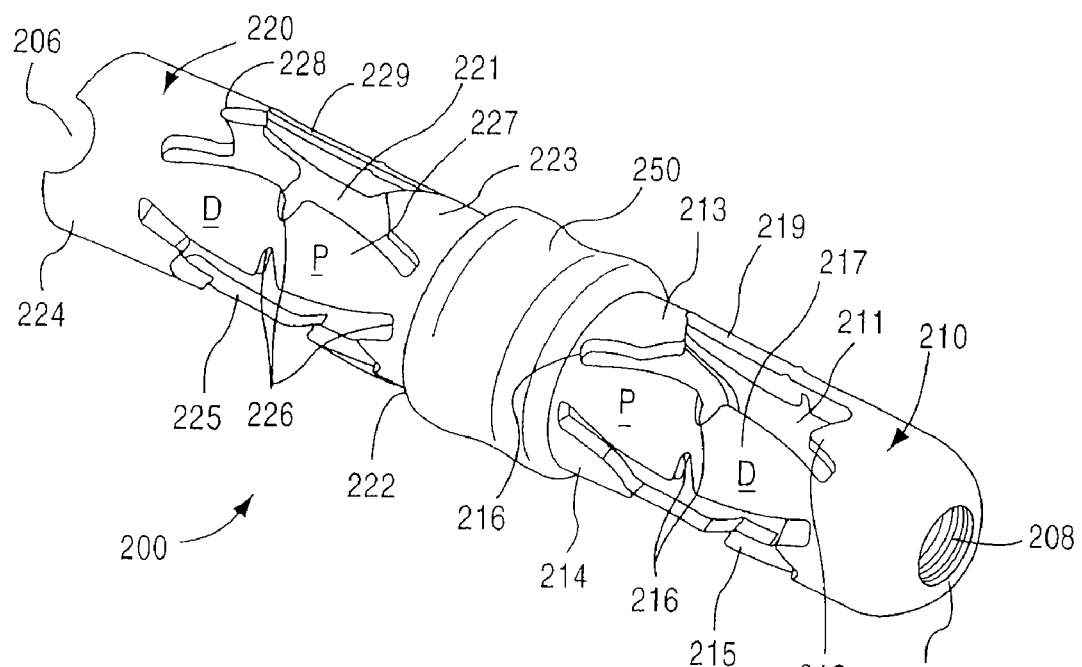
FIG. 7 is a perspective view of a medical device according to an embodiment of the invention in a first configuration.
Figure 8:
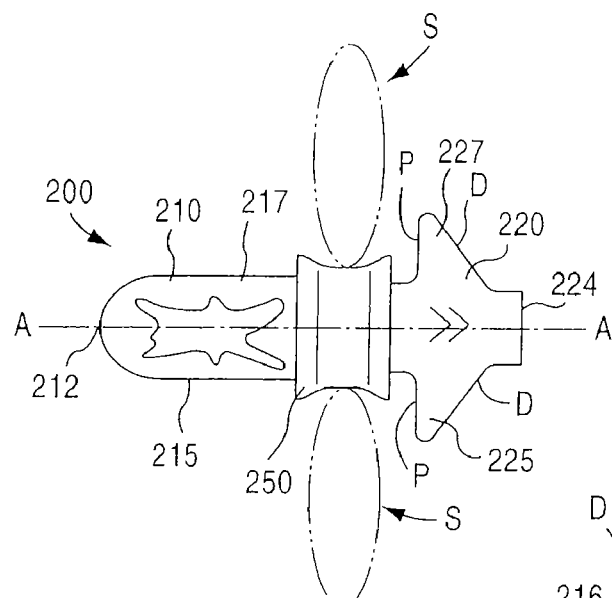
FIG. 8 is a posterior view of a medical device according to an embodiment of the invention, a portion of which is in a second configuration.
Figure 9:
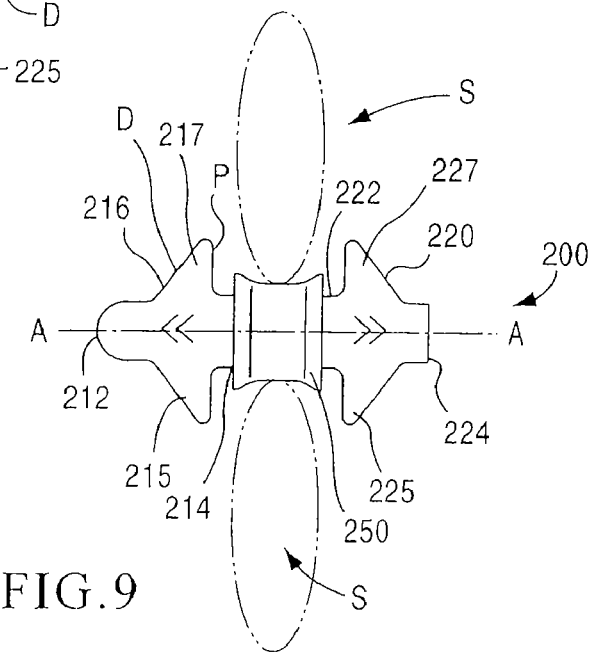
FIG. 9 is a posterior view of the medical device illustrated in FIG. 7 fully deployed in the second configuration.

A spinal implant 200 according to an embodiment of the invention is illustrated in FIGS. 7-9 in various configurations. Spinal implant 200 is illustrated in a completely collapsed configuration in FIG. 7 and can be inserted between adjacent spinous processes. The spinal implant 200 has a first expandable portion 210, a second expandable portion 220 and a central portion 250. The first expandable portion 210 has a first end 212 and a second end 214. The second expandable portion 220 has a first end 222 and a second end 224. The central portion 250 is coupled between second end 214 and first end 222.

The first expandable portion 210, the second expandable portion 220 and the central portion 250 have a common longitudinal axis A along the length of spinal implant 200. The central portion 250 can have the same inner diameter as first expandable portion 210 and the second expandable portion 220. The outer diameter of the central portion 250 is greater than the outer diameter of the first expandable portion 210 and the second expandable portion 220. The central portion 250 can be monolithically formed with the first expandable portion 210 and the second expandable portion 220 or can be a separately formed sleeve coupled thereto or thereupon.

In use, spinal implant 200 is inserted percutaneously between adjacent spinous processes S. The first expandable portion 210 is inserted first and is moved past the spinous processes S until the central portion 250 is positioned between the spinous processes S. The outer diameter of the central portion 250 can be slightly smaller than the space between the spinous processes S to account for surrounding ligaments and tissue. In some embodiments, the central portion 250 directly contacts the spinous processes S between which it is positioned. In some embodiments, the central portion 250 of spinal implant 200 is a fixed size and is not compressible or expandable. In other embodiments, the central portion 250 can compress to conform to the shape of the spinous processes.

The first expandable portion 210 includes expanding members 215, 217 and 219. Between the expanding members 215, 217, 219, openings 211 are defined. As discussed above, the size and shape of the openings 211 influence the manner in which the expanding members 215, 217, 219 deform when an axial load is applied. Each expanding member 215, 217, 219 of the first expandable portion 210 includes a tab 213 extending into the opening 211 and an opposing mating slot 218. In some embodiments, the first end 212 of the first expandable portion 210 is rounded to facilitate insertion of the spinal implant 200.

The second expandable portion 220 includes expanding members 225, 227 and 229. Between the expanding members 225, 227, 229, openings 221 are defined. As discussed above, the size and shape of the openings 221 influence the manner in which the expanding members 225, 227, 229 deform when an axial load is applied. Each expanding member 225, 227, 229 of the second expandable portion 220 includes a tab 223 extending into the opening 221 and an opposing mating slot 228.

When an axial load is applied to the spinal implant 200, the spinal implant moves to a partially expanded configuration as illustrated in FIG. 8. In the partially expanded configuration, first end 222 and second end 224 of the second expandable portion 220 move towards one another and expanding members 225, 227, 229 project laterally away from the longitudinal axis A. To prevent the second expandable portion 220 from over-expanding, the tab 223 engages slot 228 and acts as a positive stop. As the axial load continues to be imparted to the spinal implant 200 after the tab 223 engages slot 228, the load is transferred to the first expandable portion 210. Accordingly, the first end 212 and the second end 214 then move towards one another until tab 213 engages slot 218 in the fully expanded configuration illustrated in FIG. 9. In the second configuration, expanding members 215, 217, 219 project laterally away from the longitudinal axis A. In some alternative embodiments, the first expandable portion and the second expandable portion expand simultaneously under an axial load.

The order of expansion of the spinal implant 200 can be controlled by varying the size of openings 211 and 221. For example, in the embodiments shown in FIGS. 7-9, the opening 221 is slightly larger than the opening 211. Accordingly, the notches 226 are slightly larger than the notches 216. As discussed above with respect to FIGS. 3 and 4, for this reason, the second expandable portion 220 will expand before the first expandable portion 210 under an axial load.

In the second configuration, the expanding members 215, 217, 219, 225, 227, 229 form projections that extend adjacent the spinous processes S. Once in the second configuration, the expanding members 215, 217, 219, 225, 227, 229 inhibit lateral movement of the spinal implant 200, while the central portion 250 prevents the adjacent spinous processes from moving together any closer than the distance defined by the diameter of the central portion 250.

The portion P of each of the expanding members 215, 217, 219, 225, 227, 229 proximal to the spinous process S expands such that portion P is substantially parallel to the spinous process S. The portion D of each of the expanding members 215, 217, 219, 225, 227, 229 distal from the spinous process S is angled such that less tension is imparted to the surrounding tissue.

Figure 10:
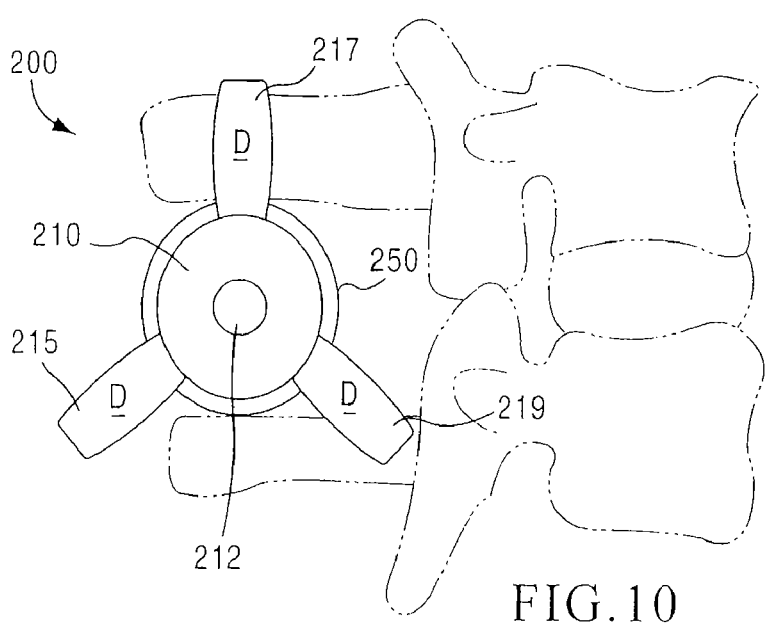
FIG. 10 is a front plan view of the medical device illustrated in FIG. 7 in the second configuration.
Figure 11:
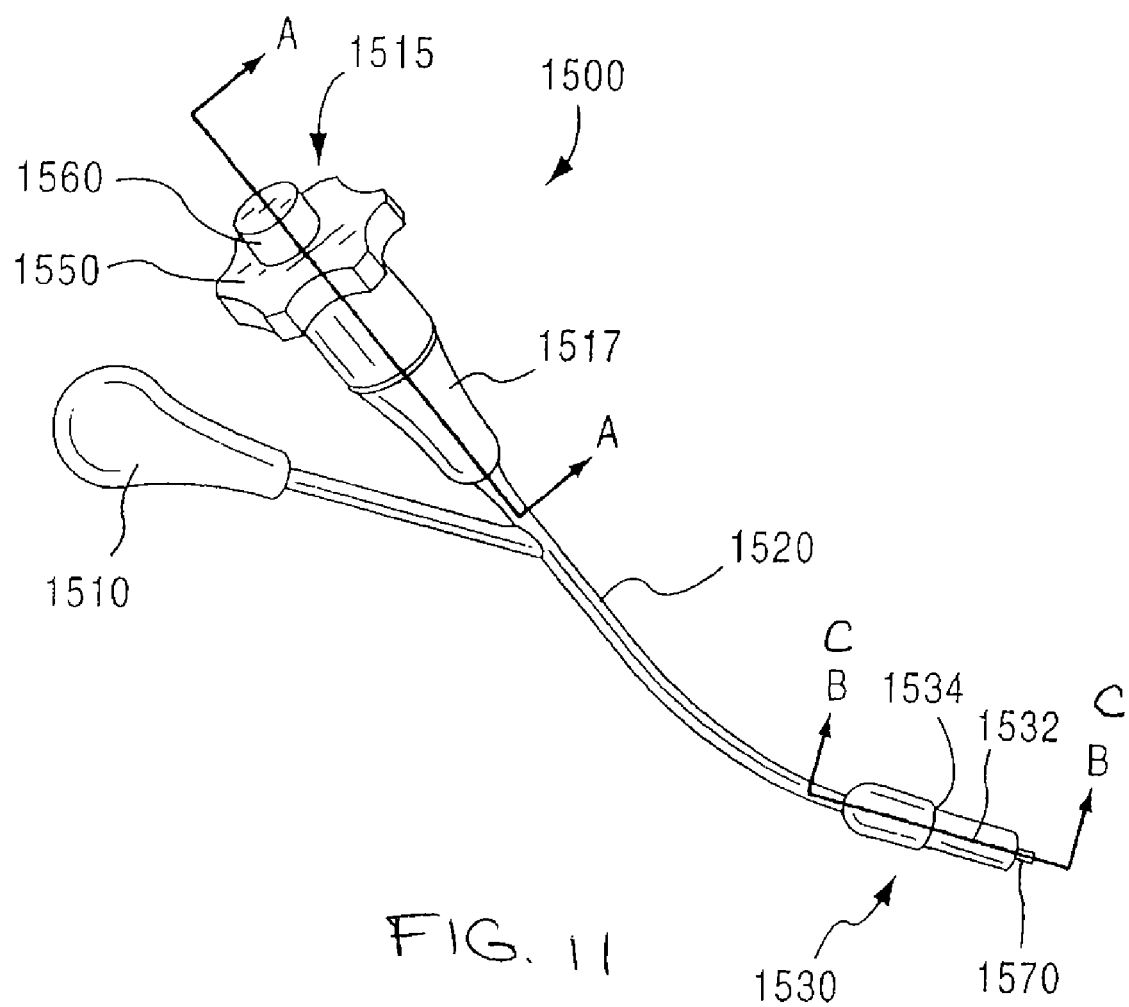
FIG. 11 is a perspective view of an implant expansion device according to an embodiment of the invention.
Figure 12:
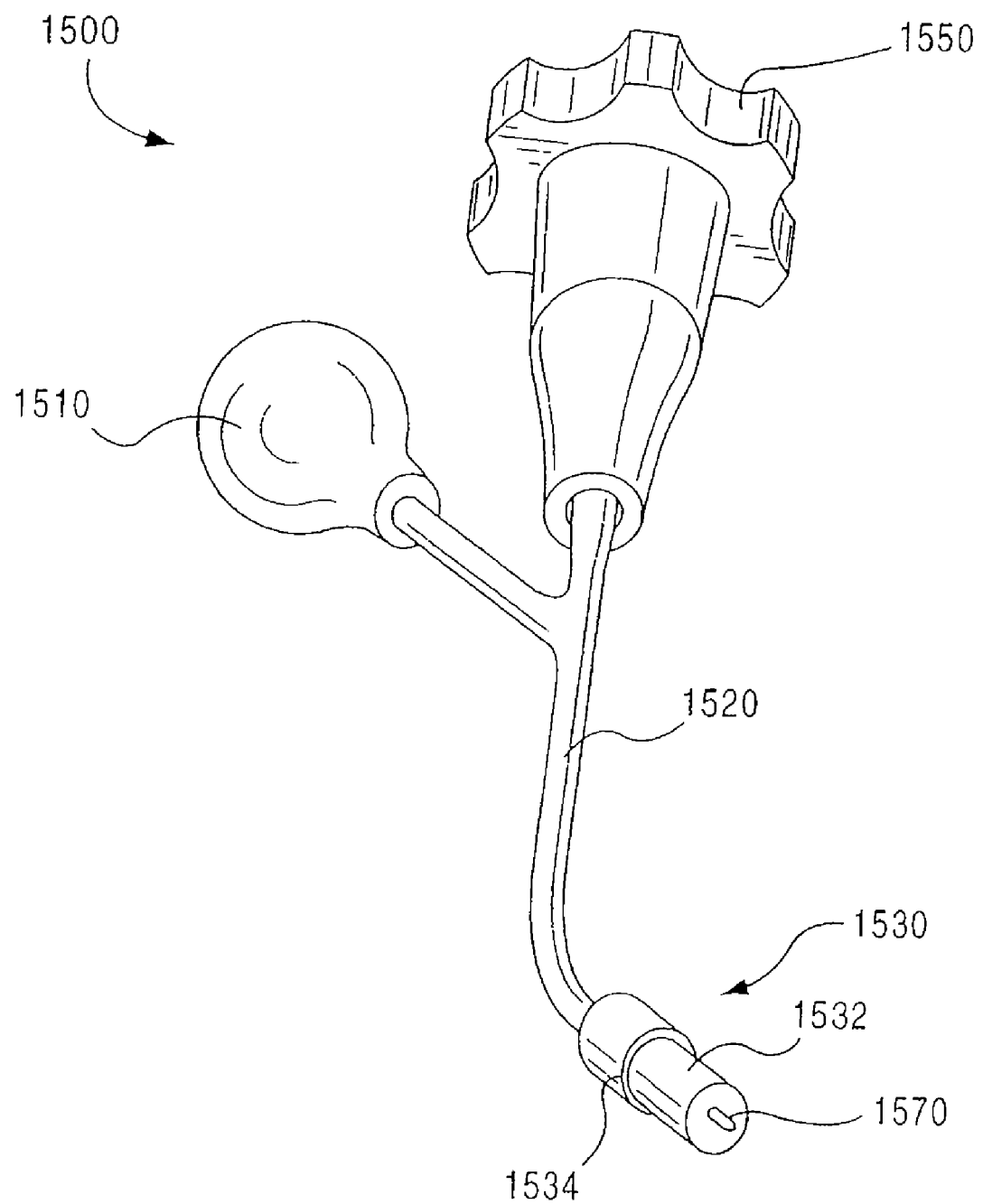
FIG. 12 is an alternative perspective view of the implant expansion device illustrated in FIG. 11.
Figure 13:
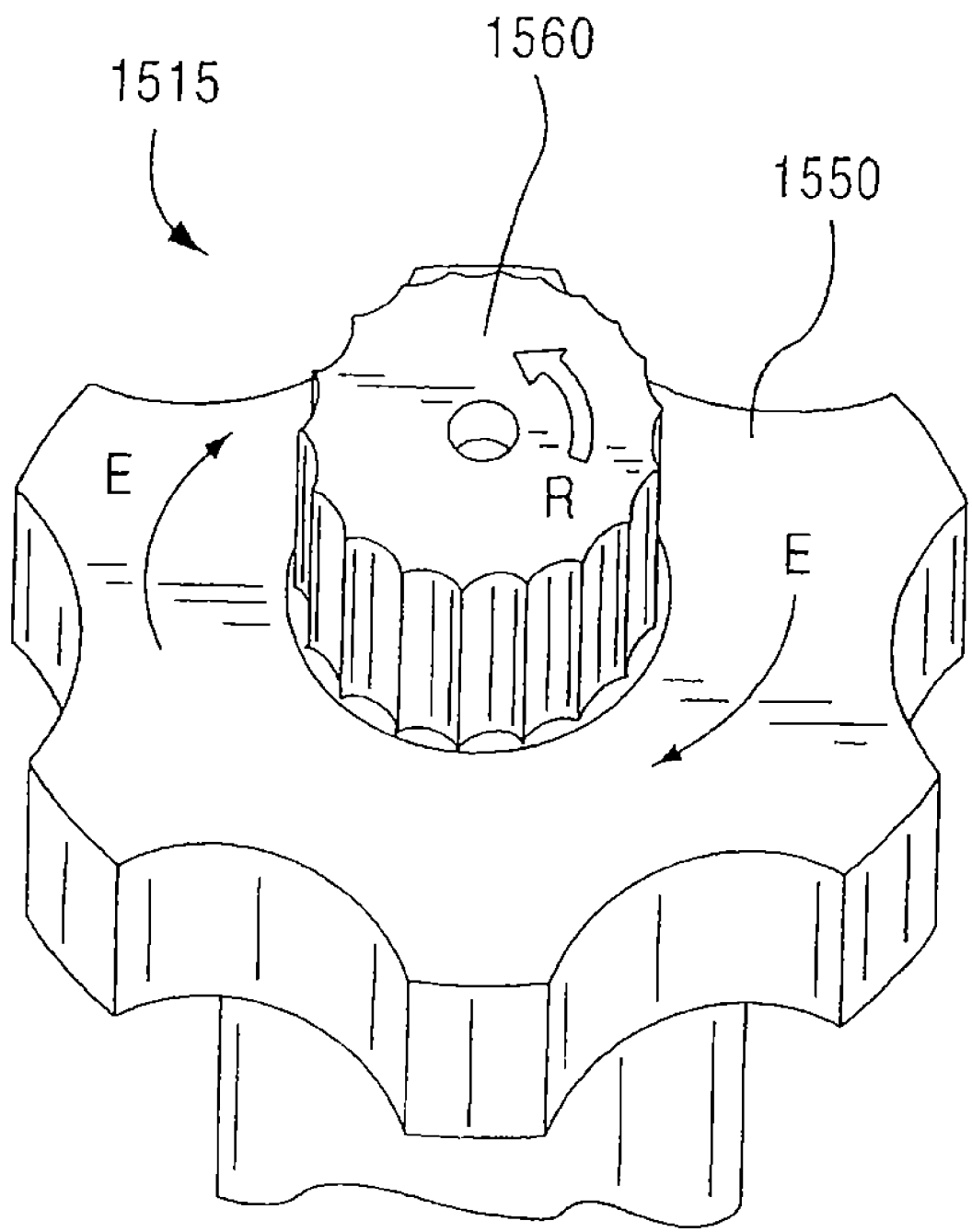
FIG. 13 is a perspective view of a portion of the implant expansion device illustrated in FIG. 11.

In the second configuration, the expanding members 225, 227, 229 are separate by approximately 120 degrees from an axial view as illustrated in FIG. 10. While three expanding members are illustrated, two or more expanding members may be used and arranged in an overlapping or interleaved fashion when multiple implants 200 are inserted between multiple adjacent spinous processes. Additionally, regardless of the number of expanding members provided, the adjacent expanding members need not be separated by equal angles or distances.

The spinal implant 200 is deformed by a compressive force imparted substantially along the longitudinal axis A of the spinal implant 200. The compressive force is imparted, for example, by attaching a rod (not illustrated) to the first end 212 of the first expandable portion 210 and drawing the rod along the longitudinal axis while imparting an opposing force against the second end 224 of the second expandable portion 220. The opposing forces result in a compressive force causing the spinal implant 200 to expand as discussed above.

The rod used to impart compressive force to the spinal implant 200 can be removably coupled to the spinal implant 200. For example, the spinal implant 200 can include threads 208 at the first end 212 of the first expandable portion 210. The force opposing that imparted by the rod can be applied by using a push bar (not illustrated) that is removably coupled to the second end 224 of the second expandable portion 220. The push rod can be aligned with the spinal implant 200 by an alignment notch 206 at the second end 224. The spinal implant 200 can also be deformed in a variety of other ways, using a variety of expansion devices (also referred to herein as insertion tools, deployment tools and/or removal tools). While various types of implants are illustrated with various types of expansion devices, the expansion devices described herein can be used with any of the implants described herein.

FIGS. 11-16 illustrate an expansion device 1500 (also referred to herein as an insertion tool or a deployment tool) according to an embodiment of the invention. Although no particular implant is illustrated in FIGS. 11-16, any of the implants described herein, such as, for example, implant 200 (see FIG. 7), can be used with the expansion device 1500. The expansion device 1500 includes a guide handle 1510, a knob assembly 1515, a shaft 1520, a rod 1570 and an implant support portion 1530. The expansion device 1500 is used to insert an implant (not illustrated) in between adjacent spinous processes and expand the implant such that it is maintained in position between the spinous processes as described above. Both the guide handle 1510 and the knob assembly 1515 can be grasped to manipulate the expansion device 1500 to insert the implant. As described in more detail herein, the knob assembly 1515 is configured such that as the knob assembly 1515 is actuated, the rod 1570 translates and/or rotates within the shaft 1520; when the rod 1570 translates, the implant (not illustrated) is moved between its collapsed configuration and its expanded configuration; when the rod 1570 rotates, the implant is disengaged from the rod 1570.

As best illustrated in FIGS. 15 and 16, the implant support portion 1530 includes a receiving member 1538 and a spacer 1532. The receiving member 1538 includes a side wall 1540 that is coupled to and supported by the distal end of the shaft 1520. The side wall 1540 defines an alignment protrusion 1536 and a receiving area 1542 configured to receive a portion of the spacer 1532. The implant slides over spacer 1532 until its proximal end is received within a recess 1534 defined by the side wall 1540 and the outer surface of the spacer 1532. The alignment protrusion 1536 is configured to mate with a corresponding notch on the implant (see, e.g., alignment notch 206 in FIG. 7) to align the implant with respect to the expansion device. Once the implant is aligned within the implant support portion 1530, the distal end of the implant is threadedly coupled to the distal end of rod 1570.

As illustrated, the spacer 1532 ensures that the implant is aligned longitudinally during the insertion and expansion process. The spacer 1532 can also be configured to maintain the shape of the implant during insertion and to prevent the expandable portions of the implant from extending inwardly during deployment of the implant. For example, in some embodiments, the spacer 1532 can be constructed from a solid, substantially rigid material, such as stainless steel, having an outer diameter and length corresponding to the inner diameter and length of the implant. In other embodiments, the expansion device can be configured to be used with implants that include an inner core configured to provide structural support to the implant (see, for example, FIGS. 17-23). In such embodiments, as described in more detail herein, the spacer of the insertion tool can be configured to cooperate with the inner core of the implant to provide the alignment and structural support of the implant during insertion and expansion.

Figure 14:
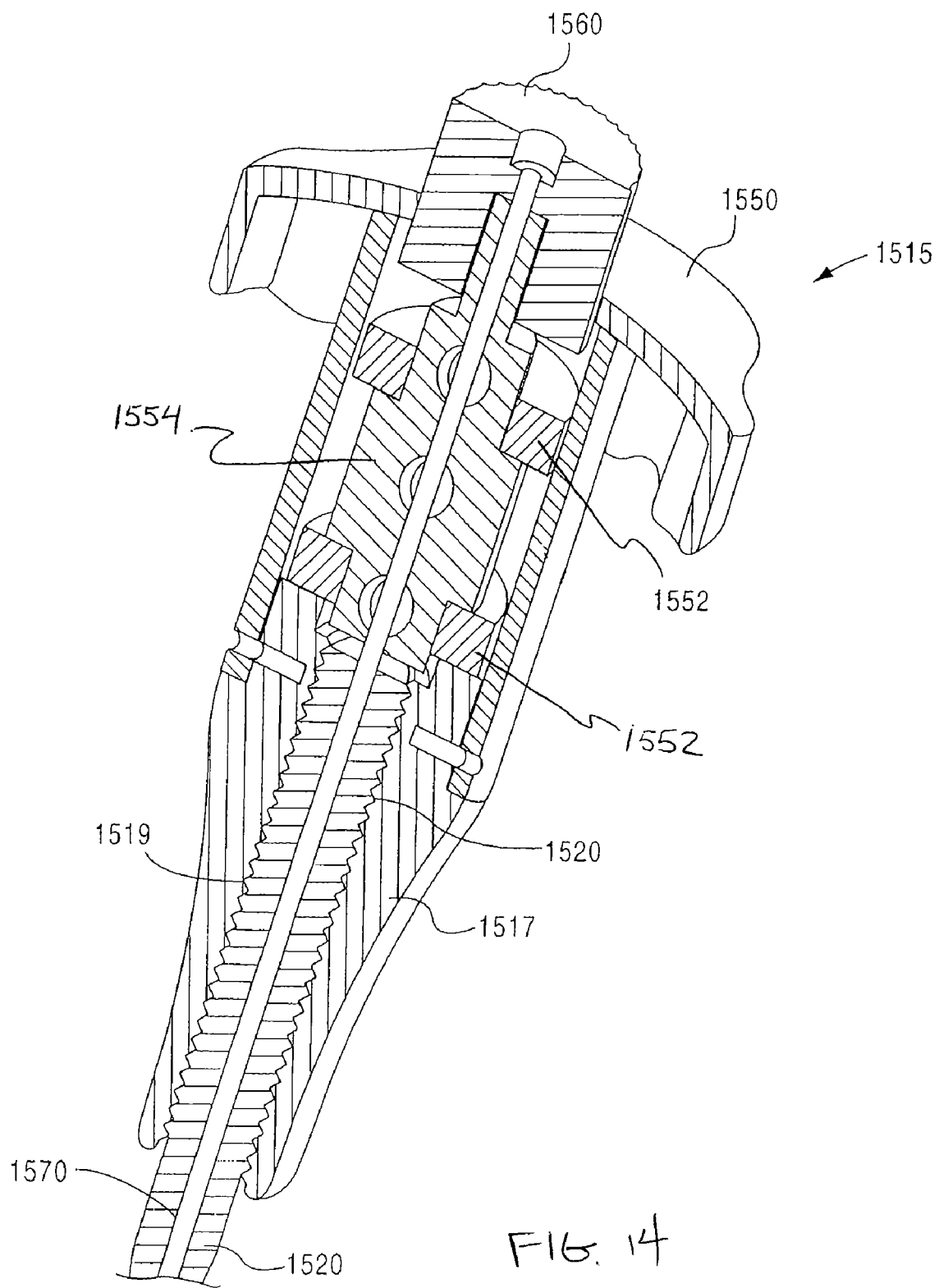
FIG. 14 is a cross-sectional view of a portion of the device illustrated in FIG. 11, taken along line A-A in FIG. 11.

The knob assembly 1515 includes an upper housing 1517 that threadedly receives the shaft 1520, an actuator knob 1550 and a release knob 1560 as best illustrated in FIG. 14. Upper housing 1517 includes internal threads 1519 that mate with external threads 1521 on shaft 1520. The proximal end of rod 1570 is coupled to the knob assembly 1515 by an adapter 1554, which is supported by two thrust bearings 1552. Actuator knob 1550 is coupled to the upper housing 1517 and is engaged with the adapter 1554 such that when actuator knob 1550 is turned in the direction indicated by arrows E (see FIG. 13), the rod 1570 translates axially relative to the shaft 1520 towards the proximal end of the device 1500, thereby acting as a draw bar and opposing the movement of the implant in the distal direction. In other words, when the implant is inserted between adjacent spinous processes and the actuator knob 1515 is turned, the distal end of the implant support portion 1530 imparts an axial force against the proximal end of the implant, while the rod 1570 causes an opposing force in the proximal direction. In this manner, the forces imparted by the implant support portion and the rod 1570 cause portions of the implant to expand in a transverse configuration such that the implant is maintained in position between the spinous processes as described above. The expansion device 1500 can also be used to move the implant from its expanded configuration to its collapsed configuration by turning the actuator knob 1550 in the opposite direction.

Once the implant is in position and fully expanded, the release knob 1560 is turned in the direction indicated by arrow R (see FIG. 13) thereby causing the rod 1570 to rotate within the shaft 1520. In this manner, the implant can be disengaged from the rod 1570. During this operation, the implant is prevented from rotating by the alignment protrusion 1536, which is configured to mate with a corresponding notch on the implant. Once the implant is decoupled from the rod 1570, the expansion tool 1500 can then be removed from the patient.

Although the knob assembly 1515 is shown and described as including an actuator knob 1550 and a release knob 1560 that are coaxially arranged with a portion of the release knob 1560 being disposed within the actuator knob 1550, in some embodiments, the release knob is disposed apart from the actuator knob. In other embodiments, the release knob and the actuator knob are not coaxially located. In yet other embodiments, the knob assembly 1515 does not include knobs having a circular shape, but rather includes levers, handles or any other device suitable for actuating the rod relative to the shaft as described above.

Figure 17:
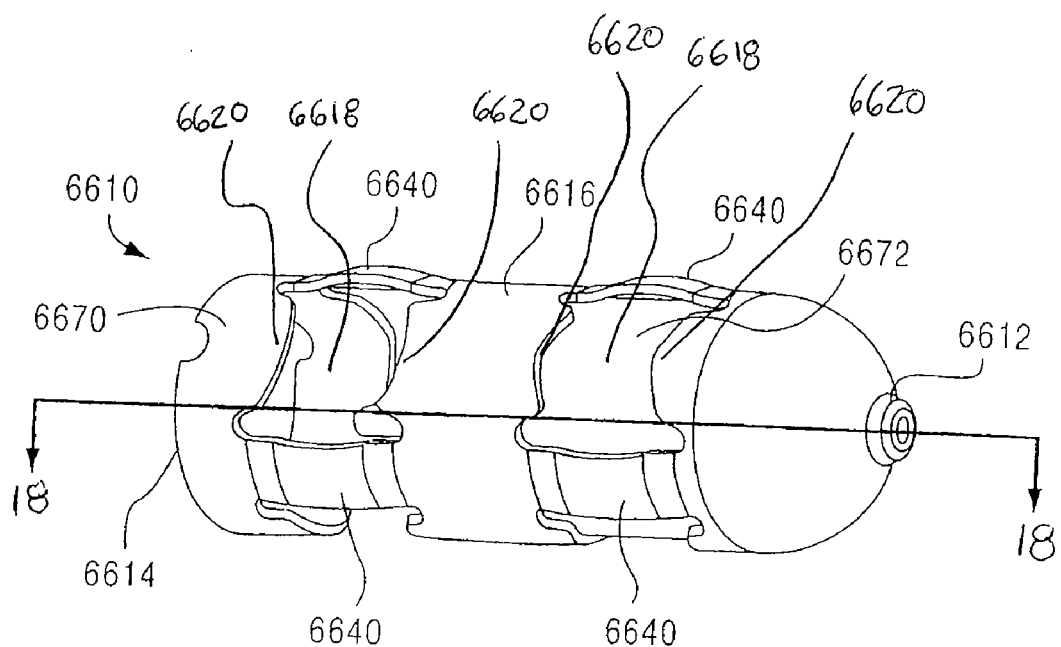
FIG. 17 is a side perspective view of an implant according to an embodiment of the invention shown in a collapsed configuration.
Figure 18:
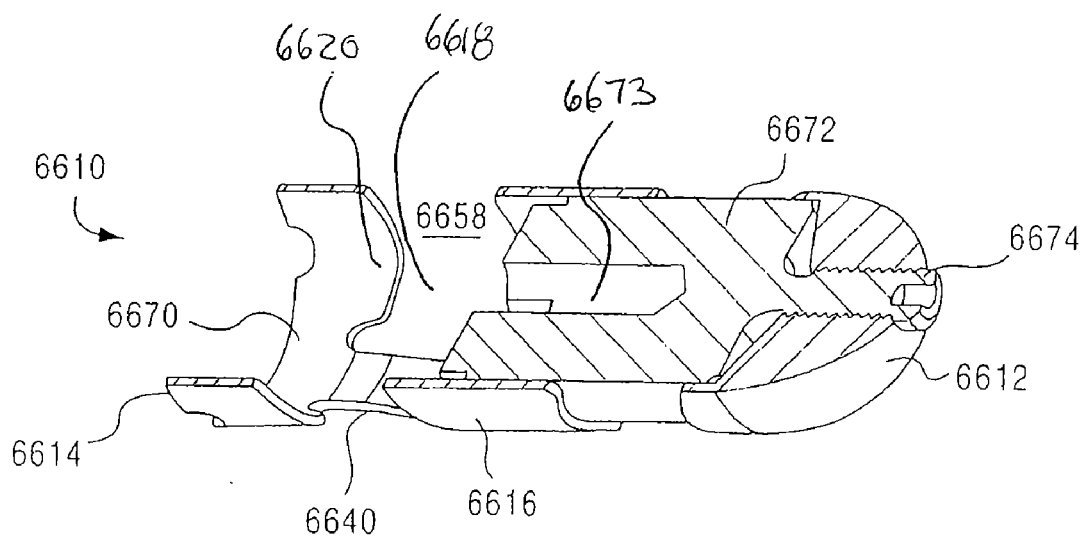
FIG. 18 is a cross-sectional view of the implant of FIG. 17 taken along line 18-18.
Figure 19:
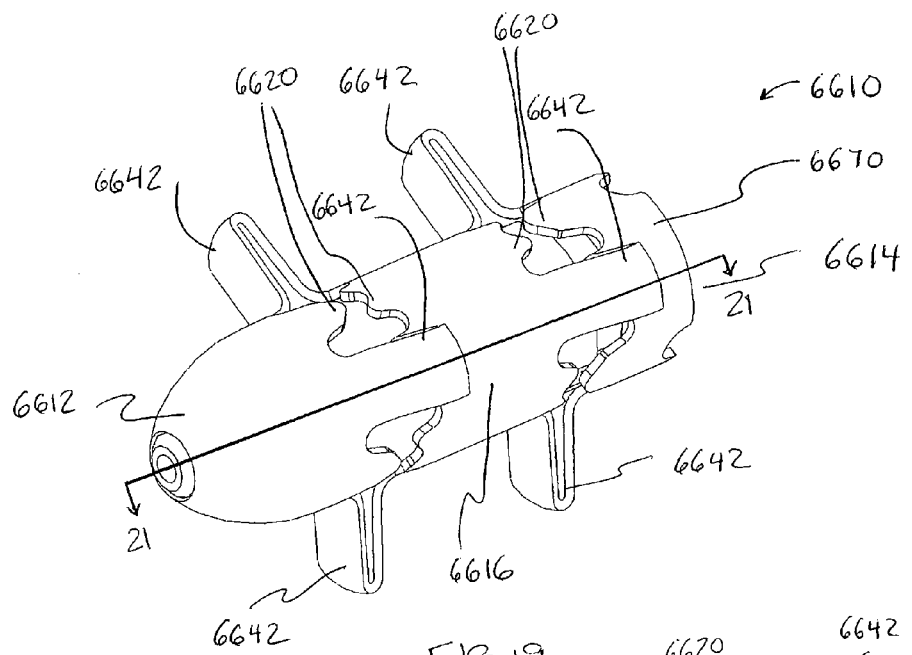
FIG. 19 is a side perspective view of the implant of FIG. 17 shown in an expanded configuration.
Figure 20:
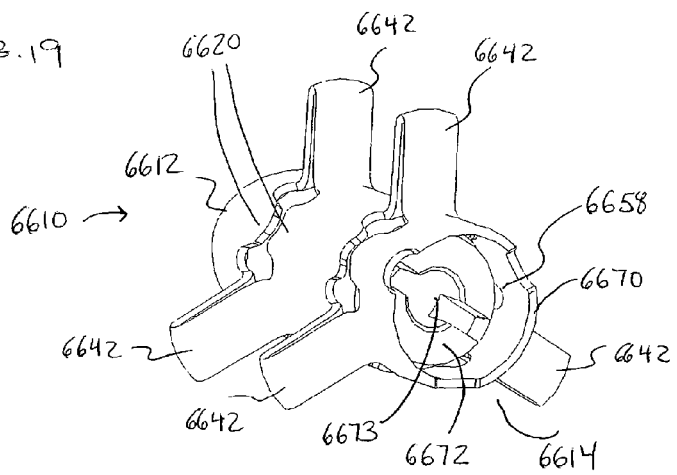
FIG. 20 is a rear perspective view of the implant of FIG. 17 shown in a collapsed configuration.
Figure 21:
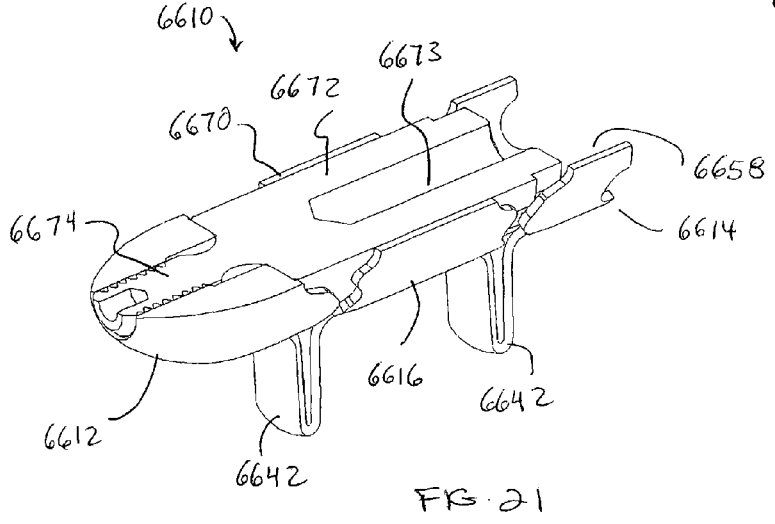
FIG. 21 is cross-sectional view of the implant of FIG. 17 shown in a collapsed configuration taken along line 21-21.
Figure 22:
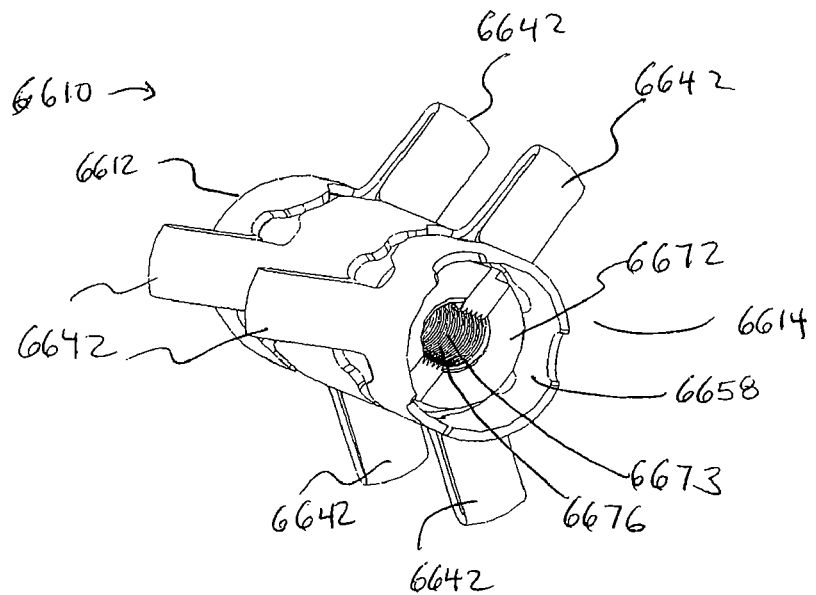
FIG. 22 is a rear perspective view of an implant according to an embodiment of the invention shown in a collapsed configuration.
Figure 23:
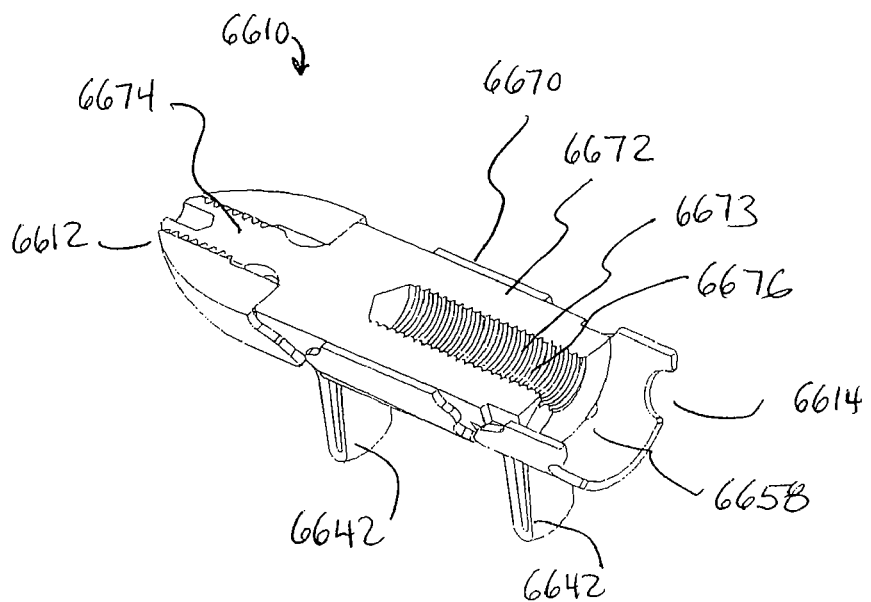
FIG. 23 is a cross-sectional view of the implant of FIG. 22 shown in a collapsed configuration.
Figure 24:
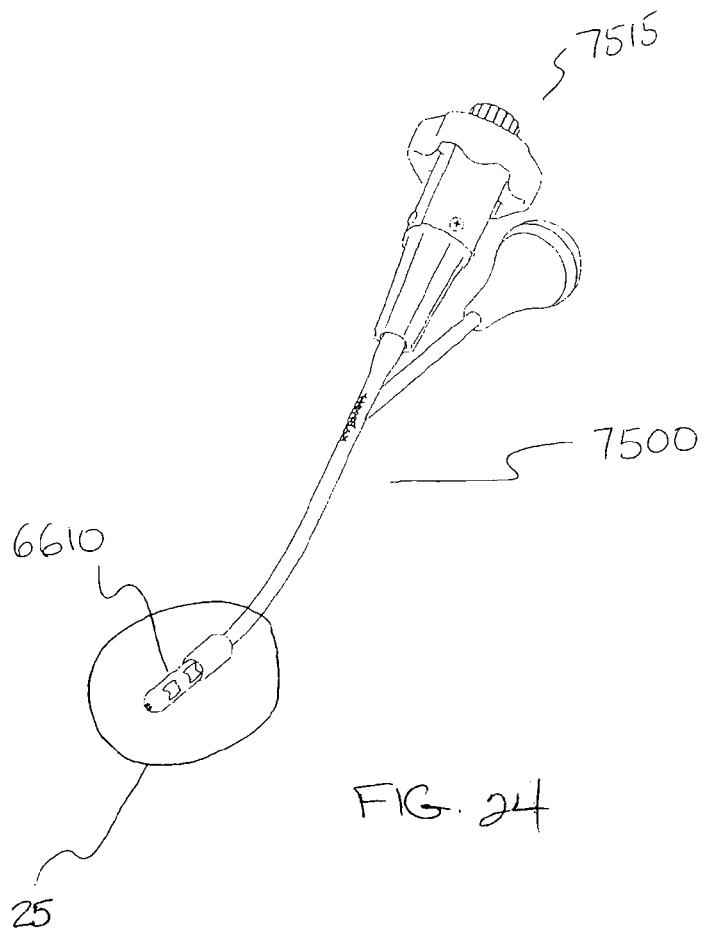
FIG. 24 is a perspective view of the implant of FIG. 22 in a collapsed configuration disposed on an expansion tool according to an embodiment of the invention.
Figure 25:
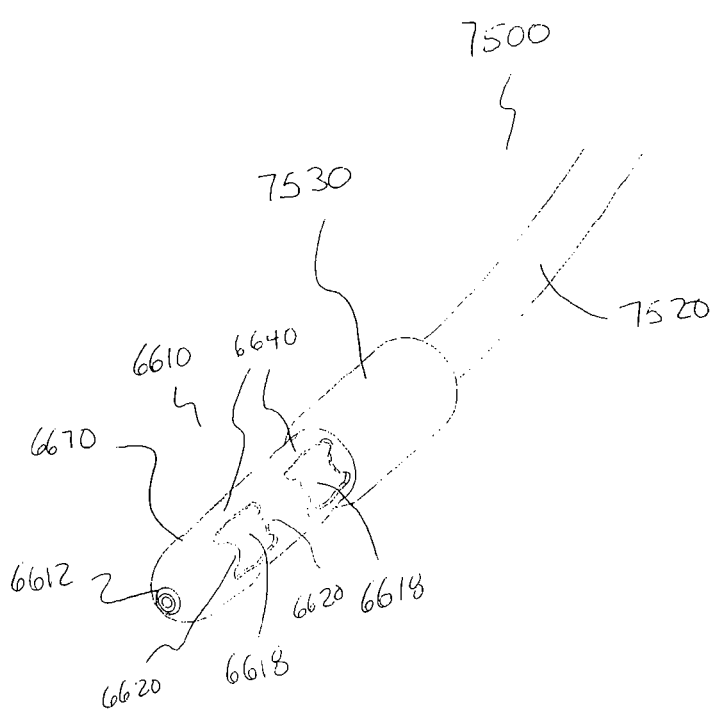
FIG. 25 is a perspective view of the implant and the expansion tool of FIG. 24 taken along region 25.
Figure 26:
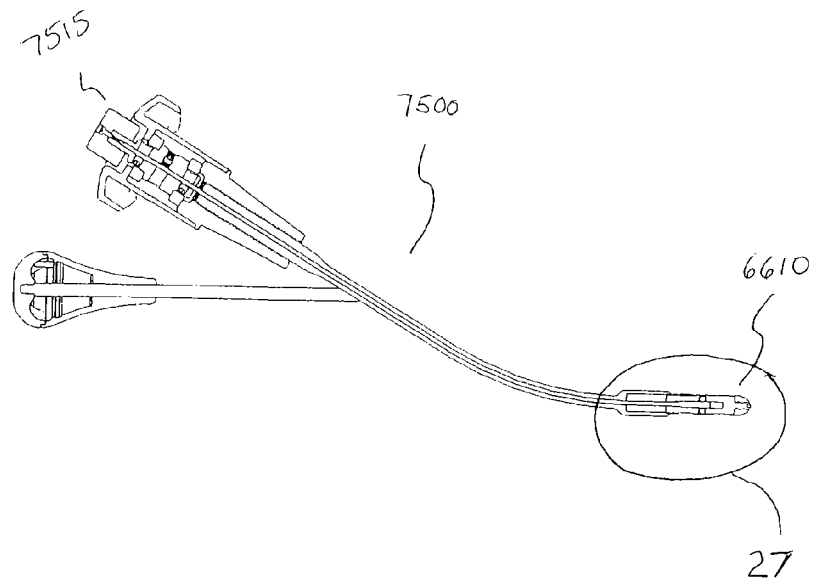
FIG. 26 is a side cross-sectional view of the implant and the expansion tool of FIG. 24.
Figure 27:
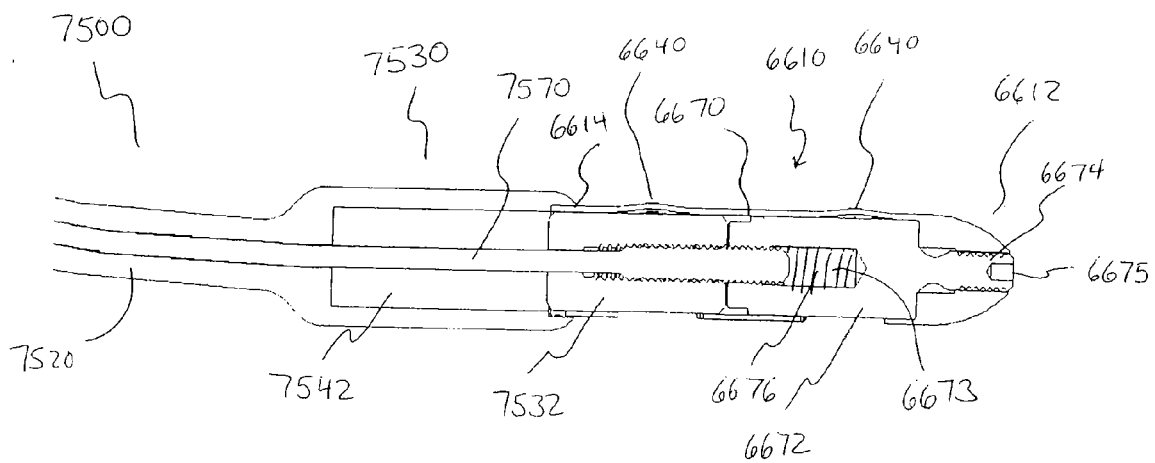
FIG. 27 is a side cross-sectional view of the implant and the expansion tool as shown in FIG. 26 taken along region 27.
Figure 28:
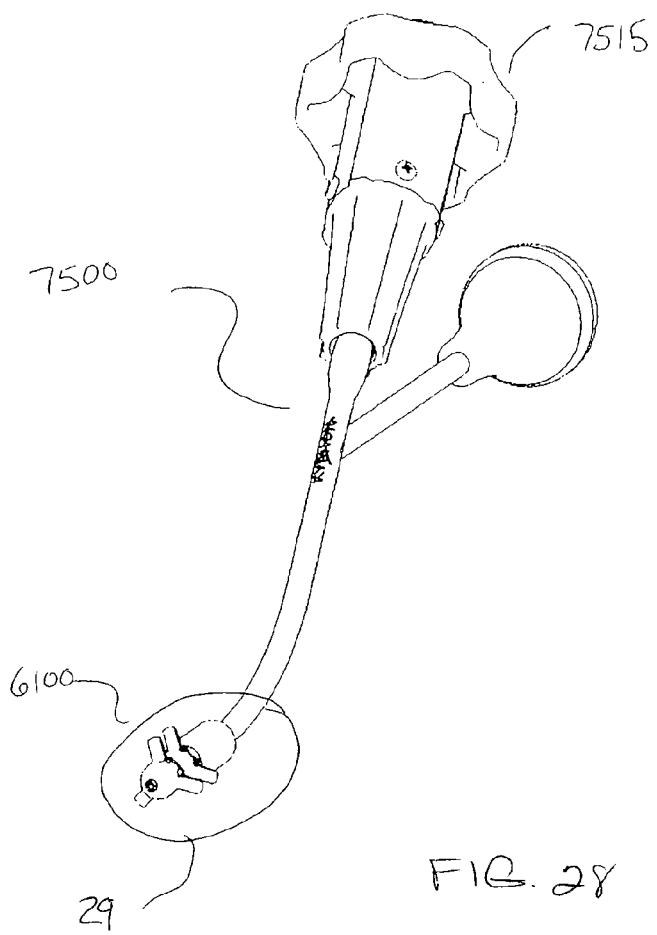
FIG. 28 is a perspective view of the implant of FIG. 22 in an expanded configuration disposed on an expansion tool according to an embodiment of the invention.

FIGS. 17-23 illustrate an implant 6610 according to another embodiment of the invention. The implant 6610 can be moved between a collapsed configuration, as shown in FIGS. 17 and 18, and an expanded configuration, as shown in FIGS. 19-23. The implant 6610 includes an outer shell 6670 having a distal portion 6612, a proximal portion 6614, and a central portion 6616. The outer shell 6670 defines a series of openings 6618 disposed between the distal portion 6612 and the central portion 6616, and the proximal portion 6614 and the central portion 6616. The outer shell 6670 includes a series of tabs 6620, a pair of which are disposed opposite each other, along the longitudinal axis of the implant 6610, on either side of each opening 6618. The outer shell 6670 also includes expandable portions 6640, which form extensions 6642 that extend radially from the outer shell 6670 when the implant 6610 is in the expanded configuration. As illustrated best in FIGS. 19-23, the arrangement of the openings 6618 and the tabs 6620 effect the shape and/or size of the extensions 6642. In some embodiments, the opposing tabs 6620 can be configured to engage each other when the implant 6610 is in the expanded configuration, thereby serving as a positive stop to limit the amount of expansion. In other embodiments, for example, the opposing tabs 6620 can be configured to engage each other during the expansion process, thereby serving as a positive stop, but remain spaced apart when the implant 6610 is in the expanded configuration (see, for example, FIGS. 19-23). In such embodiments, the elastic properties of the extensions 6642 can cause a slight "spring back," thereby causing the opposing tabs 6620 to be slightly spaced apart when the expansion device (also referred to as an insertion tool or a deployment tool) is disengaged from the implant 6610.

As illustrated best in FIG. 17, when the implant is in the collapsed configuration, the expandable portions 6640 are contoured to extend slightly radially from remaining portions of the outer shell 6670. In this manner, the expandable portions 6640 are biased such that when a compressive force is applied, the expandable portions 6640 will extend outwardly from the outer shell 6670. The expandable portions 6640 can be biased using any suitable mechanism. In some embodiments, for example, the expandable portions can be biased by including a notch in one or more locations along the expandable portion, as previously described. In other embodiments, the expandable portions can be biased by varying the thickness of the expandable portions in an axial direction. In yet other embodiments, the expandable portions can be stressed or bent prior to insertion such that the expandable portions are predisposed to extend outwardly when a compressive force is applied to the implant. In such embodiments, the radius of the expandable portions is greater than that of the remaining portions of the implant (e.g., the remaining cylindrical portions of the implant).

The implant 6610 also includes an inner core 6672 disposed within a lumen 6658 defined by the outer shell 6670. The inner core 6672 is configured to maintain the shape of the implant 6610 during insertion, to prevent the expandable portions from extending inwardly into a region inside of the outer shell 6670 during deployment and/or to maintain the shape of the central portion 6616 once the implant is in its desired position. As such, the inner core 6670 can be constructed to provide increased compressive strength to the outer shell 6670. In other words, the inner core 6672 can provide additional structural support to outer shell 6670 (e.g., in a direction transverse to the axial direction) by filling at least a portion of the region inside outer shell 6670 (e.g., lumen 6658) and contacting the walls of outer shell 6670. This can increase the amount of compressive force that can be applied to the implant 6610 while the implant 6610 still maintains its shape and, for example, the desired spacing between adjacent spinous processes. In some embodiments, the inner core 6672 can define a lumen 6673, while in other embodiments, the inner core 6672 can have a substantially solid construction. As illustrated, the inner core 6672 is fixedly coupled to the outer shell 6670 with a coupling portion 6674, which is configured to be threadedly coupled to the distal portion 6612 of the outer shell 6670. The distal end of the coupling portion 6674 of the inner core 6672 includes an opening 6675 configured to receive a tool configured to deform the distal end of the coupling portion 6674. In this manner once the inner core 6672 is threadedly coupled to the outer shell 6670, the coupling portion 6674 can be deformed or peened to ensure that the inner core 6672 does not become inadvertently decoupled from the outer shell 6670. In some embodiments, an adhesive, such as a thread-locking compound can be applied to the threaded portion of the coupling portion 6674 to ensure the that the inner core 6672 does not inadvertently become decoupled from the outer shell 6670. Although illustrated as being threadedly coupled, the inner core 6672 can be coupled to the outer shell 6670 by any suitable means. In some embodiments, for example, the inner core 6672 can be coupled to the central portion 6616 of the outer shell 6670 by, for example, a friction fit. In other embodiments, the inner core 6672 can be coupled to the outer shell 6670 by an adhesive. The inner core 6672 can have a length such that the inner core 6672 is disposed within the lumen 6658 along substantially the entire length of the outer shell 6670 or only a portion of the length of the outer shell 6670.

The proximal portion of the inner core 6672 includes an opening 6673 configured to receive a portion of an expansion device 7500 (also referred to as an insertion tool or a deployment tool), as shown in FIGS. 24-31. The expansion device 7500 is similar to the expansion device 1500 shown and described above (see e.g. FIGS. 11-16). The expansion device 7500 differs, however, from expansion device 1500 in that the expansion device 7500 includes spacer 7532 configured to cooperate with the inner core 6672 of the implant 6610. In such an arrangement, the threaded portion of rod 7570 of the expansion device 7500 removably engages to the internal threads 6676 of the inner core 6672 of the implant 6610, rather than coupling directly to the distal portion of the implant (as shown in FIGS. 15 and 16). Although the inner core 6672 is shown as being threadedly coupled to the expansion device 7500, the inner core 6672 can be removably coupled to the expansion device 7500 by any suitable means, such as a protrusion and detent arrangement.

Figure 29:
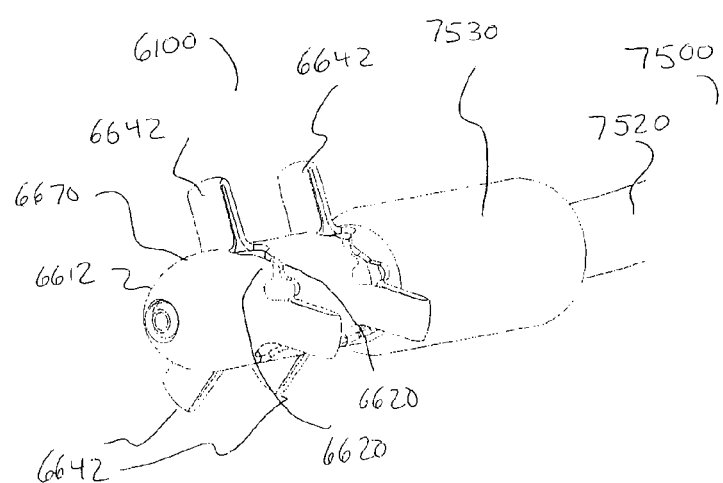
FIG. 29 is a perspective view of the implant and the expansion tool of FIG. 28 taken along region 29.
Figure 30:
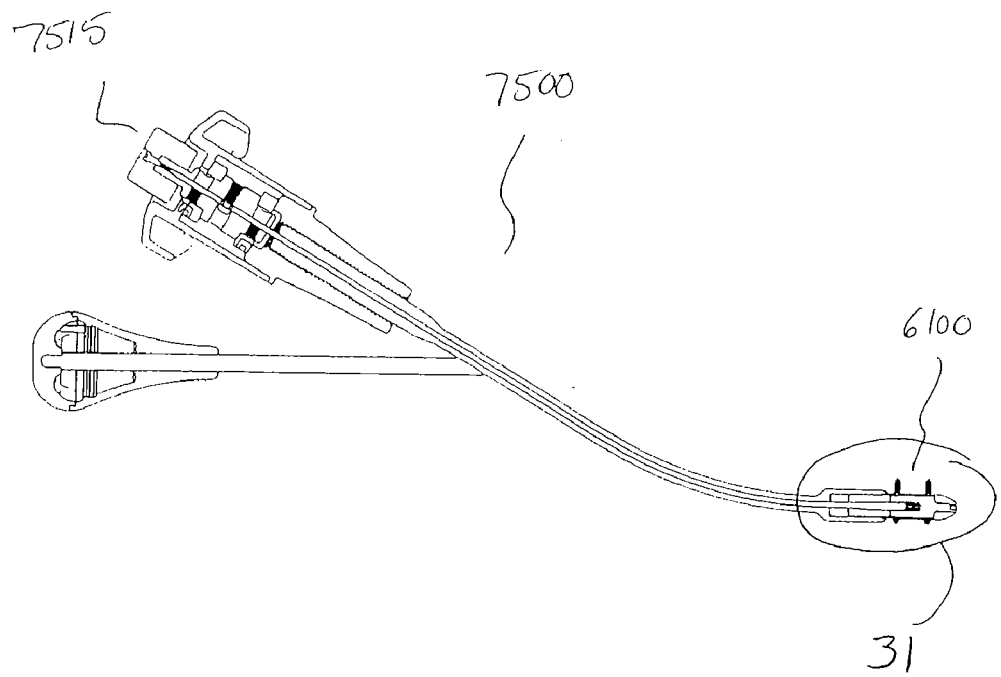
FIG. 30 is a side cross-sectional view of the implant and the expansion tool of FIG. 28.
Figure 31:
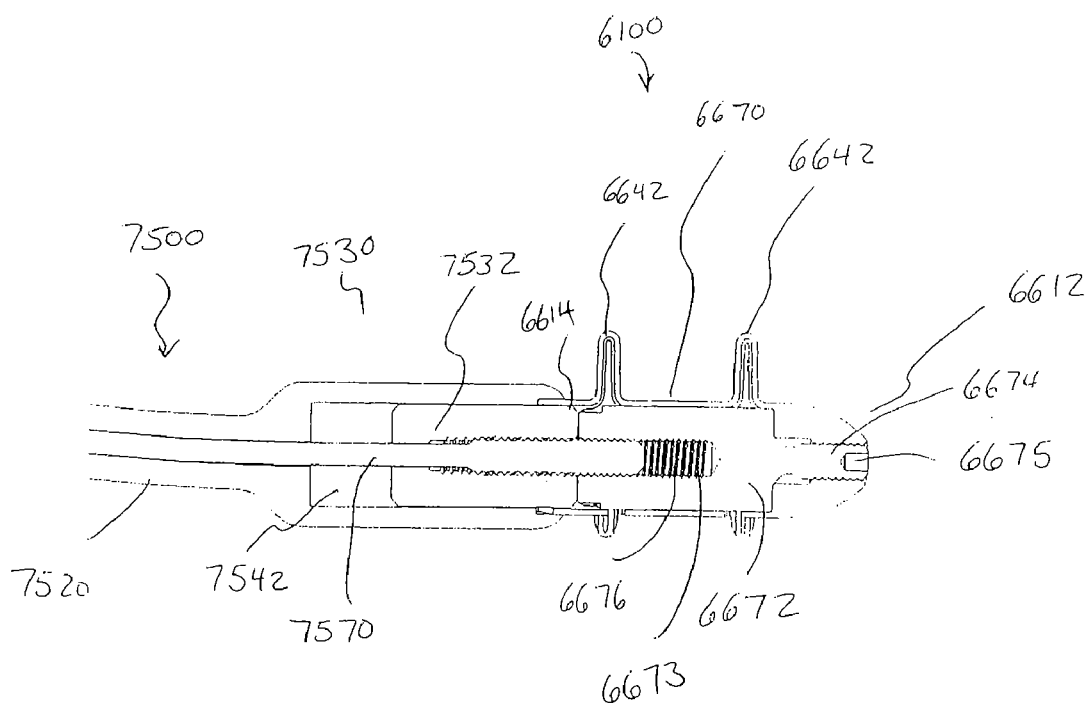
FIG. 31 is a side cross-sectional view of the implant and the expansion tool as shown in FIG. 30 taken along region 31.

In use, once the implant 6610 is positioned on the implant support portion 7530 of the expansion tool 7500 (see FIGS. 24 and 25), the implant is inserted into the patient's body and disposed between adjacent spinous processes. Once disposed between adjacent spinous processes, the expansion device can be used to move the inner core 6672 axially towards the proximal portion 6614 of the implant 6610 while simultaneously maintaining the position of the proximal portion 6614 of the implant 6610, as shown in FIGS. 29 and 31. In this manner, a compressive force is applied along the longitudinal axis of the outer shell 6670, thereby causing the outer shell 6670 to fold or bend to form extensions 6642 as described above. As illustrated, a portion of the spacer 7532 is received within the receiving area 7542 of the support portion 7530 as the implant 6610 is placed in the expanded configuration. Similarly, to move the implant 6610 from the expanded configuration to the collapsed configuration, the expansion device is actuated in the opposite direction to impart an axial force on the distal portion 6612 of the outer shell 6610 in a distal direction, moving the distal portion 6612 distally, and moving the implant 6610 to the collapsed configuration.

Once the implant 6610 is in its expanded configuration (see FIGS. 28-31), the implant 6610 can be disengaged from the expansion device 7500 by disengaging the distal portion of the rod 7570 from the opening 6673. The rod 7570 can be disengaged by actuating the knob assembly 7515 rotate the rod 7570 relative to the shaft 7520, as discussed above.

Although shown and described above without reference to any specific dimensions, in some embodiments, the outer shell 6670 can have a cylindrical shape having a length of approximately 34.5 mm (1.36 inches) and a diameter between 8.1 and 14.0 mm (0.32 and 0.55 inches). In some embodiments, the wall thickness of the outer shell can be approximately 5.1 mm (0.2 inches).

Similarly, in some embodiments, the inner core 6672 can have a cylindrical shape having an overall length of approximately 27.2 mm (1.11 inches) and a diameter between 8.1 and 14.0 mm (0.32 and 0.55 inches).

In some embodiments, the shape and size of the openings 6618 located adjacent the distal portion 6612 can be the same as that for the openings 6618 located adjacent the proximal portion 6614. In other embodiments, the openings 6618 can have different sizes and/or shapes. In some embodiments, the openings 6618 can have a length of approximately 11.4 mm (0.45 inches) and a width between 4.6 and 10 mm (0.18 and 0.40 inches).

Similarly, the shape and size of the tabs 6620 can be uniform or different as circumstances dictate. In some embodiments, for example, the longitudinal length of the tabs 6620 located adjacent the proximal portion 6614 can be shorter than the longitudinal length of the tabs 6620 located adjacent the distal portion 6612. In this manner, as the implant is moved from the collapsed configuration to the expanded configuration, the tabs adjacent the distal portion will engage each other first, thereby limiting the expansion of the expandable portions 6640 adjacent the distal portion 6612 to a greater degree than the expandable portions 6642 located adjacent the proximal portion 6614. In other embodiments, the longitudinal length of the tabs can be the same. In some embodiments, the longitudinal length of the tabs can be between 1.8 and 2.8 mm (0.07 and 0.11 inches). In some embodiments, the end portions of opposing tabs 6620 can have mating shapes, such as mating radii of curvature, such that the opposing tabs 6620 engage each other in a predefined manner.

Although illustrated as having a generally rectangular shape, the expandable portions 6640 and the resulting extensions 6642 can be of any suitable shape and size. In some embodiments, for example, the expandable portions can have a longitudinal length of approximately 11.4 mm (0.45 inches) and a width between 3.6 and 3.8 mm (0.14 and 0.15 inches). In other embodiments, size and/or shape of the expandable portions located adjacent the proximal portion 6614 can be different than the size and/or shape of the tabs 6620 located adjacent the distal portion 6612. Moreover, as described above, the expandable portions 6640 can be contoured to extend slightly radially from the outer shell 6670. In some embodiments, for example, the expandable portions can have a radius of curvature of approximately 12.7 mm (0.5 inches) along an axis normal to the longitudinal axis of the implant.

In some embodiments, the expandable portions 6640 and the outer shell 6670 are monolithically formed. In other embodiments, the expandable portions 6640 and the outer shell 6670 are formed from separate components having different material properties. For example, the expandable portions 6640 can be formed from a material having a greater amount of flexibility, while the outer shell 6670 can be formed from a more rigid material. In this manner, the expandable portions 6640 can be easily moved from the collapsed configuration to the expanded configuration, while the outer shell 6670 is sufficiently strong to resist undesirable deformation when in use.

In one embodiment, an apparatus includes a first body coupled to a second body. The first body and the second body collectively are configured to be releasably coupled to an implant device configured to be disposed between adjacent spinous processes. A first engaging portion is coupled to the first body, and a second engaging portion is coupled to the second body. The first engaging portion and/or the second engaging portion is configured to be received within a first opening defined by the implant device. The first body configured to be moved relative to the second body such that a distance between the first engaging portion and the second engaging portion is moved between a first distance and a second distance, and simultaneously a length of the implant device is moved between a first length and a second length.

In another embodiment, a kit includes an implant that is reconfigurable between an expanded configuration and a collapsed configuration while disposed between adjacent spinous processes. The implant has a longitudinal axis and defines an opening. A deployment tool is configured to be releasably coupled to the implant. The deployment tool includes an engaging portion configured to be removably received within the opening of the implant and extend in a transverse direction relative to the longitudinal axis when the deployment tool is coupled to the implant. The deployment tool is configured to move the implant between the collapsed configuration and the expanded configuration while the implant is disposed between the adjacent spinous processes.

Figure 32:
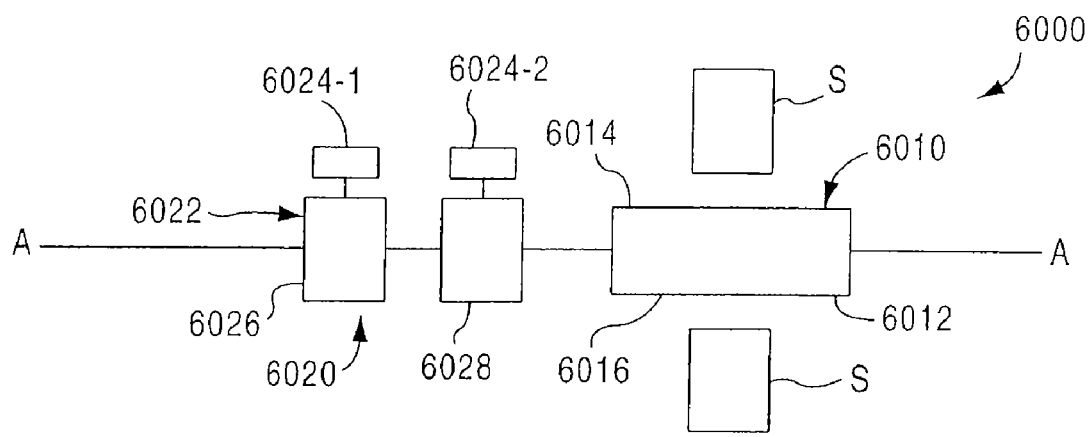
FIG. 32 is a schematic illustration of a medical device according to an embodiment of the invention in a collapsed configuration adjacent two spinous processes.
Figure 33:
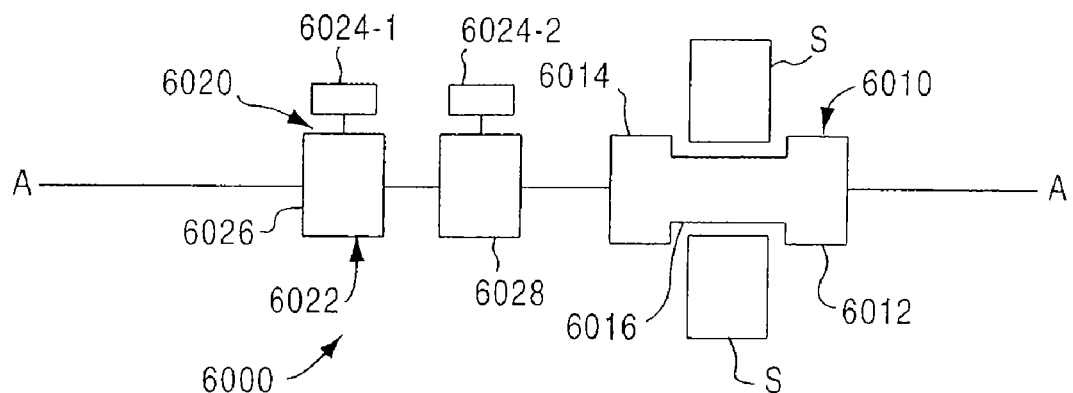
FIG. 33 is a schematic illustration of the medical device of FIG. 32 in an expanded configuration adjacent two spinous processes.

FIGS. 32 and 33 are schematic illustrations of a medical device according to an embodiment of the invention positioned between two adjacent spinous processes. FIG. 32 illustrates the medical device in a first configuration, and FIG. 33 illustrates the medical device in a second configuration. The medical device 6000 includes an implant 6010 and a deployment tool 6020. The implant 6010 includes a distal portion 6012, a proximal portion 6014, and a central portion 6016. The implant 6010 is configured to be inserted between adjacent spinous processes S. The central portion 6016 is configured to contact and provide a minimum spacing between the spinous processes S when adjacent spinous processes S move toward each other during their range of motion to prevent over-extension/compression of the spinous processes S. In some embodiments, the central portion 6016 does not substantially distract the adjacent spinous processes S. In other embodiments, the central portion 6016 does distract the adjacent spinous processes S. The implant 6010 and the deployment tool 6020 can each be inserted into a patient's back and moved in between adjacent spinous processes from the side of the spinous processes (i.e., a posterior-lateral approach). The use of a curved insertion shaft assists in the use of a lateral approach to the spinous processes S.

The implant 6010 has a collapsed configuration in which the proximal portion 6014, the distal portion 6012 and the central portion 6016 share a common longitudinal axis. In some embodiments, the proximal portion 6014, the distal portion 6012 and the central portion 6016 define a tube having a constant inner diameter. In other embodiments, the proximal portion 6014, the distal portion 6012 and the central portion 6016 define a tube having a constant outer diameter and/or inner diameter. In yet other embodiments, the proximal portion 6014, the distal portion 6012 and/or the central portion 6016 have different inner diameters and/or outer diameters.

The implant 6010 can be moved from the collapsed configuration to an expanded configuration, as illustrated in FIG. 33. In the expanded configuration, the proximal portion 6014 and the distal portion 6012 each have a larger outer perimeter (e.g., outer diameter) than when in the collapsed configuration, and the proximal portion 6014 and the distal portion 6012 each have a larger outer perimeter (e.g., outer diameter) than the central portion 6016. In the expanded configuration, the proximal portion 6014 and the distal portion 6012 are positioned to limit lateral movement of the implant 6010 with respect to the spinous processes S. The proximal portion 6014 and the distal portion 6012 are configured to engage the spinous process (i.e., either directly or through surrounding tissue and depending upon the relative position of the adjacent spinous processes S) in the expanded configuration. For purposes of clarity, the tissue surrounding the spinous processes S is not illustrated.

In some embodiments, the proximal portion 6014, the distal portion 6012 and the central portion 6016 are monolithically formed. In other embodiments, one or more of the proximal portion 6014, the distal portion 6012 and/or the central portion 6016 are separate components that can be coupled together to form the implant 6010. For example, the proximal portion 6014 and distal portion 6012 can be monolithically formed and the central portion 6016 can be a separate component that is coupled thereto. These various portions can be coupled, for example, by a friction fit, welding, adhesive, etc.

The implant 6010 is configured to be coupled to the deployment tool 6020. The deployment tool 6020 includes an elongate member 6022 and two or more engaging portions 6024. In the embodiment shown in FIGS. 32 and 33, there are two engaging portions 6024-1 and 6024-2 shown, but it should be understood that more than two engaging portions 6024 can be included. The elongate member 6022 can include a first body portion 6026 coupled to a second body portion 6028. In some embodiments, the first body portion 6026 is threadedly coupled to the second body portion 6028. The first body portion 6026 and the second body portion 6028 are configured to be moved relative to each other. For example, a threaded connection between the first body portion 6026 and the second body portion 6028 can be used to decrease or increase a distance between the first body portion 6026 and the second body portion 6028. The first body portion 6026 and the second body portion 6028 can be a variety of different shapes and sizes, and can be the same shape and/or size, or have a different shape and/or size than each other. For example, in some embodiments, the first body portion includes a straight distal end and a straight proximal end, and the second body portion includes a straight proximal end and a curved or rounded distal end. The curved distal end can assist with the insertion of the deployment tool into a lumen of an implant and also with the insertion of the medical device into a portion of a patient's body.

The first engaging portion 6024-1 can be coupled to the first body portion 6026 and the second engaging portion 6024-2 can be coupled to the second body portion 6028. The engaging portions 6024 can be, for example, substantially rectangular, square, circular, oval, semi-circular, or quarter-moon shaped. The engaging portions 6024, can be spring-loaded devices coupled to the elongate member 6022 of the deployment tool 6020, such that the engaging portions 6024 are biased into a position transverse to a longitudinal axis A defined by the elongate member 6022 and extending from an outer surface of the elongate member 6022. Upon force exerted on the engaging portions 6024, the engaging portions 6024 can be moved or collapsed to a position substantially below the outer surface of the elongate member 6022. The engaging portions 6024 can alternatively be coupled to an actuator (not shown) configured to move the engaging portions 6024 from a position transverse to the longitudinal axis A and extending from an outer surface of the elongate member 6022, to a position substantially below the outer surface of the elongate member 6022.

Figure 34:
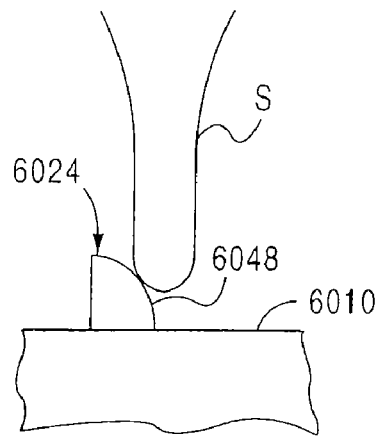
FIG. 34 is a side view of a portion of a medical device including an engaging portion in an extended configuration, according to an embodiment of the invention, positioned adjacent a spinous process.
Figure 35:
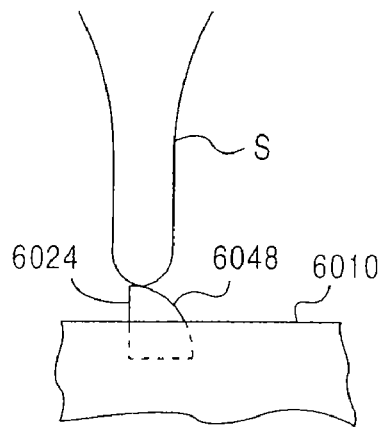
FIG. 35 is a side view of the portion of the medical device of FIG. 34 including the engaging portion in a partially collapsed configuration.
Figure 36:
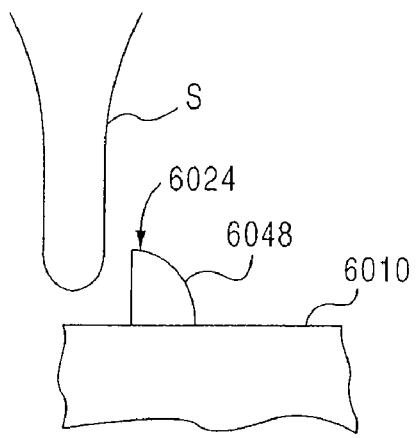
FIG. 36 is a side view of the portion of the medical device of FIG. 34 including the engaging portion in the extended configuration after being inserted past the spinous process.

FIGS. 34-36 illustrate the movement of an engaging portion 6024 as it passes by a spinous process S when an implant and deployment tool (collectively also referred to as medical device) are coupled together and being inserted between adjacent spinous processes. In some cases, as the medical device is being inserted, an engaging portion 6024 extending from a proximal portion of an implant may come into contact with a spinous process (or other tissue). To allow the engaging portion 6024 to pass by the spinous process, the engaging portion 6024 can be moved downward (as described above) so as to clear the spinous process. FIG. 34 illustrates an engaging portion 6024 having a spring-biased construction. The engaging portion 6024 includes a curved portion 6048 that initially contacts the spinous process S as the medical device is being inserted adjacent a spinous process S. As the curved portion 6048 contacts the spinous process S, the engaging portion 6024 is moved downward at least partially into an interior of the implant 6010, as shown in FIG. 35. The engaging portion 6024 moves back to an extended position (e.g., extending transversely from a surface of the implant 6010) after the engaging portion clears the spinous process S, as shown in FIG. 36, due to the bias of the spring (not shown).

Figure 37:
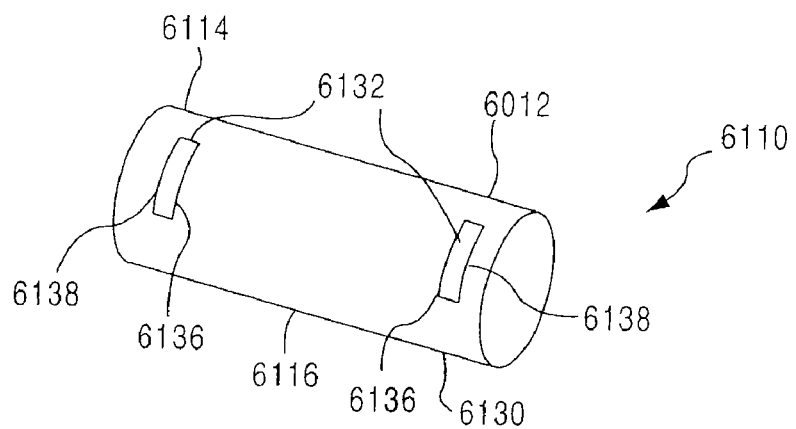
FIG. 37 is a side perspective view of an implant according to an embodiment of the invention in an expanded configuration.
Figure 47:
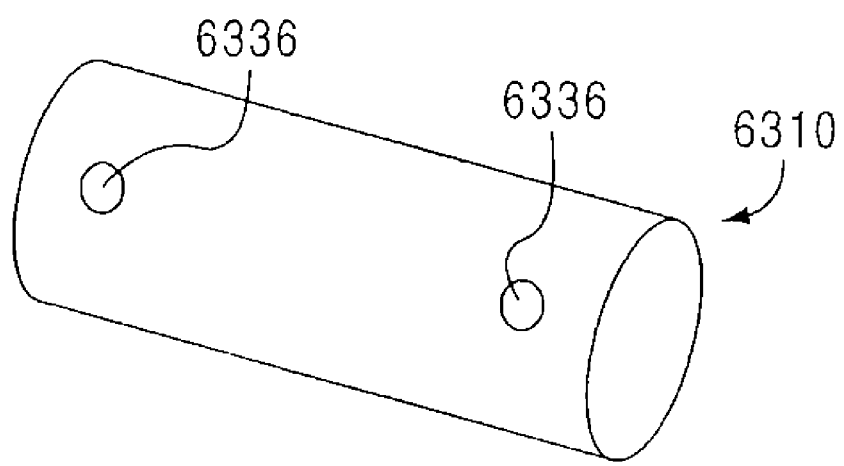
FIG. 47 is a side perspective view of an implant according to another embodiment of the invention.

The deployment tool 6020 can be used to move the implant 6010 from the collapsed configuration to the expanded configuration, and vice versa, as will be discussed in more detail below. The first body portion 6026 and the second body portion 6028 are collectively configured to be inserted at least partially into a lumen (not shown in FIGS. 32 and 33) of the implant 6010, such that at least one engaging portion 6024 extends through an opening (not shown in FIGS. 32 and 33) defined by the implant 6010. The implant 6010 can be configured with one or more such openings, each of which is configured to receive an engaging portion 6024 disposed on the elongate member 6022 (e.g., the first body portion 6026 or the second body portion 6028). The openings defined by the implant 6010 can be, for example, the openings can be circular, oval, square, rectangular, etc. FIG. 37 illustrates an example of an implant 6110 defining curved rectangular openings 6136, and FIG. 47 illustrates an implant 6310 defining curved round or circular openings 6336.

The openings are at least partially defined by an edge (not shown in FIGS. 32 and 33) on the implant 6010. The engaging portions 6024 on the deployment tool 6020 include a surface (not shown in FIGS. 32 and 33) that is configured to engage or contact the edge of the openings of the implant 6010 when the elongate member 6022 is inserted into the lumen of the implant 6010.

In use, the spinous processes S can be distracted prior to inserting the implant 6010. When the spinous processes are distracted, a trocar can be used to define an access passage for the implant 6010. In some embodiments, the trocar can be used to define the passage as well as distract the spinous processes S. Once an access passage is defined, the implant 6010 can be inserted percutaneously and advanced between the spinous processes, distal end 6012 first, until the central portion 6016 is located between the spinous processes S. In some embodiments, the implant 6010 can be coupled to the deployment tool 6020 prior to being inserted between the adjacent spinous processes. In other embodiments, the implant 6010 can be inserted between adjacent spinous processes without being coupled to the deployment tool 6020. In the latter configuration, after the implant 6010 is disposed between the adjacent spinous processes, the deployment tool 6020 can be inserted into the lumen defined by the implant 6010.

Once the implant 6010 is in place between the spinous processes, and the deployment tool 6020 is in position within the lumen of the implant 6010, the implant 6010 can be moved to the second configuration (i.e., the expanded configuration) by actuating the deployment tool 6020. For example, when the deployment tool 6020 is inserted into the lumen of the implant 6010, the first body portion 6026 is positioned at a first distance from the second body portion 6028, and the first engaging portion 6024-1 is positioned at a first distance from the second engaging portion 6024-2, as shown in FIG. 32. The deployment tool 6020 can then be actuated at a proximal end portion (e.g., by turning a handle) (not shown in FIGS. 32 and 33) causing the threaded coupling between the first body portion 6026 and the second body portion 6028 to move the first body portion 6026 and the second body portion 6028 towards each other such that the first body portion 6026 is now at a second distance (closer) from the second body portion 6028, as shown in FIG. 33. This movement likewise moves the first engaging portion 6024-1 and the second engaging portion 6024-2 to a closer position relative to each other. For example, in FIG. 32, the first engaging portion 6024-1 is positioned at a distance from the second engaging portion 6024-2 that is greater than a distance between the first engaging portion 6024-1 and the second engaging portion 6024-2 shown in FIG. 33.

As the engaging portions 6024-1 and 6024-2 are moved relative to each other, the surface (described above and described in more detail below) on the engaging portions 6024 imparts a force on the edge (described above and described in more detail below) of the opening defined by the implant causing the implant to move from the collapsed configuration to the expanded configuration.

The deployment tool 6020 is configured such that the deployment tool 6020 can be removed from the implant 6010 after the implant has been moved to the expanded configuration. The implant can remain disposed between the spinous processes indefinitely or removed as needed. For example, the deployment tool 6020 can be reinserted into the lumen of the implant 6010 and actuated in an opposite direction to cause the implant 6010 to be moved from the expanded configuration back to the collapsed configuration. In the collapsed configuration, the implant can be removed from the patient's body or repositioned to a new location between the spinous processes.

In some embodiments, the implant 6010 is inserted percutaneously (i.e., through an opening in the skin) and in a minimally-invasive manner. For example, as discussed in detail herein, the sizes of portions of the implant are expanded after the implant is inserted between the spinous processes. Once expanded, the sizes of the expanded portions of the implant are greater than the size of the opening. For example, the size of the opening/incision in the skin can be between 3 millimeters in length and 25 millimeters in length across the opening. In some embodiments, the size of the implant in the expanded configuration is between 3 and 25 millimeters across the opening.

Figure 38:
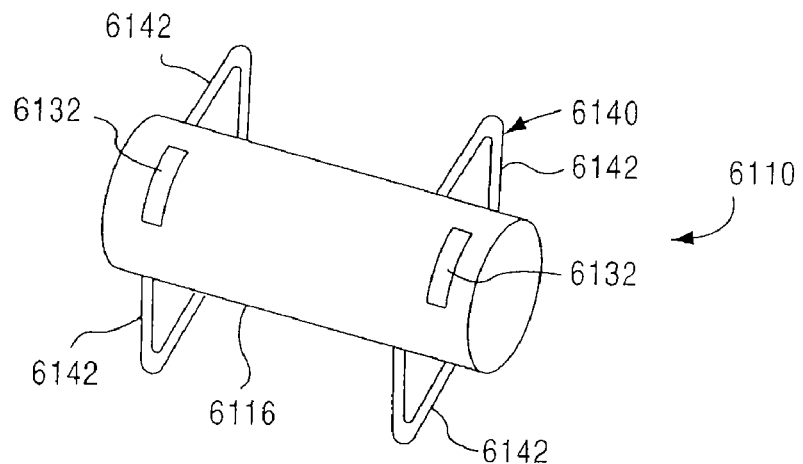
FIG. 38 is a side perspective view of the implant of FIG. 37 shown in a collapsed configuration.
Figure 39:
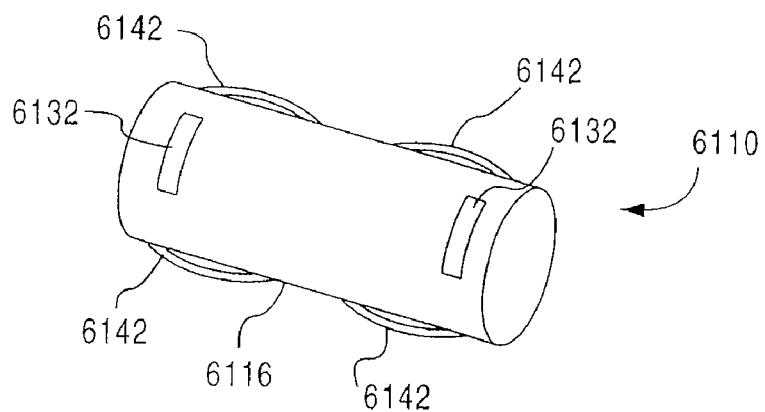
FIG. 39 is a side perspective view of the medical device of FIG. 37 shown in a collapsed configuration.
Figure 46:
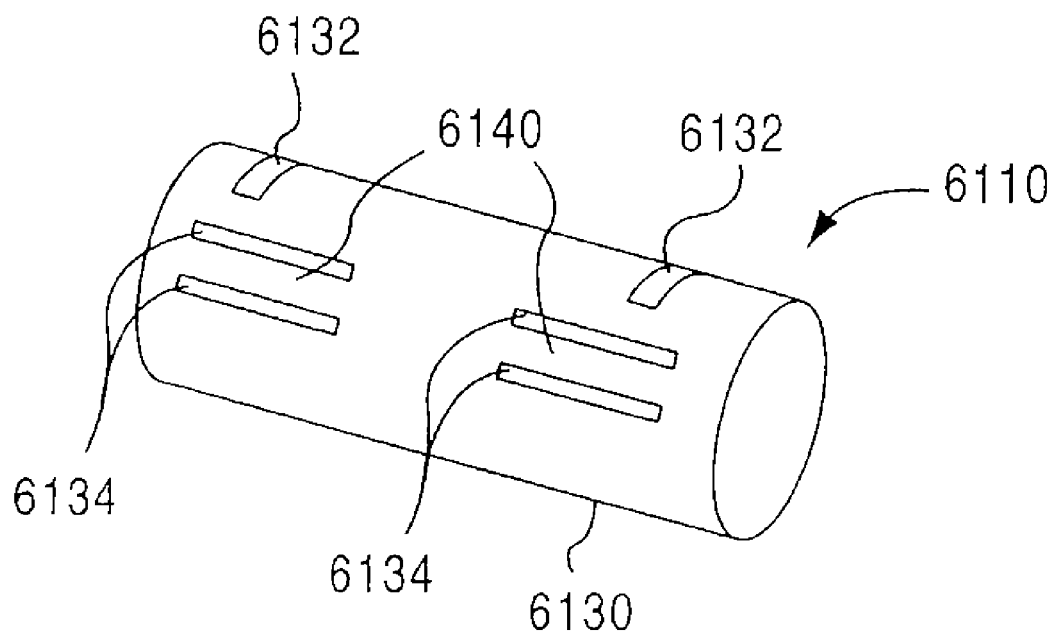
FIG. 46 is a side perspective view of the implant of FIG. 37 shown rotated about a longitudinal axis of the implant.

FIGS. 37-39 illustrate an implant according to an embodiment of the invention. An implant 6110 includes a proximal portion 6114, a distal portion 6112, and a central portion 6116. The implant 6110 also defines multiple openings 6132 on an outer surface of the implant 6110. The openings 6132 are in communication with a lumen 6158 (shown in FIG. 44) defined by the implant 6110. The openings 6132 are partially defined by a first edge 6136 and a second edge 6138. The implant 6110 includes expandable portions disposed at the distal portion 6112 and the proximal portion 6114. The expandable portions 6140 can be coupled to the implant 6110 or formed integral with the implant 6110, as shown in FIG. 46. As shown in FIG. 46, elongated slots 6134 can be defined on an outer surface of the implant 6110. The elongated slots 6134 create weakened areas on the implant 6110 that allow the expandable portions 6140 to fold when exposed to axial force, forming extensions 6142, as shown in FIG. 38.

The implant 6110 can be inserted between adjacent spinous processes (not shown) in a collapsed configuration, as shown in FIG. 37, and then moved to an expanded configuration, as shown in FIG. 38. The implant 6110 can then be moved back to a collapsed configuration as shown in FIG. 39, which illustrates the expandable portions 6140 in a partially collapsed configuration. Although FIG. 39 shows a partially collapsed configuration, in some embodiments, the implant can be moved back to the collapsed configuration as shown in FIG. 37.

Figure 40:
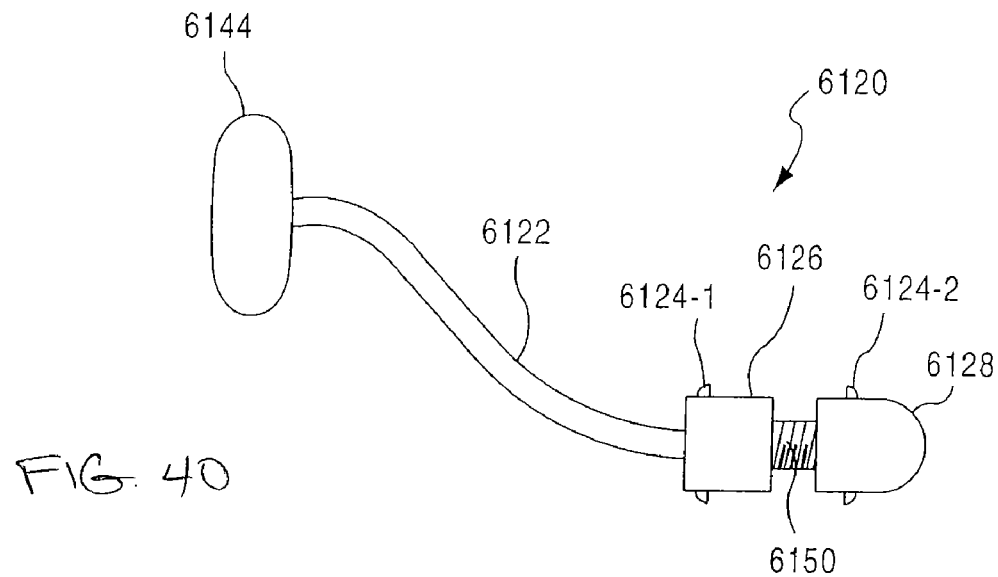
FIG. 40 is a side view of a deployment tool according to an embodiment of the invention.
Figure 41:
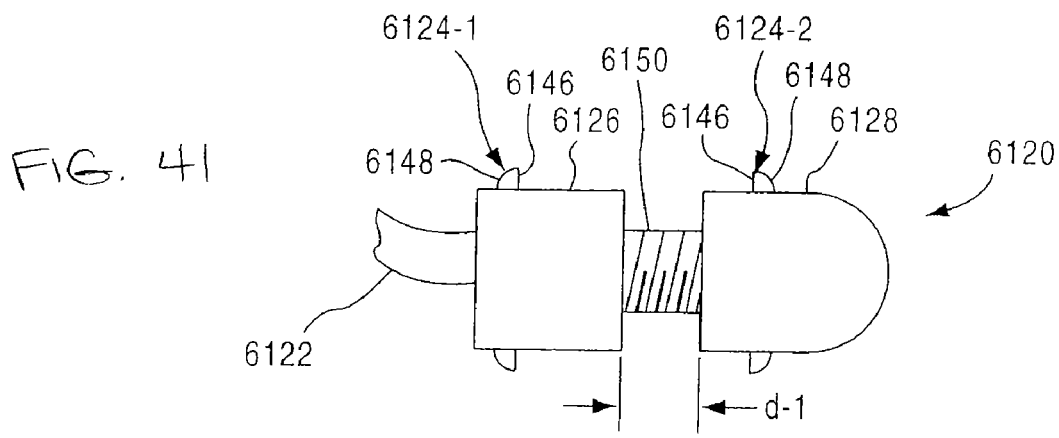
FIG. 41 is a side view of a portion of the deployment tool of FIG. 40 shown in a first configuration.
Figure 42:
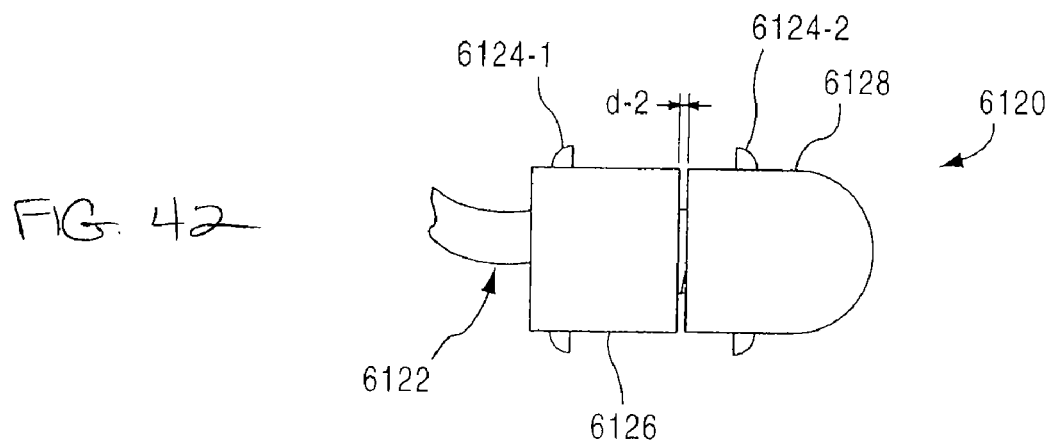
FIG. 42 is a side view of the portion of the deployment tool of FIG. 41 shown in a second configuration.

To move the implant 6110 from the collapsed configuration to the expanded configuration, and vice versa, a deployment tool, as described above and as shown in FIGS. 40-42, can be used. The deployment tool 6120 includes an elongate member 6122 coupled to a handle 6144. The elongate member 6122 includes a first body portion 6126 coupled to a second body portion 6128 through a threaded coupling 6150. A pair of engaging portions 6124-1 are disposed on the first body portion 6126, and a pair of engaging portions 6124-2 are disposed on the second body portion 6128. The engaging portions 6124-1 and 6124-2 (also collectively referred to as engaging portions 6124) include a surface 6146 and a rounded portion 6148. The threaded coupling 6150 between the first body portion 6126 and the second body portion 6128 is used to move the first body portion 6126 and the second body portion 6128 such that a distance between the first body portion 6126 and the second body portion 6128 is changed. For example, FIG. 41 illustrates a first distance d–1 between the first body portion 6126 and the second body portion 6128, and FIG. 42 illustrates a second distance d–2 between the first body portion 6126 and the second body portion 6128. As shown in FIGS. 41 and 42, as the distance between the first body portion 6126 and the second body portion 6128 is changed, a distance between the engaging portions 6124-2 and 6124-2 is also changed.

Figure 43:
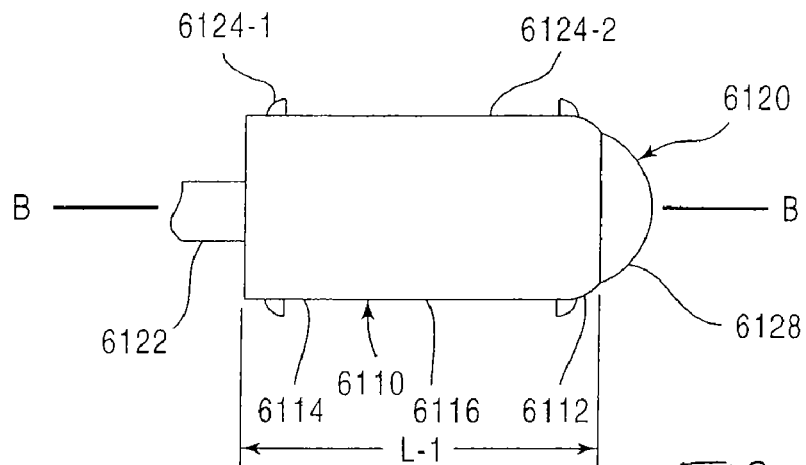
FIG. 43 is a side view of a portion of the deployment tool of FIG. 41 and the implant of FIG. 37 with the implant shown in an expanded configuration.
Figure 44:
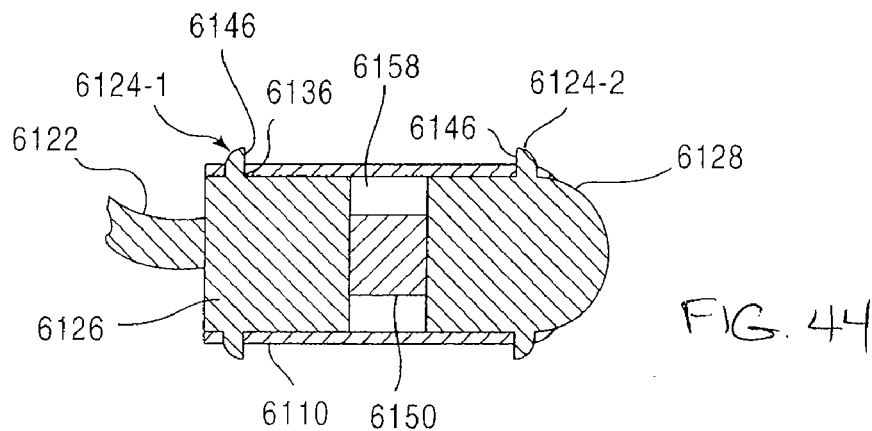
FIG. 44 is a cross-sectional view of the portion of the deployment tool and implant shown in FIG. 43.
Figure 45:
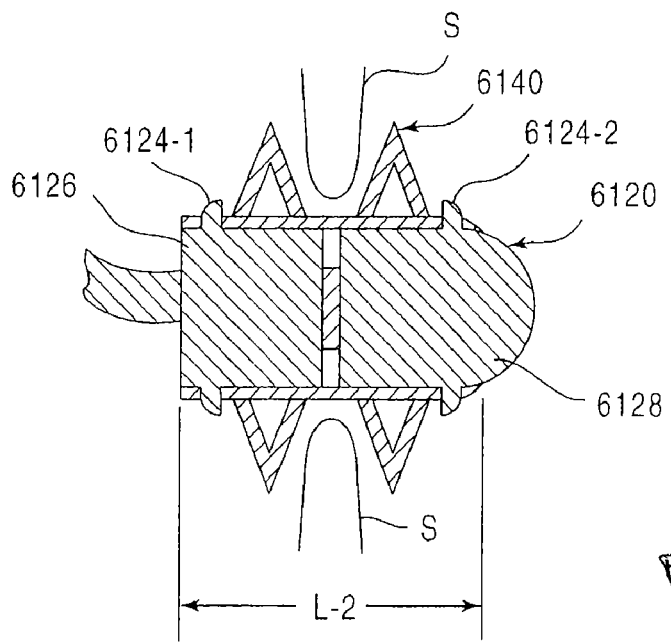
FIG. 45 is a cross-sectional view of the deployment tool and implant of FIG. 43 with the implant shown in a collapsed configuration positioned between adjacent spinous processes.

In use, the first body portion 6126 and the second body portion 6128 are collectively disposed within the lumen 6158 of the implant 6110, such that the engaging portions 6124 extend through the openings 6132 and transverse to an axis B defined by the implant 6110, as shown in FIGS. 43-45. In this position, the surface 6146 of the engaging portions 6124 is configured to contact the edge 6136 of the openings 6132. FIGS. 43 and 44 illustrate the first body portion 6126 and the second body portion 6128 disposed within the lumen of the implant 6110, when the implant is in a collapsed configuration. In this position, the first body portion 6126 is at a first distance from the second body portion 6128, the engaging portions 6124-1 are at a first distance from the engaging portions 6124-2, and the implant has a first length L–1.

When the implant is positioned between spinous processes S, the deployment tool 6120 can be actuated to move the implant 6110 to the expanded configuration, as shown in FIG. 45. When the deployment tool 6120 is actuated, the first body portion 6126 is moved closer to the second body portion 6128, and the engaging portions 6124-1 are moved closer to the engaging portions 6124-2. When this occurs, the surface 6146 on the engaging portions 6124 impart a force on the edge 6136 of the openings 6132, which axially compresses the implant 6110 until the implant 6110 has a second length L–2, as shown in FIG. 45.

Figure 51:
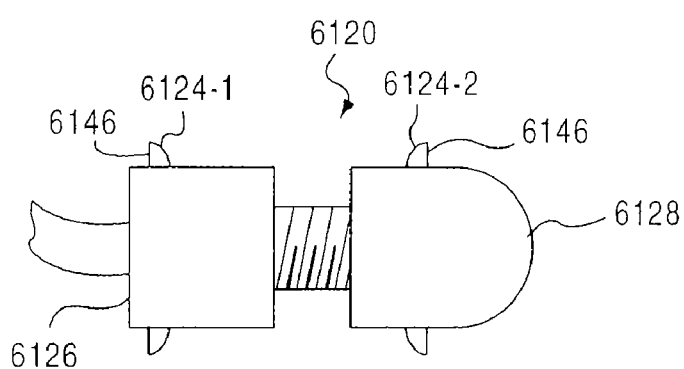
FIG. 51 is a side view of a deployment tool according to another embodiment of the invention.

To move the implant 6110 back to the collapsed configuration, the deployment tool 6120 can be reconfigured such that the surface 6146 of the engaging portions 6124 are positioned facing an opposite direction and configured to contact the edge 6138 of the implant 6110, as shown in FIG. 51. In some embodiments, the engaging portions 6124 can be, for example, removed and re-coupled to the elongate member 6122 (e.g., the first body portion 6126 and the second body portion 6128) such that the same engaging portions 6124 are simply repositioned. In other embodiments, a second deployment tool can be used having engaging portions positioned in the opposite direction. In either case, the deployment tool is inserted into the lumen 6158 of the implant 6110 as done previously, such that the engaging portions 6124 extend through the openings 6132 of the implant 6110 and the surface 6146 contacts the edge 6136 of the implant 6110. The deployment tool 6120 is then actuated in an opposite direction (e.g., turned in an opposite direction) such that the first body portion 6126 and the second body portion 6128 are threadedly moved further away from each other. In doing so, the engaging portions 6124-1 are moved further away from the engaging portions 6124-2, and the surface 6146 of the engaging portions 6124 impart a force on the edge 6138 (instead of edge of 6136) of openings 6132, which moves the implant 6110 back to the collapsed or straightened configuration. Thus, the implant described in all of the embodiments of the invention can be repeatedly moved between the collapsed and expanded configurations as necessary to insert, reposition or remove the implant as desired.

Figure 48:
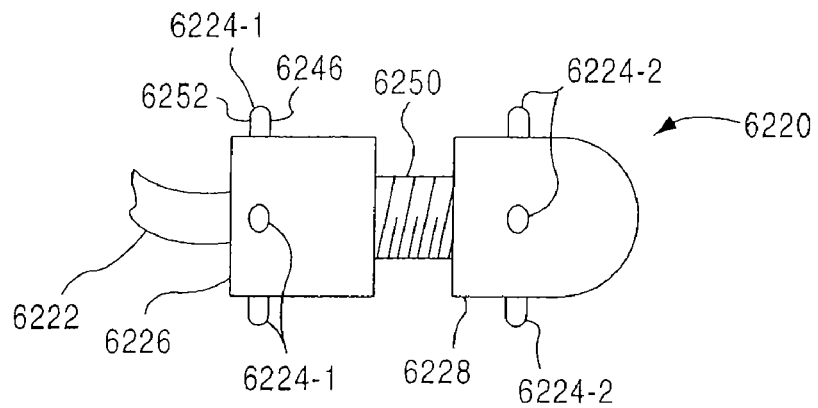
FIG. 48 is a side view of a deployment tool according to another embodiment of the invention.

FIG. 48 illustrates a deployment tool according to another embodiment of the invention. A deployment tool 6220 includes an elongate member 6222 having a first body portion 6226 coupled to a second body portion 6228 through a threaded coupling 6250. In this embodiment, the deployment tool 6220 includes two sets of four (8 total) engaging portions 6224 (only six engaging portions are shown in FIG. 48). A first set of engaging portions 6224-1 are coupled to the first body portion 6226, and a second set of engaging portions 6224-2 are coupled to the second body portion 6228. The engaging portions 6224 include a first surface 6246 and a second surface 6252. When the deployment tool 6220 is coupled to an implant, the first surface 6246 is configured to contact an edge of an opening defined on the implant (such as edge 6136 on implant 6110), and the second surface 6252 is configured to contact an opposite edge on the opening defined by the implant (such as edge 6138 on implant 6110).

Thus, in this embodiment, the deployment tool 6220 can be inserted into an implant and used to move the implant between a collapsed configuration and an expanded configuration without having to reposition the engaging portions 6224, or use a second deployment tool. To move the implant from a collapsed configuration to an expanded configuration, the deployment tool 6220 is actuated in a first direction. To move the implant back to the collapsed configuration, the deployment tool 6220 is actuated in an opposite direction (e.g., turned in an opposite direction). When the deployment tool 6220 is actuated to move the implant from the collapsed configuration to the expanded configuration, the surface 6246 of the engaging portions 6224 impart a force on an edge of an opening (e.g., edge 6136 on implant 6110), causing the implant to be axially compressed, as previously described. When the deployment tool 6220 is actuated to move the implant from the expanded configuration to the collapsed configuration, the surface 6252 of the engaging portions 6224 imparts a force on an opposite edge of the opening (e.g., edge 6138 on implant 6110), causing the implant to be substantially straightened as previously described.

Figure 49:
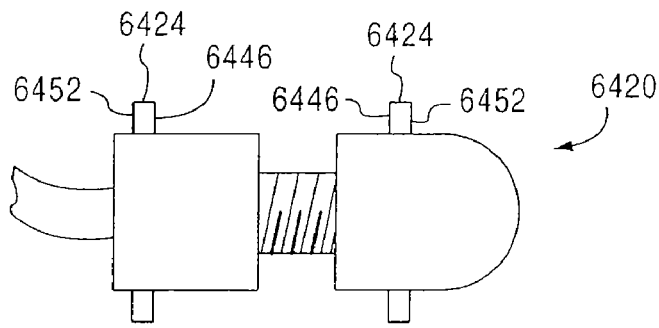
FIG. 49 is a side view of a deployment tool according to another embodiment of the invention.

FIG. 49 illustrates a deployment tool according to another embodiment of the invention. A deployment tool 6420 is similar to the deployment tool 6220 described above, except in this embodiment, there are only two sets of two engaging portions 6424 (4 total). The engaging portions 6424 are similar to the engaging portions 6224 except the engaging portions 6424 are substantially rectangular shaped. The engaging portions 6424 include a surface 6446 configured to contact an edge of an opening defined by an implant, and a surface 6452 configured to contact an opposite edge of the opening defined by the implant.

Figure 50:
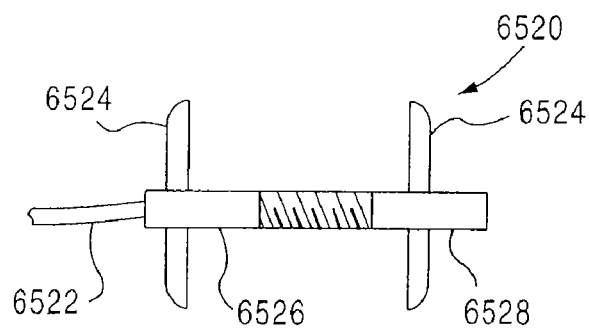
FIG. 50 is a side view of a deployment tool according to another embodiment of the invention.

FIG. 50 illustrates a deployment tool according to yet another embodiment of the invention. A deployment tool 6520 is similarly constructed and functions similarly to the previous embodiments. The deployment tool 6520 includes an elongate member 6522 that includes a first body portion 6526 and a second body portion 6528. In this embodiment, the first body portion 6526 and the second body portion 6528 are smaller than illustrated in the previous embodiments, and engaging portions 6524 are coupled to the first body portion 6526 and the second body portion 6528 that are more elongate than previously shown.

Figure 52:
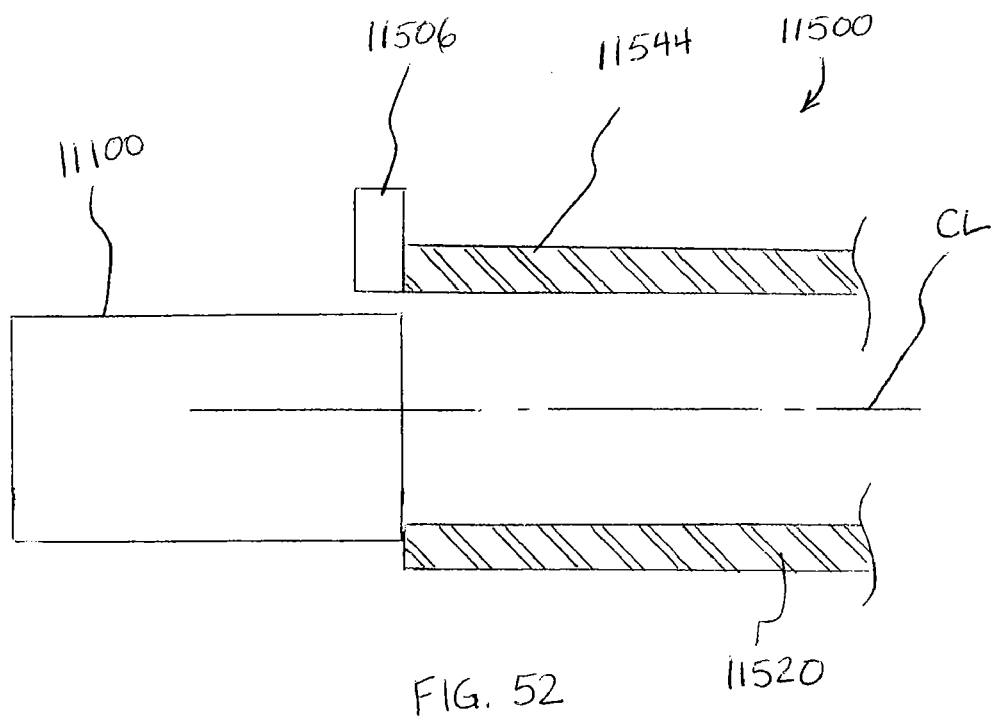
FIGS. 52 and 53 are schematic illustrations of a deployment tool according to an embodiment of the invention, in a first configuration and a second configuration, respectively.
Figure 53:
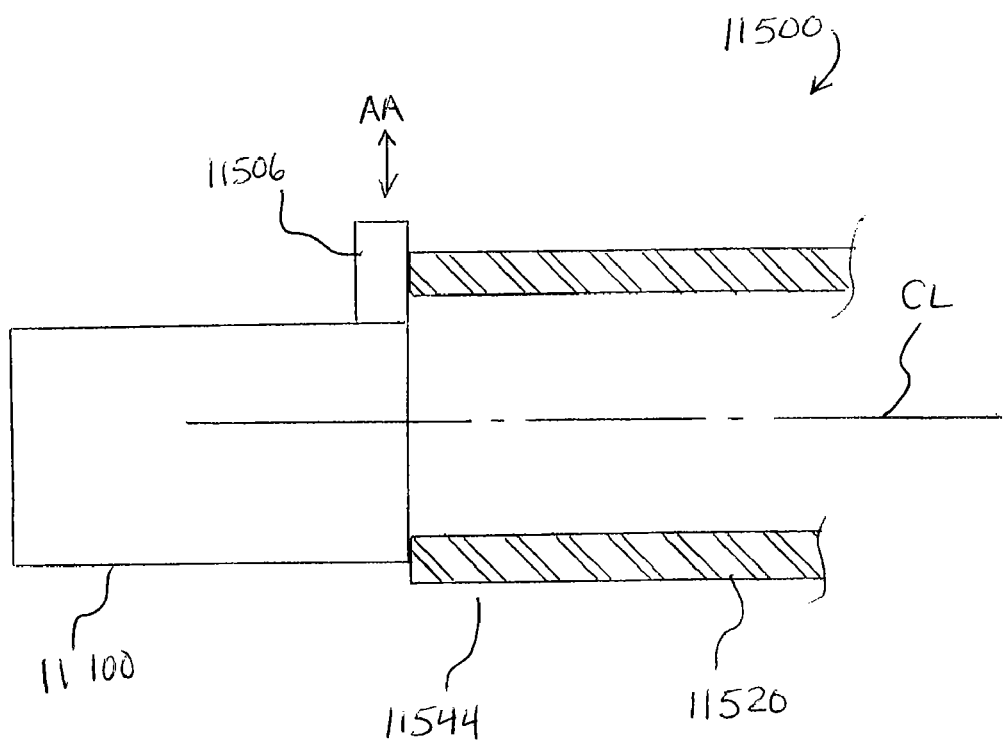

FIGS. 52 and 53 are schematic illustrations of a deployment tool 11500 according to an embodiment of the invention in a first configuration and a second configuration, respectively. The deployment tool 11500 includes an elongate member 11520 and a locking member 11506. The elongate member 11520 has a distal end portion 11544 and defines a center line CL. The elongate member 11520, which can be, for example, a shaft of any type shown and described above, is configured to engage a spinal implant 11100. The locking member 11506 is disposed at the distal end portion 11544 of the elongate member 11520 and can be moved relative to the elongate member 11520 between a first position (FIG. 52) and second position (FIG. 53) in a direction substantially perpendicular to the center line CL, as shown by arrow AA in FIG. 53. Said another way, the locking member 11506 can translate relative to the elongate member 11520 between the first position and the second position in a direction substantially perpendicular to the center line CL.

When the locking member 11506 is in the first position, the distal end portion 11544 of the elongate member 11520 can move relative to the spinal implant 11100. When the locking member 11506 is in the second position, the distal end portion 11544 of the elongate member 11520 is coupled to the spinal implant 11100. In this manner, the deployment tool 11500 can maintain a position of the spinal implant 11100 such that the spinal implant 11100 can be inserted, removed and/or repositioned within the body. In some embodiments, for example, the deployment tool 11500 can prevent the spinal implant 11100 from rotating relative to the elongate member 11520 when the locking member 11506 is in the second position. In some embodiments, the deployment tool 11500 can prevent the spinal implant 11100 from translating (e.g., moving distally and/or proximally) relative to the elongate member 11520 when the locking member 11506 is in the second position.

Figure 56:
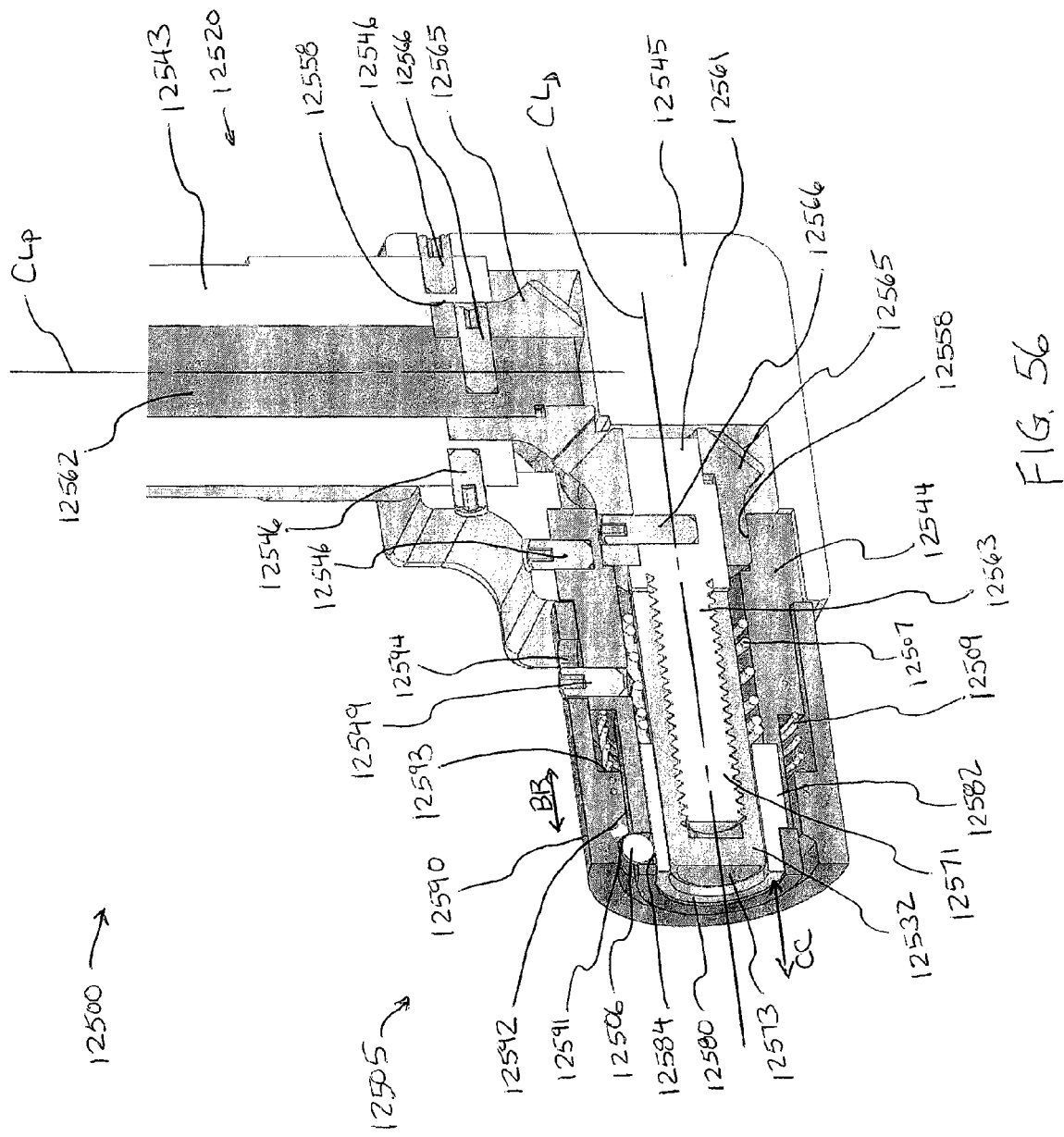
FIG. 56 is a perspective cross-sectional view of a portion of the deployment tool shown in FIG. 54.

FIG. 54 shows a deployment tool 12500 according to an embodiment of the invention. The deployment tool 12500 includes an outer shaft assembly 12520 having a proximal shaft 12543 and a distal shaft 12544 joined together by a coupling 12545. The proximal shaft 12543 defines a center line $CL_P$ that is substantially normal to a center line $CL_D$ defined by the distal shaft 12544, as shown in FIG. 56. A knob 12515 is disposed at the proximal end portion 12543 of the outer shaft assembly 12520. A connector 12505 is disposed at the distal end portion 12544 of the outer shaft assembly 12520. As described in more detail herein, the connector 12505 is configured to removably connect the distal end portion 12544 of the outer shaft assembly 12520 to a spinal implant 6610' such that the spinal implant 6610' can be manipulated during insertion into, removal from and/or repositioning within the body.

As shown in FIG. 55, the spinal implant 6610', which is similar to the spinal implant 6610 shown and described above with reference to FIGS. 17-23, includes an outer shell 6670' having a distal portion 6612' and a proximal portion 6614'. As described above, the outer shell 6670' defines a series of openings and has a series of expandable portions that form extensions 6642' that extend outwardly from the outer shell 6670' when the implant 6610' is in the expanded configuration. The proximal end portion 6614' of the outer shell 6670' defines three notches 6606' that can be used, for example, to align the implant with the deployment tool 12500, as described above. The outer shell 6670' of the spinal implant 6610' also defines a series of openings 6607' that can be used to couple the proximal end portion 6614' of the spinal implant 6610' to the deployment tool 12500, as described herein.

The spinal implant 6610' also includes an inner core 6672' disposed within the outer shell 6670'. As described above, the inner core 6672' is configured to maintain the shape of the implant 6610' during insertion, to prevent the expandable portions from extending inwardly into a region inside of the outer shell 6670' during deployment and/or to maintain the shape of the central portion 6616' once the implant is in its desired position. The proximal portion of the inner core 6672' defines an opening 6673' configured to receive a portion of an expansion device (also referred to as an insertion tool or a deployment tool), such as expansion device 7500 shown and described above with reference to FIGS. 24-31.

As shown in FIG. 56, the connector 12505 includes three locking members 12506 (only one shown in FIG. 56), such as for example spherical members, an outer sleeve 12590 and an inner sleeve 12580. The locking members 12506 are disposed within openings 12547 defined by the distal shaft 12544 of the outer shaft assembly 12520 (see FIG. 57). As described herein, the locking members 12506 are configured to move within the opening 12547 in a direction substantially perpendicular to the center line $CL_D$ of the distal shaft 12544 of the outer shaft assembly 12520 such that the deployment tool 12500 can be removably coupled to the spinal implant 6110'. Said another way, the locking members 12506 are configured to translate relative to the distal shaft 12544 in a direction substantially perpendicular to the center line $CL_D$ of the distal shaft 12544 of the outer shaft assembly 12520.

Figure 61:
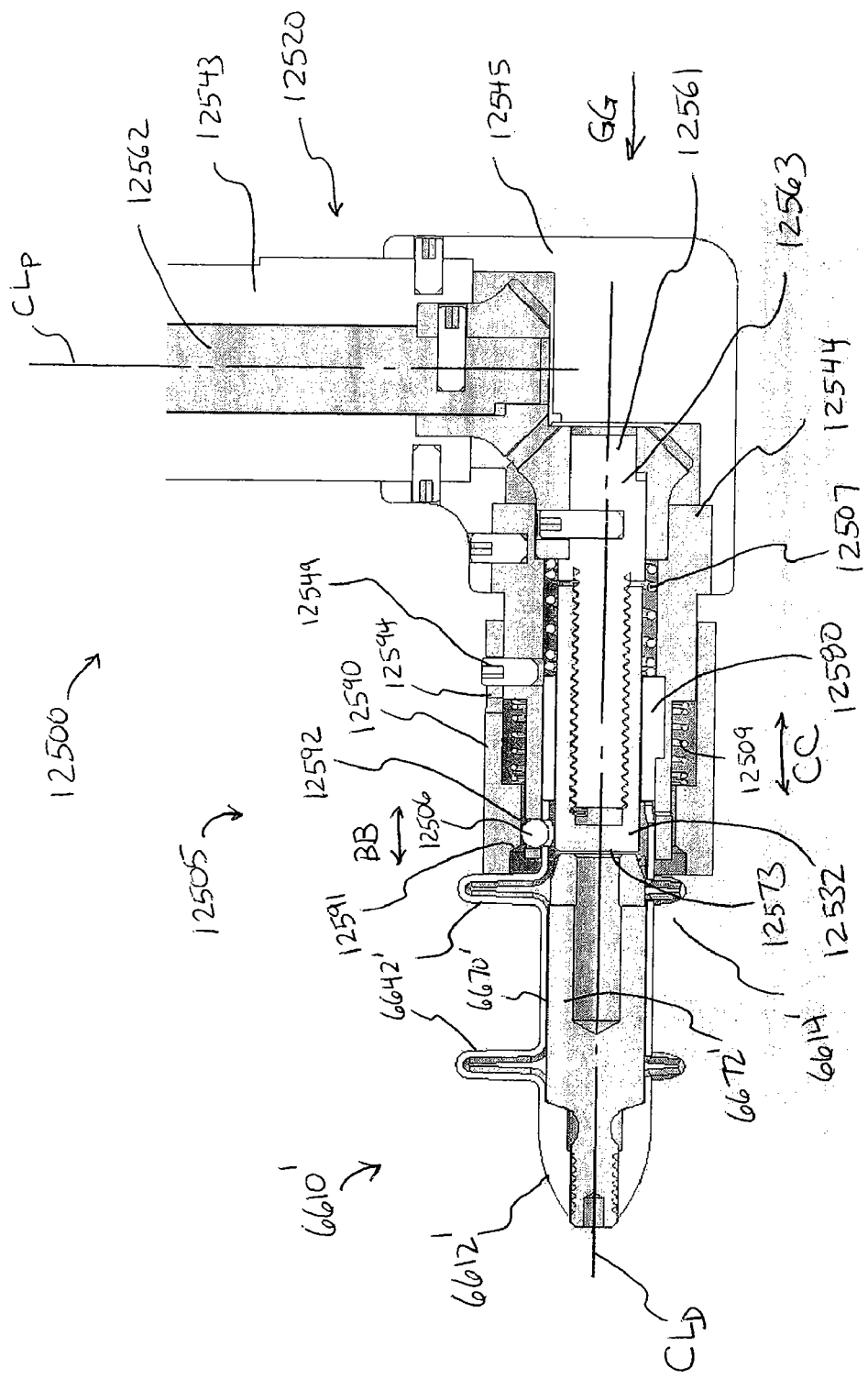
FIG. 61 is a front cross-sectional view of a portion of the deployment tool shown in FIG. 54 in a first configuration.

The outer sleeve 12590 is slidably disposed about the distal shaft 12544 of the outer shaft assembly 12520. The outer sleeve 12590 includes an actuation surface 12591 and a retention surface 12592. The actuation surface 12591 and/or the retention surface 12592 can be a curved surface (e.g., the surface of a cylinder or cone) or a planar surface. As shown in FIGS. 56 and 61, the actuation surface 12591 is at an acute angle with respect to the center line $CL_D$. The retention surface 12592 is substantially parallel to the center line $CL_D$. The outer sleeve 12590 has an extended position (see FIGS. 61 and 62) and a retracted position (see FIG. 56). When the outer sleeve 12590 is in the extended position, the retention surface 12592 engages the locking members 12506 to prevent the locking members 12506 from moving out from the openings 12547. In this manner, the retention surface 12592 of the outer sleeve 12590 retains the locking members 12506 within the openings 6607' of the spinal implant 6610'.

As shown in FIG. 56, when the outer sleeve 12590 is in the retracted configuration, the actuation surface 12591 engages the locking members 12506. When the outer sleeve 12590 moves from the retracted position to the extended position, as indicated by the arrow BB in FIGS. 56 and 61, the force moving the outer sleeve 12590 is transmitted via the actuation surface 12591 to the locking members 12506. Because the actuation surface 12591 is at an acute angle with respect to the center line $CL_D$ (e.g., the direction of motion of the outer sleeve 12590), a component of the force transmitted via the actuation surface 12591 to the locking members 12506 has an inward direction that is substantially normal to the center line $CL_D$. In this manner, outer sleeve 12590 actuates the locking members 12506 inwardly in a direction that is substantially normal to the center line $CL_D$ when the outer sleeve 12590 is moved from its retracted position to its extended position.

Figure 58:
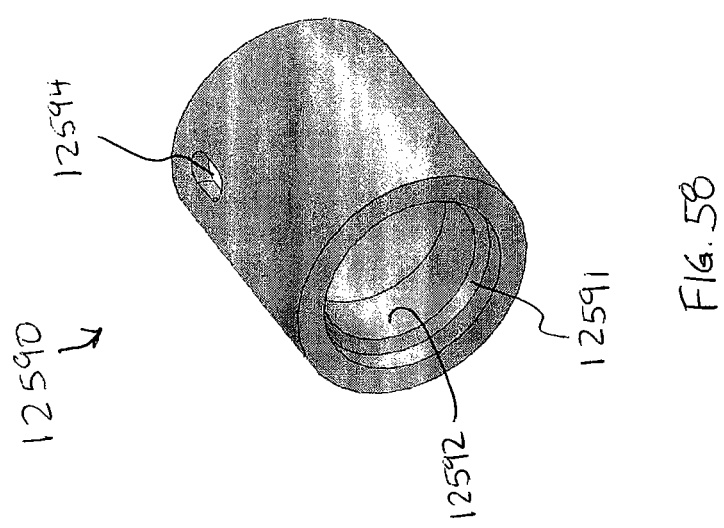
FIG. 58 is a perspective view of a portion of the deployment tool shown in FIG. 54.
Figure 62:
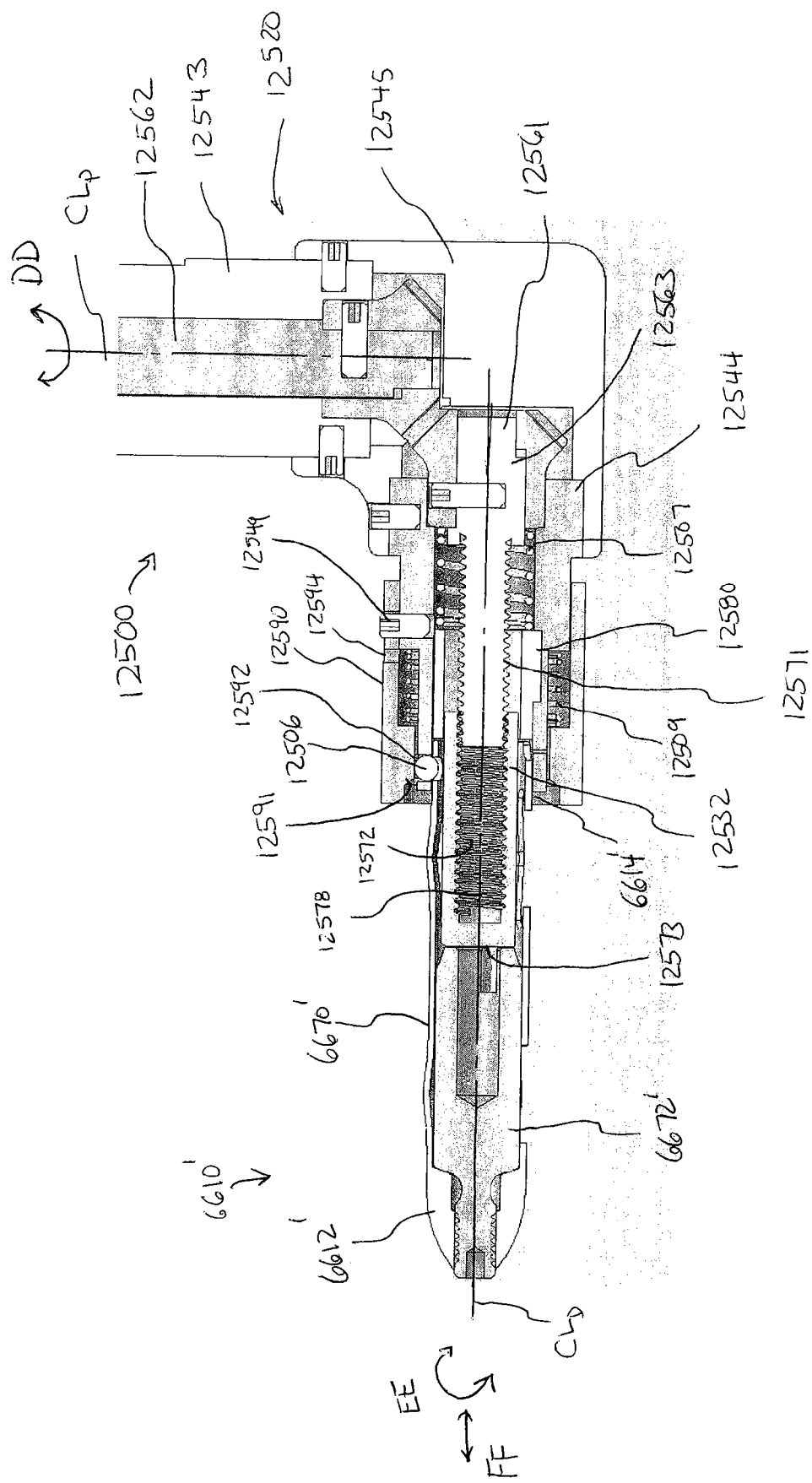
FIG. 62 is a front cross-sectional view of a portion of the deployment tool shown in FIG. 54 in a second configuration.

The outer sleeve 12590 is coupled to the outer shaft assembly 12520 by a pin 12549 that extends from the distal shaft 12544 of the outer shaft assembly 12520. A portion of the pin 12549 is received within an elongated opening 12594 (see FIG. 58) defined by the outer sleeve 12590. In use, a portion of the pin 12549 engages the ends of the elongated opening 12594 to limit the distance through which the outer sleeve 12590 can move with respect to the distal shaft 12544 of the outer shaft assembly 12520 when moving between the extended position and the retracted position. Said another way, when the outer sleeve 12590 is in the retracted position, as shown in FIG. 56, the pin 12549 is in contact with a distal end of the elongated opening 12594. Similarly, when the outer sleeve is in the extended position, as shown in FIGS. 61 and 62, the pin 12549 is in contact with a proximal end of the elongated opening 12594. Accordingly, the distance through which the outer sleeve 12590 can move with respect to the outer shaft assembly 12520 is approximately the length of the elongated opening 12594 along a direction parallel to the center line $CL_D$.

Figure 57:
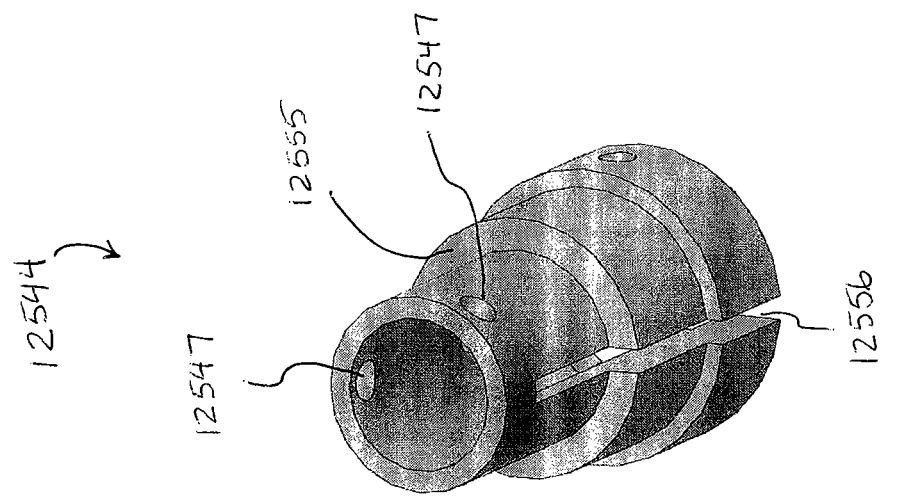
FIG. 57 is a perspective view of a portion of the deployment tool shown in FIG. 54.
Figure 59:
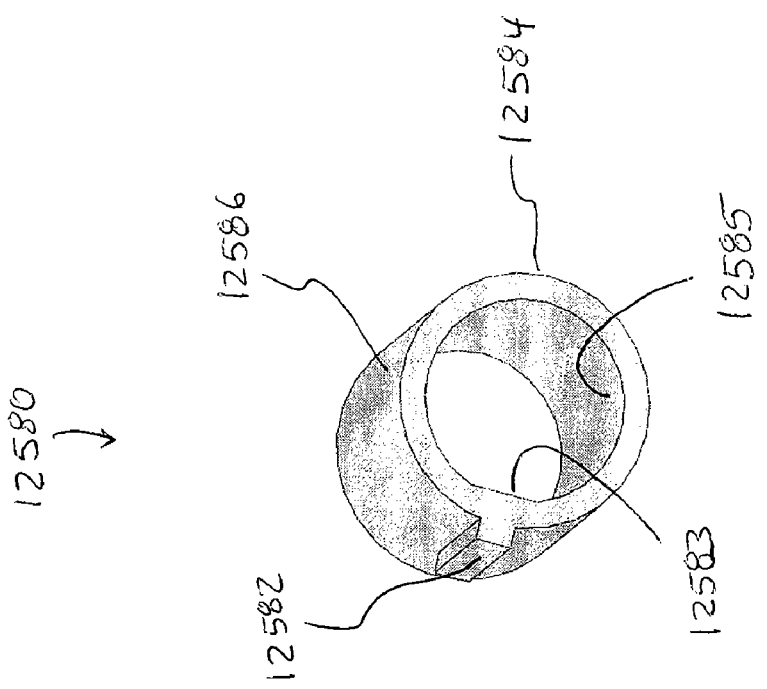
FIG. 59 is a perspective view of a portion of the deployment tool shown in FIG. 54.

As described herein, the inner sleeve 12580 cooperates with the outer sleeve 12590 to actuate and/or retain the locking members 12506 to removably couple the deployment tool 12500 to the spinal implant 6110'. The inner sleeve 12580 is slidably disposed within the distal shaft 12544 of the outer shaft assembly 12520. As shown in FIG. 59, the inner sleeve 12580 includes an outer surface 12586 and an inner surface 12585. The inner surface 12585 of the inner sleeve 12580 includes a flatted surface 12583 and defines an opening within which a drive member 12532 is disposed. Alternatively, the drive member 12532 can be monolithically formed with the remaining portions of the inner sleeve 12580. The outer surface 12586 of the inner sleeve 12580 defines a protrusion 12582 and a retention surface 12584. As shown in FIGS. 56 and 57, the protrusion 12582 is received within a slot 12556 defined by the distal shaft 12544 of the outer shaft assembly 12520 to prevent the inner sleeve 12580 from rotating relative to the distal shaft 12544 of the outer shaft assembly 12520 while allowing the inner sleeve 12580 to move in a direction parallel to the center line $CL_D$.

The inner sleeve 12580 has an extended position (see FIG. 56) and a retracted position (see FIGS. 61 and 62). When the inner sleeve 12580 is in the extended position, the retention surface 12584 engages the locking members 12506 to prevent the locking members 12506 from moving into the openings 12547. In this manner, the retention surface 12584 of the inner sleeve 12580 maintains the position of the locking members 12506 outwardly against the retention surface 12592 of the outer sleeve 12590, thereby preventing the outer sleeve 12590 from moving from its retracted position (FIG. 56) to its extended position (FIGS. 61 and 62). Said another way, when the inner sleeve 12580 is in its extended position, the outer sleeve 12590 is in its retracted position. Similarly, when the inner sleeve 12580 is in its retracted position, the outer sleeve 12590 can be in its extended position.

As shown in FIGS. 61 and 62, when the inner sleeve 12580 moves from its extended position to its retracted position as indicated by the arrow CC in FIGS. 56 and 61, the locking members 12506 are disengaged from the retention surface 12584 of the inner sleeve 12580. Accordingly, when the inner sleeve 12580 is in its retracted position the locking members 12506 can move inwardly in a direction that is towards and substantially normal to the center line $CL_D$ within the openings 6607' of the spinal implant 6610'.

The outer sleeve 12590 is biased towards its extended position by a spring 12509 disposed between a shoulder surface 12555 of the distal shaft 12544 of the outer shaft assembly 12520 (see FIG. 57) and the spring engagement surface 12593 of the outer sleeve 12590 (see FIG. 56). Similarly, the inner sleeve 12580 is biased towards its extended position by a spring 12507 disposed between a surface of a miter gear 12565 (shown in FIG. 56) disposed within the outer shaft assembly 12520 and the end of the inner sleeve 12580.

The deployment tool 12500 includes an inner shaft assembly 12561 having a proximal shaft 12562 and a distal shaft 12563. The proximal shaft 12562 of the inner shaft assembly 12561 is movably disposed within the proximal shaft 12543 of the outer shaft assembly 12520 such that the proximal shaft 12562 of the inner shaft assembly 12561 is concentric with the center line $CL_P$. Similarly, the distal shaft 12563 of the inner shaft assembly 12561 is movably disposed within the distal shaft 12544 of the outer shaft assembly 12520 such that the distal shaft 12563 of the inner shaft assembly 12561 is concentric with the center line $CL_D$.

The knob 12515 is coupled to the proximal shaft 12562 of the inner shaft assembly 12561 such that the proximal shaft 12562 of the inner shaft assembly 12561 rotates about the center line $CL_P$ as shown by the arrow DD in FIG. 62 when the knob 12515 is rotated. The proximal shaft 12562 of the inner shaft assembly 12561 is operatively coupled to the distal shaft 12563 of the inner shaft assembly 12561 by two miter gears 12565. The miter gears 12565 are coupled to the proximal shaft 12562 of the inner shaft assembly 12561 and the distal shaft 12563 of the inner shaft assembly 12561 by fasteners 12566. The miter gears 12565 are configured to rotate with the outer shaft assembly 12520 and are supported by bearing surfaces 12558 defined by the outer shaft assembly 12520. In this manner, when the proximal shaft 12562 of the inner shaft assembly 12561 rotates about the center line $CL_P$, the distal shaft 12563 of the inner shaft assembly 12561 rotates about the center line $CL_D$, as shown by the arrow EE in FIG. 62.

Figure 60:
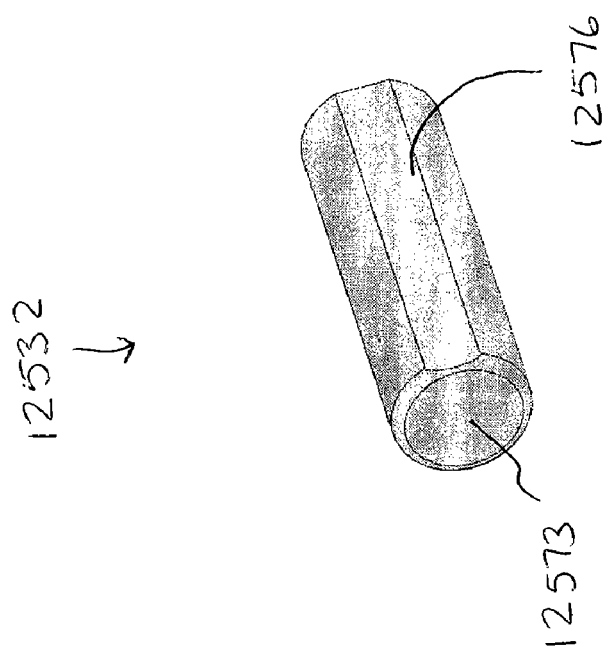
FIG. 60 is a perspective view of a portion of the deployment tool shown in FIG. 54.

A drive member 12532 is coupled to the distal shaft 12563 of the inner shaft assembly 12561 such that a portion of the drive member 12532 is movably disposed within at least a portion of the inner sleeve 12580. As shown in FIGS. 60 and 62, the drive member 12532 includes an end surface 12573, an outer surface 12577 and an inner surface 12578. The outer surface 12577 includes a flatted surface 12576 that corresponds to a flatted surface 12583 defined by the inner sleeve 12580. The inner surface 12578 includes a threaded portion 12572 configured to engage the threaded portion 12571 of the distal shaft 12563 of the inner shaft assembly 12561. In this manner, when the distal shaft 12563 of the inner shaft assembly 12561 rotates as shown by the arrow EE in FIG. 62, the drive member 12532 moves within the outer shaft assembly 12520 as shown by the arrow FF in FIG. 62. Moreover, the corresponding flatted surfaces 12583, 12576 prevent the drive member 12532 from rotating within the inner sleeve 12580 and/or the outer shaft assembly 12520.

In some embodiments, the deployment tool 12500 can be used to move the spinal implant 6610' from an expanded configuration (FIG. 61) to a collapsed configuration (FIG. 62) to facilitate removal and/or repositioning of the spinal implant 6610'. First, the distal shaft 12544 of the outer shaft assembly 12520 is inserted into the body of a patient and coupled to the outer shell 6670' of the spinal implant 6610' via the connector 12505. More particularly, the distal shaft 12544 of the outer shaft assembly 12520 is brought into engagement with the proximal end portion 6614' of the spinal implant 6610' by moving the distal shaft 12544 relative to the spinal implant 6610' as shown by the arrow GG in FIG. 61. When the distal shaft 12544 of the outer shaft assembly 12520 engages the proximal end portion 6614' of the spinal implant 6610', continued movement in the direction indicated by arrow GG causes the inner sleeve 12580 to move from its extended position (FIG. 56) to its retracted position (FIG. 61) along the direction of arrow CC in FIG. 61.

When the proximal end portion 6614' of the spinal implant 6610' is received within the distal shaft 12544 of the outer shaft assembly 12520, the openings 6607' are aligned with the locking members 12506. Accordingly, because the locking members 12506 are no longer held in place by the retention surface 12584 of the inner sleeve 12580 and/or the outer shell 6670' of the spinal implant 6610', the locking members 12506 are moved inwardly (i.e., towards the center line $CL_D$) by the actuation surface 12591 of the outer sleeve 12590 in a direction substantially perpendicular to the center line $CL_D$. In this manner, the locking members 12506 are moved inwardly to engage the openings 6607' (e.g., the locking members 12506 can complimentarily fit within the openings 6607'). The openings 6607' are sized such that a portion of each of the locking members 12506 remain within the openings 12547 defined by the outer shaft assembly 12520 to removably couple the distal shaft 12544 of the outer shaft assembly 12520 to the outer shell 6670' of the spinal implant 6610'.

After the distal shaft 12544 of the outer shaft assembly 12520 is coupled to the outer shell 6670' of the spinal implant 6610', the knob 12515 is rotated, thereby causing the inner shaft assembly 12561 to rotate as indicated by the arrow EE in FIG. 62. The rotation of the inner shaft assembly 12561 within the drive member 12532 movably engages the threaded portions 12571, 12572, thereby causing the drive member 12532 to move within the inner sleeve 12580 as indicated by the arrow FF in FIG. 62. As discussed above, the flatted surface 12576 of the drive member 12532 (see FIG. 60) engages the flatted surface 12583 of the inner sleeve 12580 (see FIG. 59) to prevent the drive member 12532 from rotating within the inner sleeve 12580. Additionally, the protrusion 12582 of the inner sleeve 12580 is received within the slot 12556 defined by the distal shaft 12544 of the outer shaft assembly 12520 to prevent the inner sleeve 12580 from rotating relative to the outer shaft assembly 12520.

When the drive member 12532 moves distally, the engagement surface 12573 of the drive member 12532 engages the inner core 6672' of the spinal implant 6610'. Continued movement of the drive member 12532 as indicated by the arrow FF in FIG. 62 moves the inner core 6672' relative to the proximal portion 6614' of the spinal implant 6610'. In this manner, the spinal implant 6610' can be moved from its expanded configuration to its collapsed configuration while disposed within a patient, for example, due to a prior medical procedure in which the spinal implant 6610' was implanted and moved to its expanded configuration.

After the spinal implant 6610' is removed from and/or repositioned within the body, the deployment tool 12500 can be removed from the spinal implant 6610' by moving the outer sleeve 12590 from its extended position to its retracted position by applying a force sufficient to overcome the biasing force from spring 12509. Because the retention surface 12592 of the outer sleeve 12590 does not engage the locking members 12506 when the outer sleeve 12590 is in its retracted position, the distal shaft 12544 of the outer shaft assembly 12520 can be moved relative to the outer shell 6670' of the spinal implant 6610'. Accordingly, when the distal shaft 12544 of the outer shaft assembly 12520 is disengaged from the outer shell 6670' of the spinal implant 6610', the force from the spring 12507 moves the inner sleeve 12580 from its retracted position to its extended position, thereby retaining the locking members 12506 within the opening 12547 of the distal shaft 12544 of the outer shaft assembly 12520.

Although the connector 12505 is shown and described in FIGS. 56, 61 and 62 as including locking members 12506, in other embodiments, the connector 12505 can include any suitable locking member. For example, in some embodiments, a locking member can be an engaging portion of the type shown and described above with reference to FIGS. 34-36. In other embodiments, a locking member can be a protrusion, a pin and/or a retaining ring.

Similarly, the openings 6607' defined by the outer shell 6670' of the spinal implant 6610' can have any shape suitable to receive and complimentarily fit with the locking members 12506. For example, in some embodiments, the openings 6607' can be elongated about the circumference of the outer shell 6670', which can allow the outer shell 6670' to rotate a predetermined amount with respect to the distal shaft 12544 of the outer shaft assembly 12520 when the distal shaft 12544 of the outer shaft assembly 12520 is coupled to the outer shell 6670. Similarly, in other embodiments, the openings 6607' can be elongated about a longitudinal axis of the outer shell 6670', which can allow the outer shell 6670' to translate a predetermined amount with respect to the distal shaft 12544 of the outer shaft assembly 12520 when the distal shaft 12544 of the outer shaft assembly 12520 is coupled to the outer shell 6670.

Although the angle of the actuation surface 12591 is shown as being approximately 45° with respect to the center line $CL_D$, in other embodiments, the actuation surface 12591 can be disposed at any suitable angle with respect to the center line $CL_D$. For example, in some embodiments, the angle between the actuation surface 12591 and the center line $CL_D$ can be between 30° and 60°. In other embodiments, the actuation surface 12591 can include multiple linear and/or curved portions, each of which is disposed at any suitable angle with respect to the center line $CL_D$. In yet other embodiments, the actuation surface 12591 can be a curved surface.

Although the springs 12507 and 12509 are shown and described above as being coil springs, in other embodiments the inner sleeve 12580 and/or the outer sleeve 12590 can be biased by any suitable biasing member. Such biasing members can include, for example, an elastic member, a magnetic member or the like.

Although the deployment tool 12500 is shown and described above as being used to move a spinal implant from an expanded configuration to a collapsed configuration, the deployment tool 12500 can also be used insert a spinal implant and/or move a spinal implant from a collapsed configuration to an expanded configuration.

Although the deployment tool 12500 is shown and described as including an outer shaft assembly 12520 having a proximal shaft 12543 disposed substantially normal to a distal shaft 12544, in other embodiments, a deployment tool can have any suitable shape. For example, in some embodiments, a deployment tool can have a straight outer shaft. In other embodiments, a deployment tool can have a curved outer shaft. For example, in some embodiments, a deployment tool can have an outer shaft that defines one or more radii of curvature suitable to define and/or proceed along a desired passageway within the body. Such passageways can include, for example, a lateral passageway for accessing adjacent spinous processes, a mid-line passageway for accessing adjacent spinous processes, or the like. Moreover, the shape of the deployment tool can be configured such that the spinal implant is aligned as desired during insertion, repositioning and/or removal.

Although the deployment tool 12500 is shown and described as including a connector 12505 and a drive member 12532 configured to move within a spinal implant, in other embodiments a deployment tool can include only a connector of the types shown and described herein. Similarly, in yet other embodiments a deployment tool can include only a drive member configured to move within a spinal implant.

Figure 63:
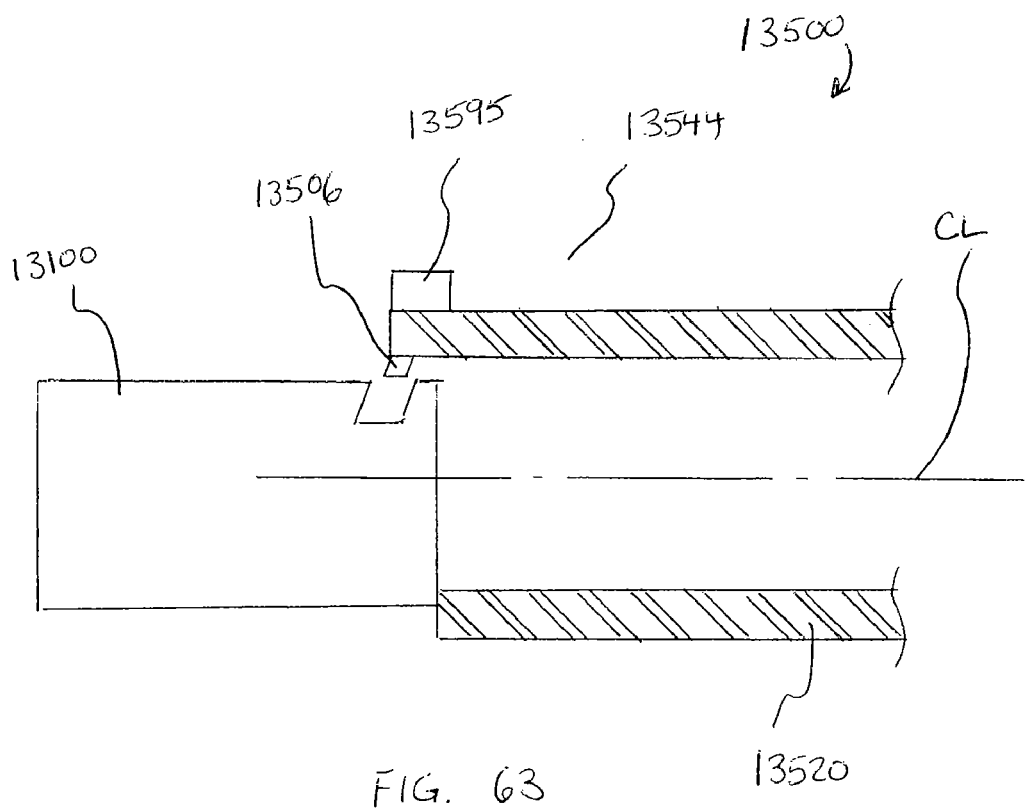
FIGS. 63 and 64 are schematic illustrations of a deployment tool according to an embodiment of the invention, in a first configuration and a second configuration, respectively.
Figure 64:
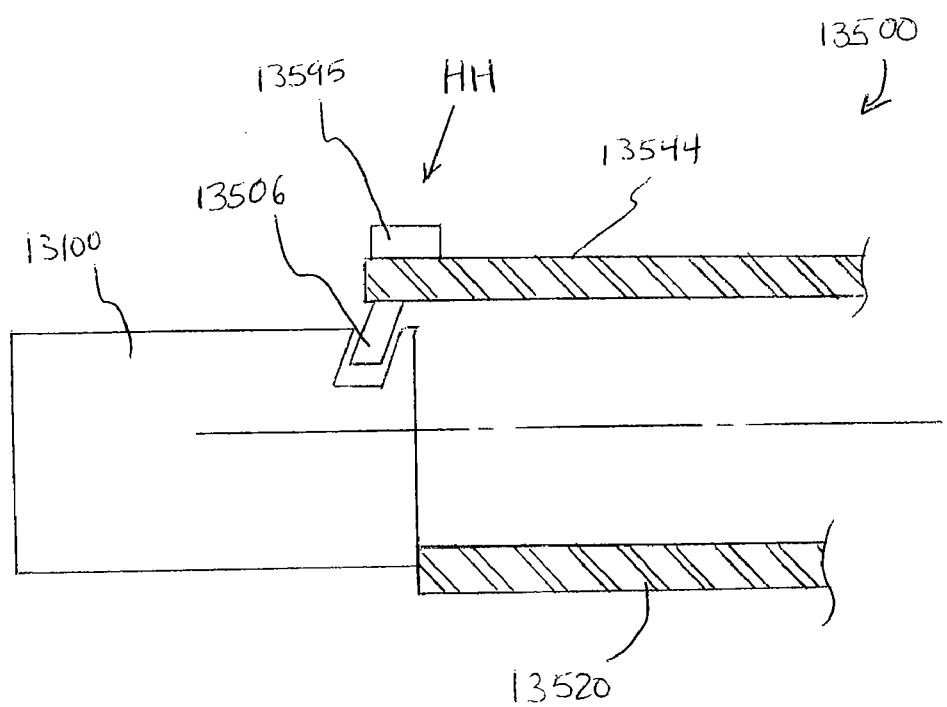

Although the deployment tool 12500 is shown and described above as including a spring-biased actuator (e.g., the outer sleeve 12590) and a locking member 12506 configured to move in a direction substantially perpendicular to the center line $CL_D$, in other embodiments, a deployment tool can include any suitable actuator and/or a locking member configured to move in any suitable direction. For example, FIGS. 63 and 64 are schematic illustrations of a deployment tool 13500 according to an embodiment of the invention. The deployment tool 13500 includes an elongate member 13520, a locking member 13506 and an actuator 13595. The elongate member 13520 has a distal end portion 13544 and defines a center line CL. The elongate member 13520, which can be, for example, a shaft of any type shown and described above, is configured to engage a spinal implant 13100. The locking member 13506 is disposed at the distal end portion 13544 of the elongate member 13520 and can be moved relative to the elongate member 13520 between a first configuration (FIG. 63) and second configuration (FIG. 64), as shown by arrow HH in FIG. 64, when the distal end portion 13544 of the elongate member 13520 engages the spinal implant 13100. The locking member 13506 can be moved in any suitable direction relative to the center line CL.

When the locking member 13506 is in the first configuration, the distal end portion 13544 of the elongate member 13520 can move relative to the spinal implant 13100. When the locking member 13506 is in the second configuration, the distal end portion 13544 of the elongate member 13520 is coupled to the spinal implant 13100. In this manner, the deployment tool 13500 can maintain its position relative to the spinal implant 13100 such that the spinal implant 13100 can be inserted, removed and/or repositioned within the body by deployment tool 13500.

The actuator 13595 can be any suitable actuator configured to move the locking member 13506 between the first configuration and the second configuration. In some embodiments, for example, the actuator can be a mechanical actuator, a pneumatic actuator, a hydraulic actuator and/or an electronic actuator. Moreover, in some embodiments, the actuator 13595 can be configured to retain the locking member 13506 in the first configuration and/or the second configuration. For example, in some embodiments, the actuator 13595 can be a mechanical actuator similar to the outer sleeve 12590 shown and described above.

Figure 65:
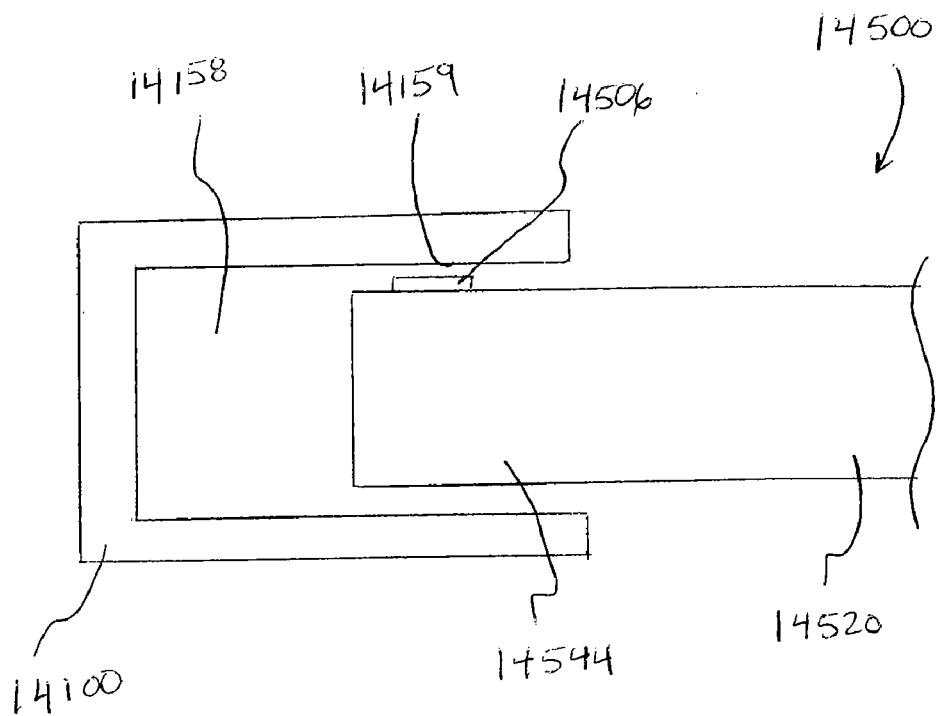
FIGS. 65 and 66 are schematic illustrations of a deployment tool according to an embodiment of the invention, in a first configuration and a second configuration, respectively.
Figure 66:
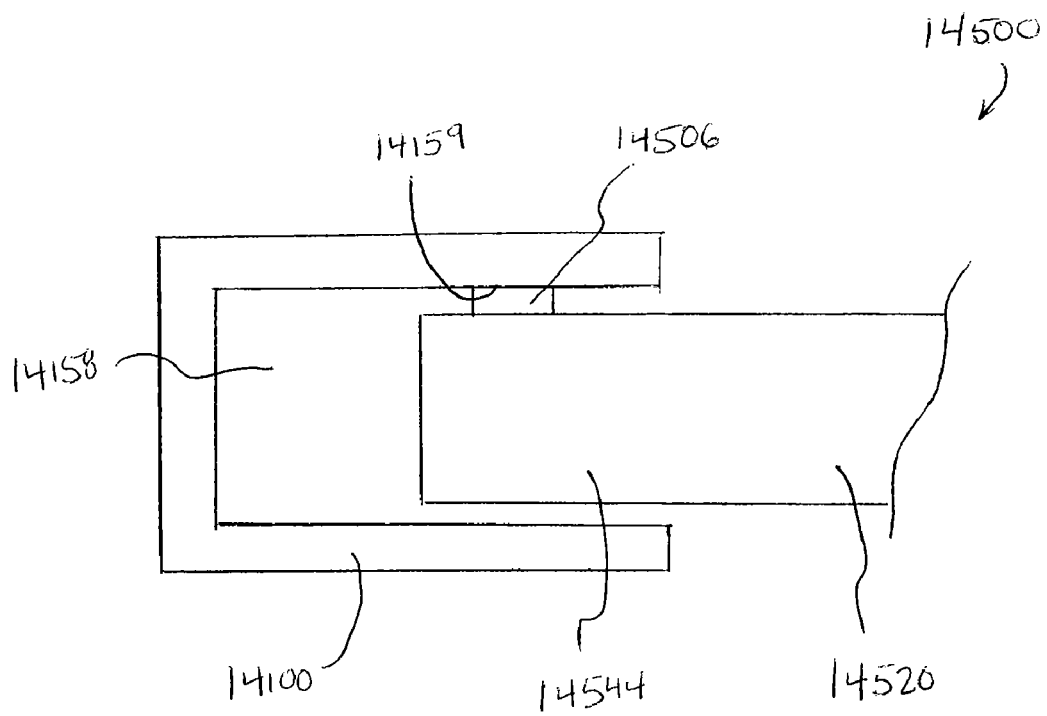

Although the deployment tools are shown and described above as including a locking member configured to move inwardly relative to a spinal implant to engage the spinal implant, in other embodiments, a deployment tool can include a locking member configured to move outwardly relative to a spinal implant. For example, FIGS. 65 and 66 are schematic illustrations of a deployment tool 14500 according to an embodiment of the invention in a first configuration and a second configuration, respectively. The deployment tool 14500 includes an elongate member 14520 and a locking member 14506. The elongate member 14520 has a distal end portion 14544 configured to be removably disposed within an interior portion 14158 defined by a spinal implant 14100.

The locking member 14506 is movable between a first configuration and a second configuration and is configured to releasably couple the distal end portion 14544 of the elongate member 14520 to the spinal implant 14100. When the locking member 14506 is in the first position, the locking member 14506 is disposed substantially within the interior portion 14158 of the spinal implant 14100 such that the elongate member 14520 can move relative to the spinal implant 14100. When the locking member 14506 is in the second position, the locking member 14506 engages a surface 14159 (e.g. a surface defining the interior portion 14158) of the spinal implant 14100 such that the elongate member 14520 cannot substantially move relative to the spinal implant 14100. In this manner, the deployment tool 14500 can maintain its position relative to the spinal implant 14100 such that the spinal implant 14100 can be inserted, removed and/or repositioned within the body by the deployment tool 14500. For example, in some embodiments, the deployment tool can be configured to maintain its position relative to a spinal implant to change the spinal implant from a first configuration (e.g., an expanded configuration) to a second configuration (e.g., a retracted configuration).

Figure 67:
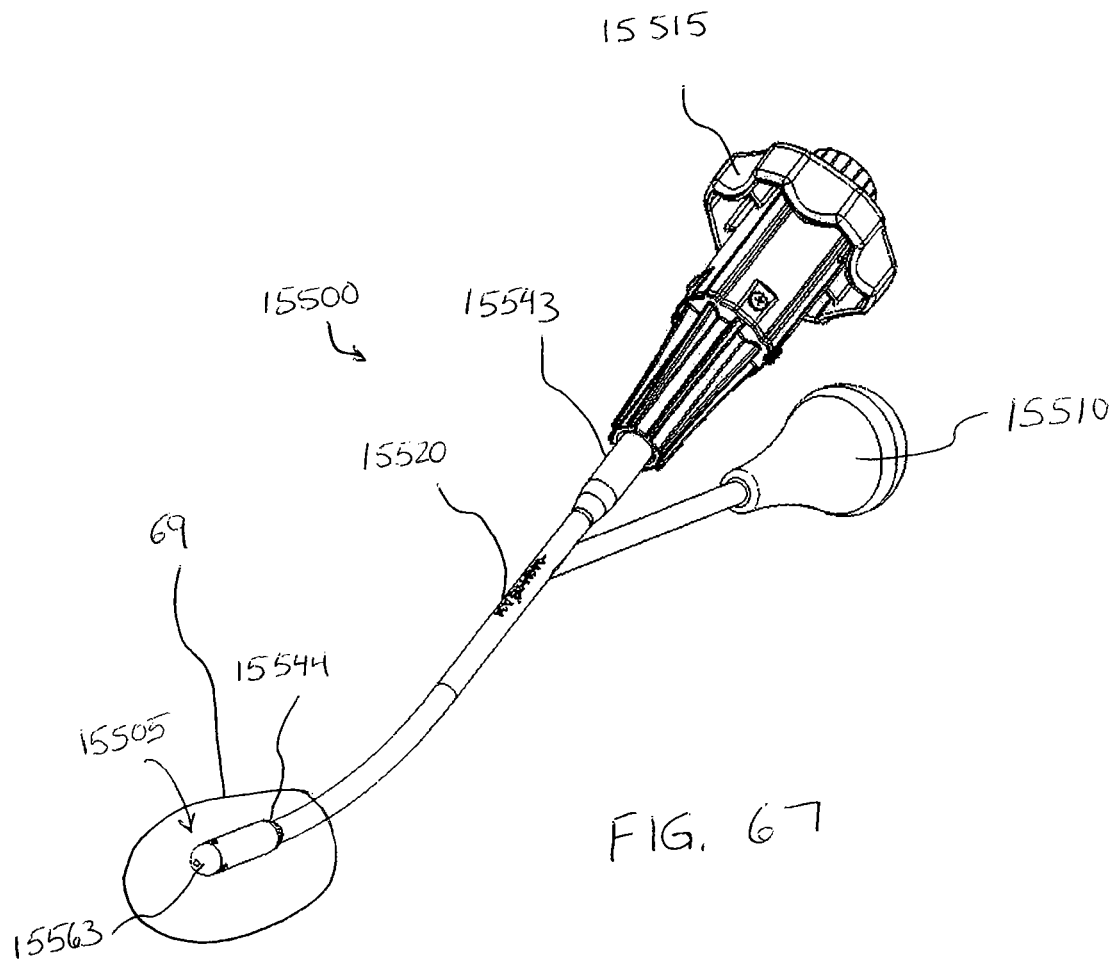
FIG. 67 is a perspective view of a deployment tool according to an embodiment of the invention.

FIG. 67 shows a deployment tool 15500 according to an embodiment of the invention. The deployment tool 15500 includes a curved outer shaft 15520 and a curved inner shaft 15561 (see FIGS. 70-73) movably disposed within the outer shaft 15520. The outer shaft 15520 has a proximal end portion 15543 and a distal end portion 15544. The distal end portion 15544 defines a center line $CL_D$ (see FIG. 70). A knob assembly 15515 similar to the knob assembly 1515 shown and described above with reference to FIGS. 11-14, is disposed at the proximal end portion 15543 of the outer shaft 15520. A connector 15505 is disposed at the distal end portion 15544 of the outer shaft 15520. As described in more detail herein, the connector 15505 is configured to removably connect the distal end portion 15544 of the outer shaft 15520 to a spinal implant 15610 such that the spinal implant 15610 can be moved between an expanded configuration and a collapsed configuration during removal and/or repositioning within the body.

Figure 68:
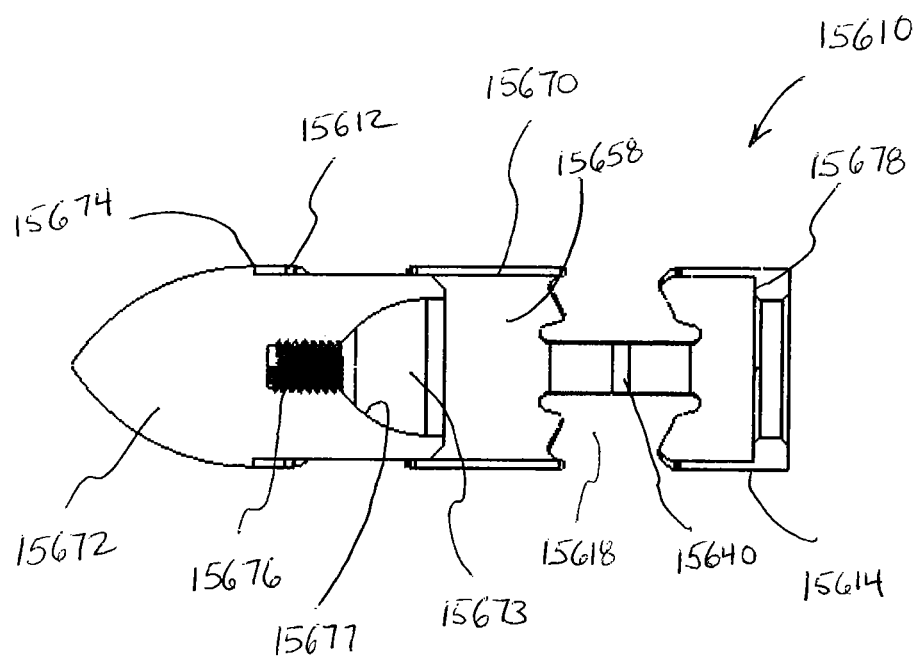
FIG. 68 is a front cross-sectional view of a spinal implant according to an embodiment of the invention.
Figure 69:
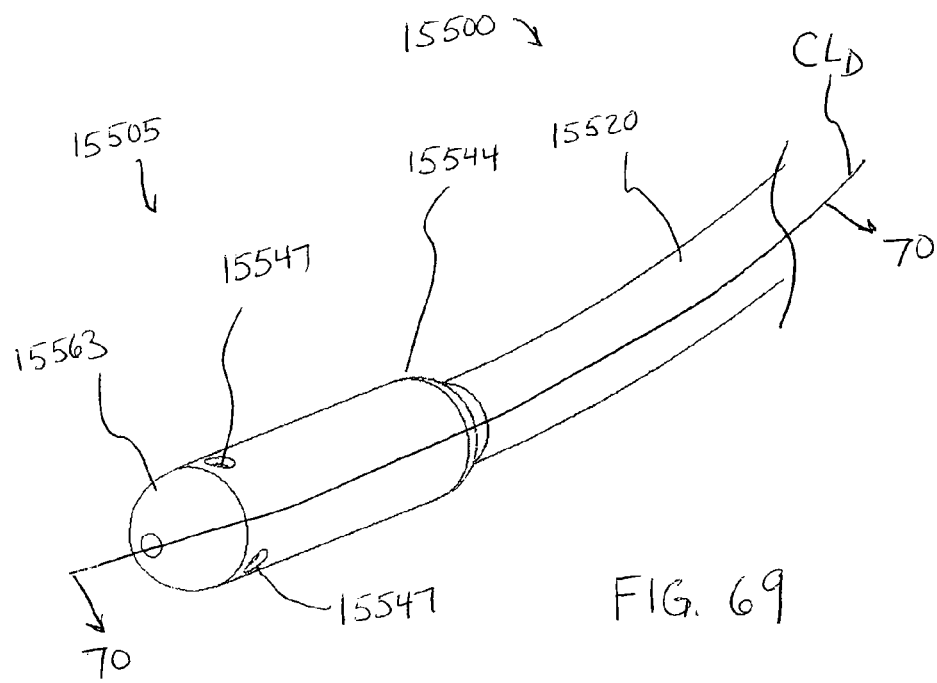
FIG. 69 is a perspective view of a portion of the deployment tool shown as region 69 in FIG. 67.

As shown in FIG. 68, the spinal implant 15610, which is similar to the spinal implants 6610 and 6610' shown and described above, includes an outer shell 15670 having a distal portion 15612 and a proximal portion 15614. The outer shell 15670 defines a series of openings 15618 and has multiple expandable portions 15640 that form extensions 15642 that extend outwardly from the outer shell 15670 (with respect to center line $CL_D$) when the implant 15610 is in the expanded configuration (see FIG. 71). The outer shell 15670 also defines an interior portion 15658 and a shoulder surface 15678 within the interior portion 15658

The spinal implant 15610 includes an inner core 15672 disposed within the interior portion 15658 defined by outer shell 15670. The inner core 15672 is fixedly coupled to the distal portion 15612 of the outer shell 15670 at an attachment joint 15674. The inner core 15672 can be fixedly coupled to the outer shell 15670 by any suitable means, such as, for example, a weld, an adhesive bond, an interference fit or the like. The proximal portion of the inner core 15672 defines an opening 15673 having a threaded portion 15676 and defines surface 15677. The threaded portion 15676 can be configured, for example, to be coupled to a corresponding threaded portion an expansion device, such as expansion device 7500 shown and described above (e.g., see FIGS. 24-31).

Figure 70:
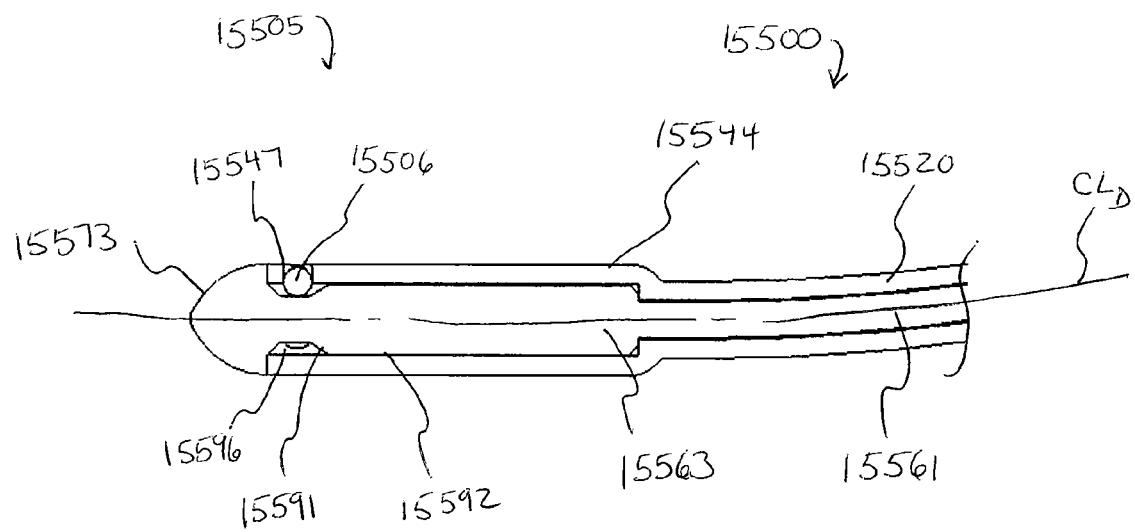
FIG. 70 is a front cross-sectional view of the portion of the deployment tool shown in FIG. 69 taken along line 70-70 in FIG. 69.

Turning to FIG. 70, the connector 15505 includes three locking members 15506 (only one shown in FIG. 70). A portion of each locking member 15506 is disposed within a respective opening 15547 defined by the distal end portion 15544 of the outer shaft 15520. As described herein, the locking members 15506 are configured to move within the openings 15547 in directions substantially perpendicular to the center line $CL_D$ of the distal end portion 15544 of the outer shaft 15520 such that the deployment tool 15500 can be removably coupled to the spinal implant 15610.

Figure 71:
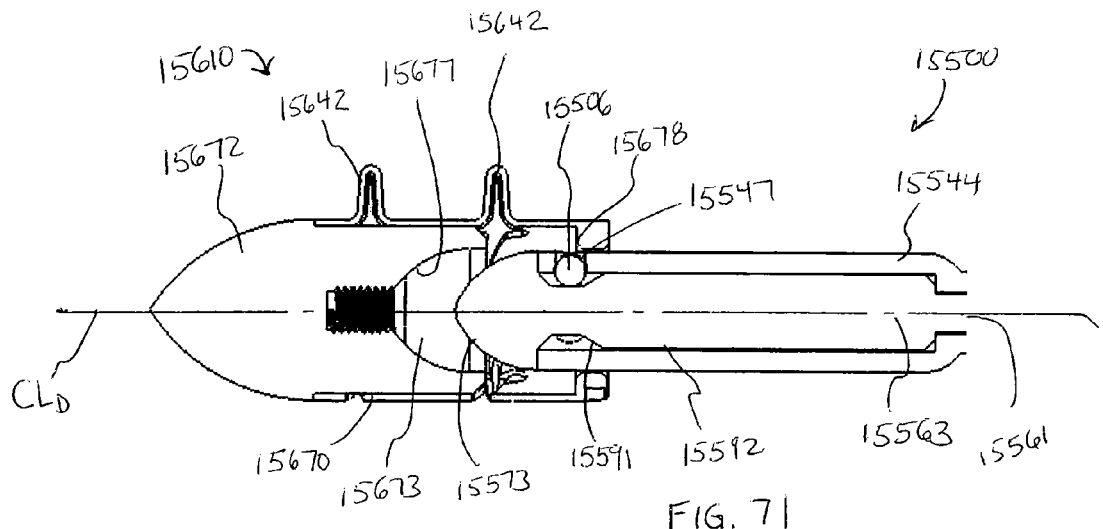
FIGS. 71-73 are a front cross-sectional views of the portion of the deployment tool shown in FIG. 69 and the spinal implant shown in FIG. 68 in a first configuration, a second configuration and a third configuration, respectively.
Figure 72:
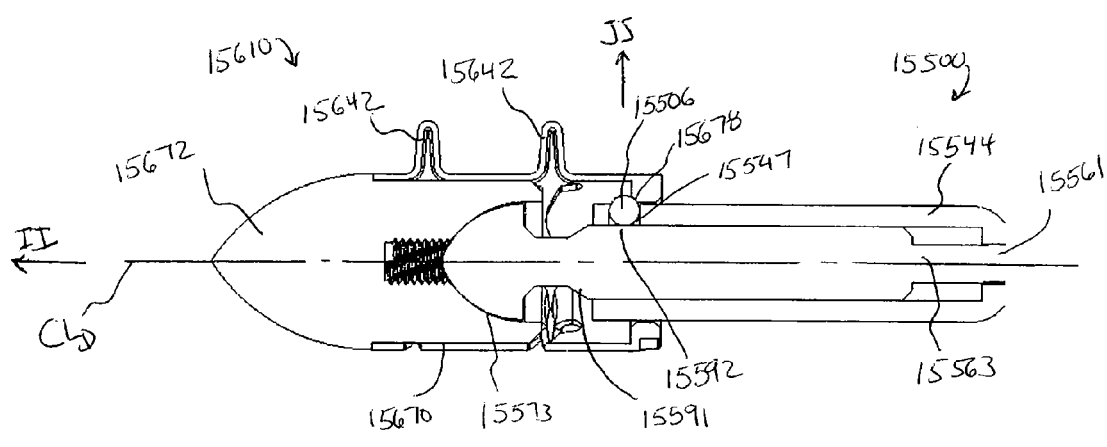
Figure 73:
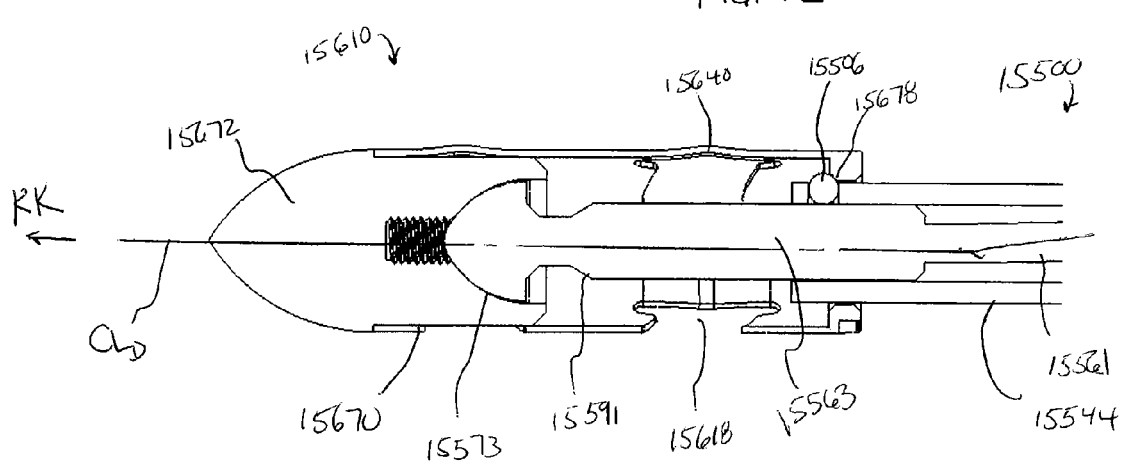

The inner shaft 15561 is slidably disposable within the outer shaft 15520 between a retracted position (see FIGS. 70 and 71) and at least one expanded position (see e.g., FIGS. 72 and 73). A distal end portion 15563 of the inner shaft 15561 includes an actuation surface 15591 that defines a recess 15596 within which a portion of each locking member 15506 can be received when the inner shaft 15561 is in the retracted position. The actuation surface 15591 is at an acute angle with respect to the center line $CL_D$. The distal end portion 15563 of the inner shaft 15561 also includes a retention surface 15592. The retention surface 12592 is substantially parallel to the center line $CL_D$.

When the inner shaft 15561 is in the retracted configuration, the actuation surface 15591 engages and/or is adjacent the locking members 15506. When the inner shaft 15561 moves from the retracted position to the extended position, as indicated by the arrow II in FIG. 72, the force moving the inner shaft 15561 is transmitted via the actuation surface 15591 to the locking members 15506. Because the actuation surface 15591 is at an acute angle with respect to the center line $CL_D$ (e.g., the direction of motion of the inner shaft 15561), a component of the force transmitted via the actuation surface 15591 to the locking members 15506 has an outward direction that is substantially normal to the center line $CL_D$. In this manner, inner shaft 15561 actuates the locking members 15506 outwardly in a direction that is substantially normal to the center line $CL_D$ when the inner shaft 15561 is moved from its retracted position to its extended position. Said another way, movement of the inner shaft 15561 from its retracted position to its extended position causes the locking members 15506 to translate relative to the outer shaft 15520 in a direction that is substantially normal to the center line $CL_D$.

When the inner shaft 15561 is in the extended position, the retention surface 15592 engages the locking members 15506 to prevent the locking members 15506 from moving inwardly through the opening 15547 (i.e., towards the center line $CL_D$). In this manner, the retention surface 15592 of the inner shaft 15561 retains the locking members 15506 in position against the shoulder surface 15678 of the spinal implant 15610 as shown in FIGS. 72 and 73 and described herein. Conversely, when the inner shaft 15561 is moved from the extended position to the retracted position, the retention surface 15592 is disengaged from the locking members 15506, thus allowing the locking members 15506 to move inwardly through the opening. In this manner, the connector 15505 can be disconnected from the spinal implant 15610.

In some embodiments, the deployment tool 15500 can be used to move the spinal implant 15610 from an expanded configuration (FIG. 71) to a collapsed configuration (FIG. 73) to facilitate removal and/or repositioning of the spinal implant 15610. First, the distal end portion 15544 of the outer shaft 15520 is inserted into the body and disposed within the outer shell 15670 of the spinal implant 15610, as shown in FIG. 71. When the distal end portion 15544 of the outer shaft 15520 is disposed within the outer shell 15670, the inner shaft 15561 is moved from its retracted position to a first extended position, as shown by the arrow II in FIG. 72. The inner shaft 15561 can be moved, for example, by rotating the knob assembly 15515 as described above.

As described above, when the inner shaft 15561 is moved distally relative to the outer shaft 15520, the actuation surface 15591 urges the locking members 15506 outwardly through the openings 15547 in a direction substantially perpendicular to the center line $CL_D$ and into engagement with the shoulder surface 15678 (e.g. see the arrow JJ in FIG. 72 for the locking member 15506 shown in FIG. 72). In this manner, the outer shell 15670 of the spinal implant 15610 is prevented from moving distally relative to the deployment tool 15500.

After the distal end portion 15544 of the outer shaft 15520 is coupled to the outer shell 15670 of the spinal implant 15610, the inner shaft 15561 is moved from the first expanded position to a second expanded position, as shown by the arrow KK in FIG. 73. Accordingly, an engagement surface 15573 of the inner shaft 15561 engages the surface 15677 of the inner core 15672 and moves the inner core 15672 distally relative to the proximal portion 15614 of the spinal implant 15610. In this manner, the spinal implant 15610 can be moved from its expanded configuration to its collapsed configuration.

Although the locking members 15506 are shown and described above as engaging the shoulder surface 15678 to prevent distal motion of the outer shell 15670 of the spinal implant 15610 relative to the deployment tool 15500, in some embodiments, the locking members 15506 can complimentarily fit with an opening defined by a surface of an interior portion of a spinal implant. For example, in some embodiments, an interior surface of an implant can define a notch, groove, or other recessed region within which the locking members can be disposed.

Figure 74:
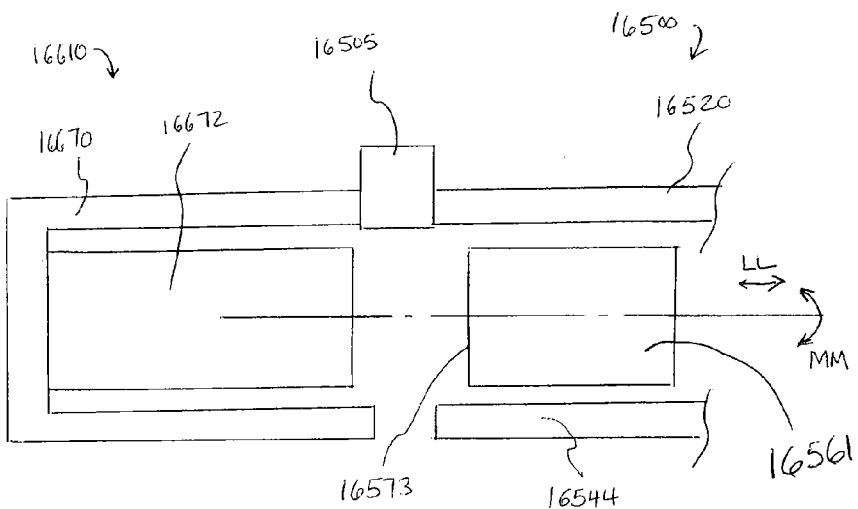
FIG. 74 is a schematic illustration of a deployment tool according to an embodiment of the invention.

As described above, in some embodiments, a deployment tool can include any suitable type of connector to releasably couple the deployment tool to a spinal implant and any suitable type of drive member configured to move within the spinal implant. For example, FIG. 74 is a schematic illustration of a deployment tool 16500 according to an embodiment of the invention. The deployment tool 16500 includes a first elongate member 16520, a second elongate member 16561 and a connector 16505. The connector 16505 is disposed at a distal end portion 16544 first of the first elongate member 16520. The connector 16505, which can be any suitable connector as shown and described herein, is configured to releasably connect the distal end portion 16544 of the first elongate member 16520 to an outer member 16670 of a spinal implant 16610. For example, in some embodiments, the connector 16505 can be configured to prevent the spinal implant 16610 from moving distally relative to the first elongate member 16520. Similarly, in some embodiments, the connector 16505 can be configured to prevent the spinal implant 16610 from rotating relative to the first elongate member 16520.

The second elongate member 16561 is movably disposed within the distal end portion 16544 of the first elongate member 16520. In some embodiments, for example, the second elongate member 16561 can translate within the distal end portion 16544 of the first elongate member 16520, as shown by the arrow LL in FIG. 74. In other embodiments, the second elongate member 16561 can rotate within the distal end portion 16544 of the first elongate member 16520, as shown by the arrow MM in FIG. 74. In yet other embodiments, the second elongate member 16561 can translate and rotate within the distal end portion 16544 of the first elongate member 16520.

The second elongate member 16561 includes a surface 16573 configured to engage an inner member 16672 of the spinal implant 16610. In this manner, as described above, the deployment tool 16500 can change the configuration of the spinal implant 16610 to facilitate the insertion, removal and/ or repositioning of the spinal implant 16610 within the body.

FIGS. 75-81 show a deployment tool 17500 according to an embodiment of the invention. The deployment tool 17500 includes an outer shaft 17520 and an inner shaft 17561 movably disposed within the outer shaft 17520. The deployment tool 17500 also includes a connector 17505 disposed at a distal end portion 17544 of the outer shaft 17520. As described in more detail herein, the connector 17505 is configured to releasably connect the distal end portion 17544 of the outer shaft 17520 to a spinal implant 17610 (not shown in FIGS. 75 and 76) such that the spinal implant 17610 can be moved between an expanded configuration and a collapsed configuration during removal and/or repositioning within the body.

Figure 75:
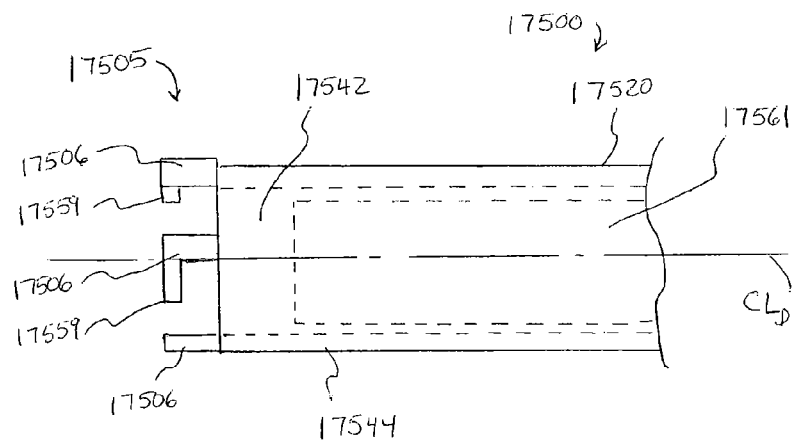
FIG. 75 is a front view of a deployment tool according to an embodiment of the invention.
Figure 76:
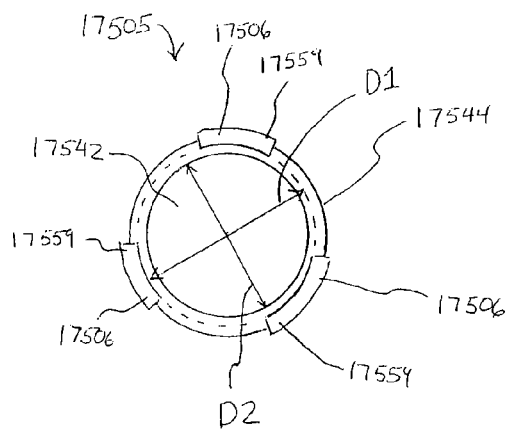
FIG. 76 is a side view of the deployment tool shown in FIG. 75.
Figure 77:
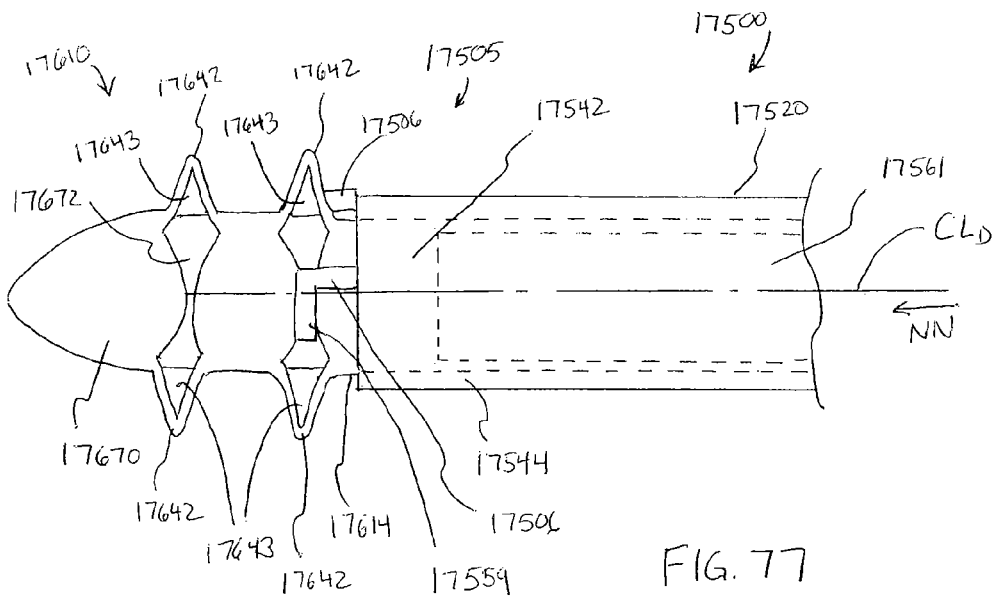
FIGS. 77 and 80 are a front view of the deployment tool shown in FIG. 75 in a first configuration and a second configuration, respectively.

The connector 17505 includes three tines 17506 that extend longitudinally from the distal end portion 17544 of the outer shaft 17520. As shown in FIGS. 75 and 76, the tines 17506 are L-shaped and terminate in end portions 17559 that are substantially normal to a center line $CL_D$ of the distal end portion 17544 of the outer shaft 17520. As shown in FIG. 76 (the outer shaft 17520 is shown without the inner shaft 17561 for clarity), the tines 17506 define a diameter D1 that is no less than a diameter D2 of the receiving area 17542 defined by the connector 17505 and/or the outer shaft 17520. In this manner, the spinal implant 17610 can be received within the receiving are 17542 without being obstructed by the tines 17506.

In some embodiments, the deployment tool 17500 can be used to move the spinal implant 17610 from an expanded configuration (FIG. 80) to a collapsed configuration (FIG. 81) to facilitate removal and/or repositioning of the spinal implant 17610. First, the distal end portion 17544 of the outer shaft 17520 is inserted into the body and disposed about the spinal implant 17610 such that a proximal portion 17614 of an outer shell 17670 of the spinal implant 17610 is received within the receiving area 17542, as shown by the arrow NN in FIG. 77. The connector 17505 is then positioned such that the end portions 17559 of the tines 17506, at least in part, are disposed within and aligned with the openings 17643 formed by the retention members 17642 of the spinal implant 176100. In some embodiments, the surface defining the receiving area 17542 can include a protrusion to limit the range of travel of the spinal implant 17610 within the receiving area 17542 to ensure that the tines 17506 are aligned with the openings 17643.

Figure 78:
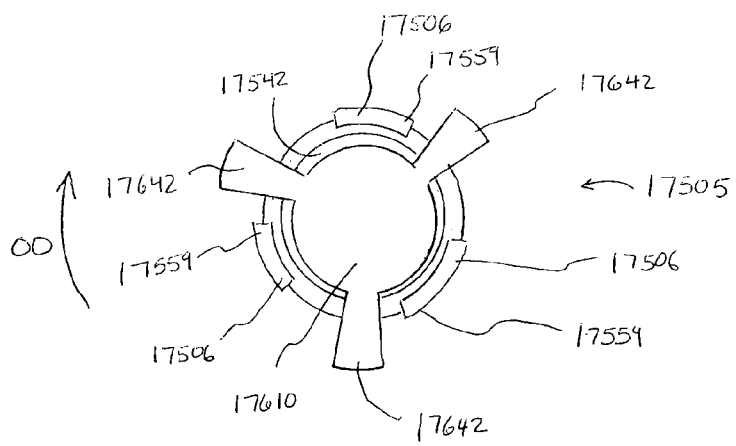
FIGS. 78 and 79 are side views of the deployment tool shown in FIG. 75 in a first configuration and a second configuration, respectively.
Figure 79:
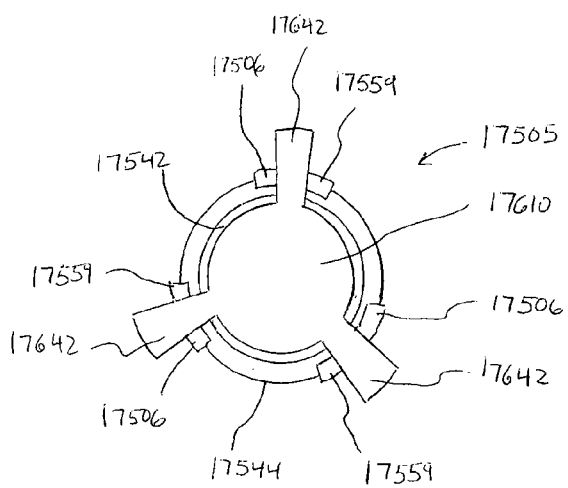
Figure 80:
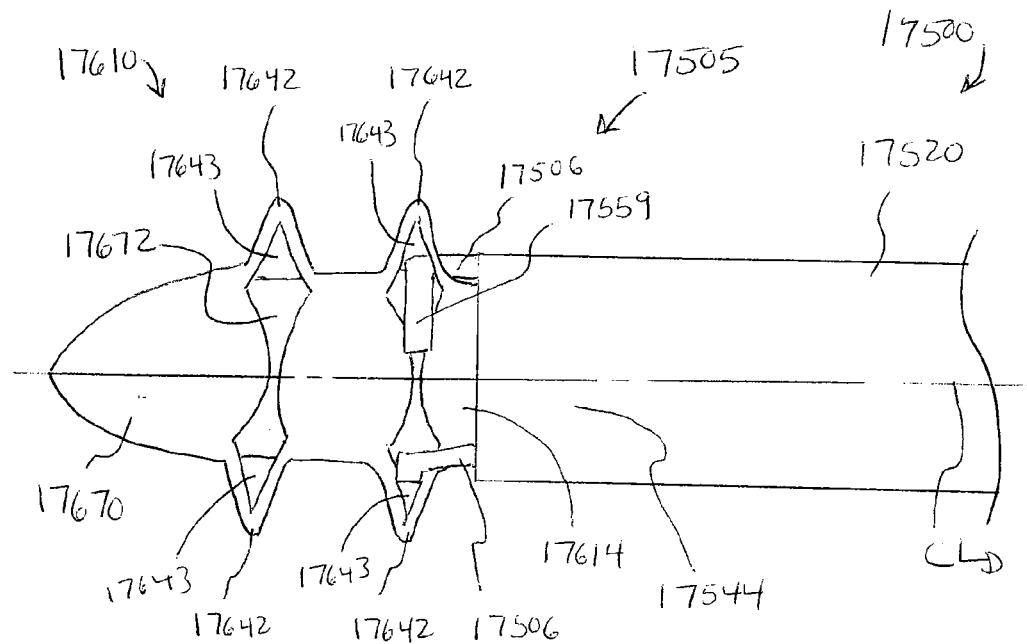

When the distal end portion 17544 of the outer shaft 17520 is disposed about the spinal implant 17610, the connector 17505 is rotated about the center line $CL_D$ of the distal end portion 17544 of the outer shaft 17520, as shown by the arrow OO in FIG. 78. In this manner, the end portions 17559 of the tines 17506 are received within the openings 17643 formed by the retention members 17642 of the spinal implant 176100 to releasably couple the distal end portion 17544 of the outer shaft 17520 to the outer shell 17670 of the spinal implant 17610.

The connector 17505 can be rotated about the center line $CL_D$ in any suitable manner. For example, the connector 17505 can be fixedly coupled to the outer shaft 17520 and the connector 17505 can be rotated by rotating the outer shaft 17520. In such an embodiment, the connector 17505 can be monolithically formed with the outer shaft 17520. In other embodiments, however, the connector can be rotatably coupled to the distal end of the outer shaft. In such embodiments, for example, the connector can be rotated relative to the outer shaft by an actuator disposed at the distal end portion of the outer shaft, as described above. In other embodiments, the connector can be rotated by rotating a knob assembly disposed at a proximal end portion of the outer shaft, as shown and described above.

Figure 81:
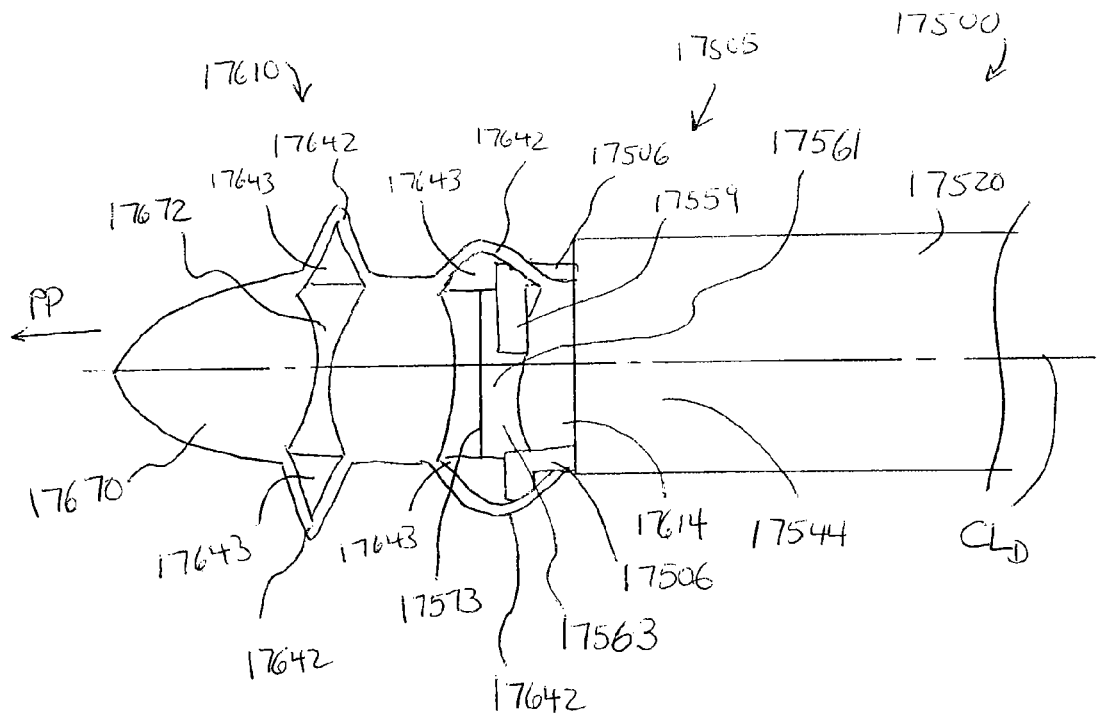
FIG. 81 is a front view of the deployment tool shown in FIG. 75 in a third configuration.

The inner shaft 17561 is then moved within the outer shaft 17520 between a retracted position (see FIG. 77) and at least one expanded position (see FIG. 81). A distal end portion 17563 of the inner shaft 17561 includes an engagement surface 15573 of the inner shaft 17561 engages the inner core 17672 and moves the inner core 17672 distally relative to the proximal portion 17614 of the spinal implant 17610, as shown by the arrow PP in FIG. 81. In this manner, the outer shell 17670 of the spinal implant 17610 is deformed to move the spinal implant 17610 from its expanded configuration to its collapsed configuration.

Although the tines 17506 are shown and described above as engaging a retention member 17642 of a spinal implant 17610, in some embodiments, a connector can include tines configured to engage any portion of a spinal implant, for example, portions of the spinal implant configured to receive the tines of the connector.

Although inner shaft 17561 is shown as translating within the outer shaft 17520, in some embodiments, an inner shaft can rotate within an outer shaft to engage a portion of a spinal implant. For example, in some embodiments, an inner shaft can include a rotating portion and a driver, as shown and described above. Similarly, in some embodiments, an inner shaft can include a threaded portion configured to threadably engage a portion of a spinal implant.

Figure 82:
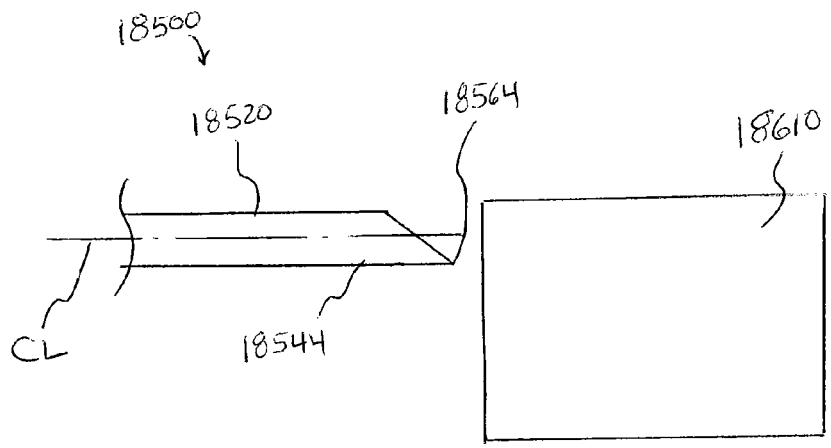
FIGS. 82 and 83 are schematic illustrations of a medical device according to an embodiment of the invention, in a first configuration and a second configuration, respectively.
Figure 83:
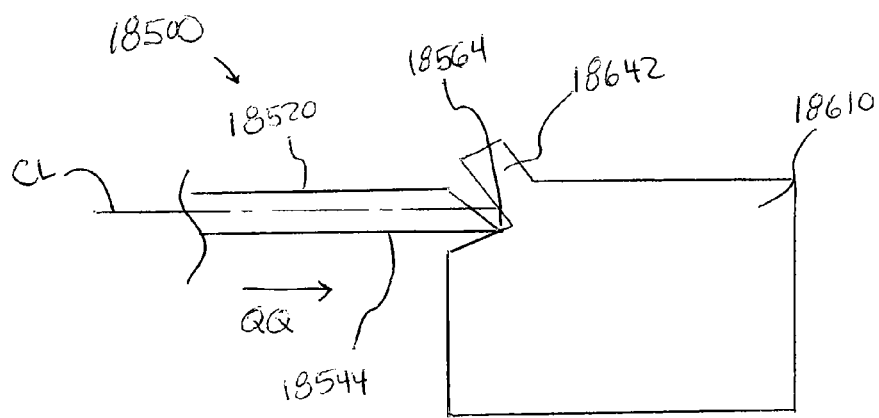

Although the deployment tools shown and described above are configured to move a spinal implant from an expanded configuration to a retracted configuration by plastically deforming a portion of the implant (e.g., a retention member), in some embodiments, a deployment tool can be configured to move a spinal implant from an expanded configuration to a retracted configuration by cutting a portion of the spinal implant. For example, FIGS. 82 and 83 are front view schematic illustrations of a medical device 18500 according to an embodiment of the invention in a first position and a second position, respectively. The medical device 18500 includes an elongate member 18520 having a distal end portion 18544 and defining a center line CL. A cutting edge 18564 is disposed at the distal end portion 18544 of the elongate member 18520. When the elongate member 18520 moves relative to a spinal implant 18610, as shown by the arrow QQ in FIG. 83, the cutting edge 18564 cuts a portion 18642 of the spinal implant 18610. In this manner, the medical device 18500 can move the spinal implant 18610 between a first configuration and a second configuration to facilitate insertion, removal and/or repositioning the spinal implant within the body.

The spinal implant portion 18642 can be any suitable portion of the spinal implant 18610. For example, in some embodiments, the spinal implant portion 18642 can be a portion of an outer shell of a spinal implant. In other embodiments, the spinal implant portion 18642 can be a portion of an inner core of a spinal implant. In yet other embodiments, the spinal implant portion 18642 can be a retention portion of a spinal implant, such as, for example, an extension portion, a tether, an inflatable retention portion or the like.

Although the elongate member 18520 is shown as moving in a direction parallel to the center line CL, in other embodiments, the elongate member 18520 can move in any suitable direction. Moreover, in some embodiments, the movement of the elongate member 18520 can be translation motion, rotation motion and or reciprocation.

Figure 84:
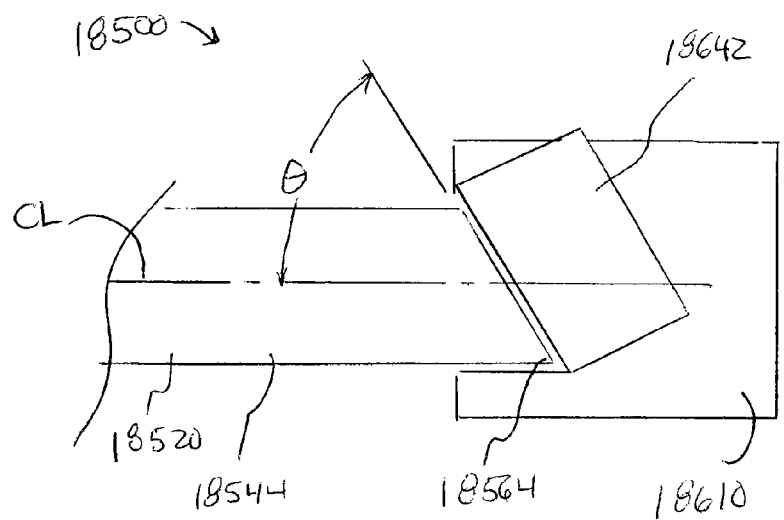
FIG. 84 is a top view schematic illustration of the medical device shown in FIG. 83, in the second configuration.

As shown in FIG. 84, which shows a top view schematic of the elongate member 18520 in the second configuration, the cutting edge 18564 is linear and forms an acute angle E) with the center line CL. In this manner, only a portion of the cutting edge 18564 engages the spinal implant 18610 when the elongate member 18520 moves. Although the cutting edge 18564 is shown as being linear, in other embodiments, a cutting edge can be curved. In yet other embodiments, a cutting edge can be discontinuous. For example, in some embodiments, an elongate member can include multiple cutting edges arranged discontinuously (e.g., a saw-tooth arrangement).

In other embodiments, an elongate member can include multiple cutting edges that are offset from each other longitudinally along the center line CL. For example, in some embodiments an elongate member can include a first cutting edge extending a first longitudinal distance from the distal end portion of the elongate member, a second cutting edge extending a second longitudinal distance from the distal end portion of the elongate member and a third cutting edge extending a third longitudinal distance from the distal end portion of the elongate. In this manner, when the elongate member is moved into engagement with the spinal implant, the first cutting edge can engage a first retention member of the spinal implant before the second cutting edge and the third cutting edge engage the spinal implant.

Figure 85:
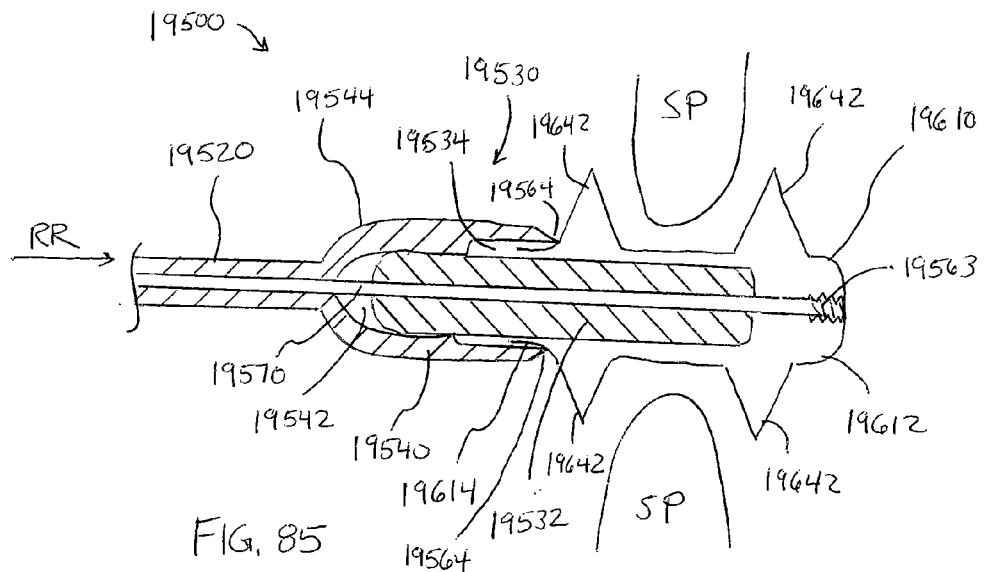
FIGS. 85-87 are cross-sectional front views of a medical device according to an embodiment of the invention, in a first configuration, a second configuration and a third configuration, respectively.
Figure 86:
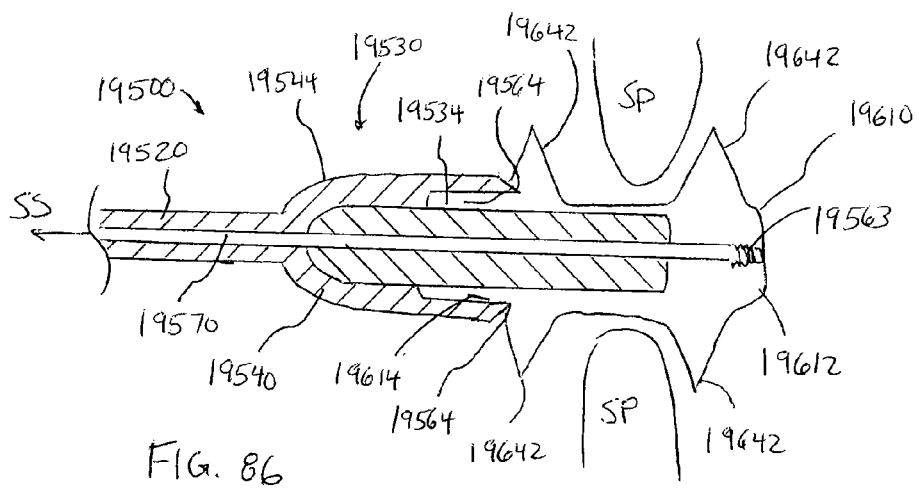
Figure 87:
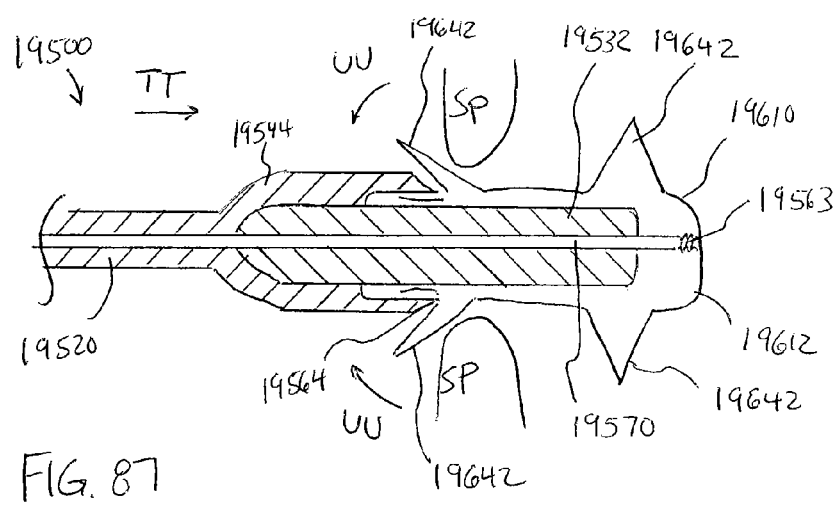

In some embodiments, an elongate member can be configured to receive a portion of a spinal implant such that the cutting edge can be aligned. For example, FIGS. 85-87 show a medical device 19500 according to an embodiment of the invention in a first configuration, a second configuration and a third configuration, respectively. In some embodiments, the medical device 19500 can be used to remove a spinal implant 19610 from between a pair of adjacent spinous processes SP. The medical device 19500 includes a shaft 19520, a rod 19570 disposed within the shaft 19520, and a spacer 19532. The shaft 19520 includes an implant support portion 19530 disposed at a distal end portion 19544 of the shaft 19520. The implant support portion 19530 includes a side wall 19540 that defines a receiving area 19542 configured to receive a portion of the spacer 19532. The side wall 19540 also includes a cutting edge 19564.

First, the distal end portion 19544 of the shaft 19520 is inserted into the body and disposed such that the spacer 19532 is received within the spinal implant 19610, as shown in FIG. 85. The distal end portion 19544 is moved distally as shown by the arrow RR in FIG. 85 such that a proximal end 19614 of the implant is received within a recess 19534 defined by the side wall 19540 and the outer surface of the spacer 19532. In this manner, the spinal implant 19610 is aligned with respect to the medical device 19500.

The distal end 19563 of the rod 19570 is then threadedly coupled to the distal end 19612 of the spinal implant 19610 by rotating the rod 19570 within the shaft 19520. The rod 19570 can be rotated within the shaft 19520 by a knob assembly (not shown in FIGS. 85-87) similar to the knob assembly 1515 shown and described above.

The rod 19570 is then moved proximally within the shaft 19520 as shown by the arrow SS in FIG. 86, which moves the retention members 19642 of the spinal implant 19610 into engagement with the cutting edge 19564 (e.g., two retention members 19642 shown in FIGS. 85-87). As the rod 19570 continues to move proximally, the cutting edges 19564 cut through a portion of the retention members. As shown in FIGS. 85 and 86, when the spacer 19532 engages the side wall 19540 defining the receiving area 19542, the retention member 19642 is prevented from moving relative to the cutting edge 19564. In this manner, the medical device 19500 is configured to cut only a portion of the retention members 19542, therefore preventing the retention members 19542 from being completely severed from the spinal implant 19610.

After the retention members 19642 are cut, the shaft 19520 is moved distally within the body as shown by the arrow TT in FIG. 87. Accordingly, the retention members are bent inwardly towards the implant center line, as shown by the arrow UU in FIG. 87, when the spinal implant 19610 moves past the spinous processes SP.

Figure 88:
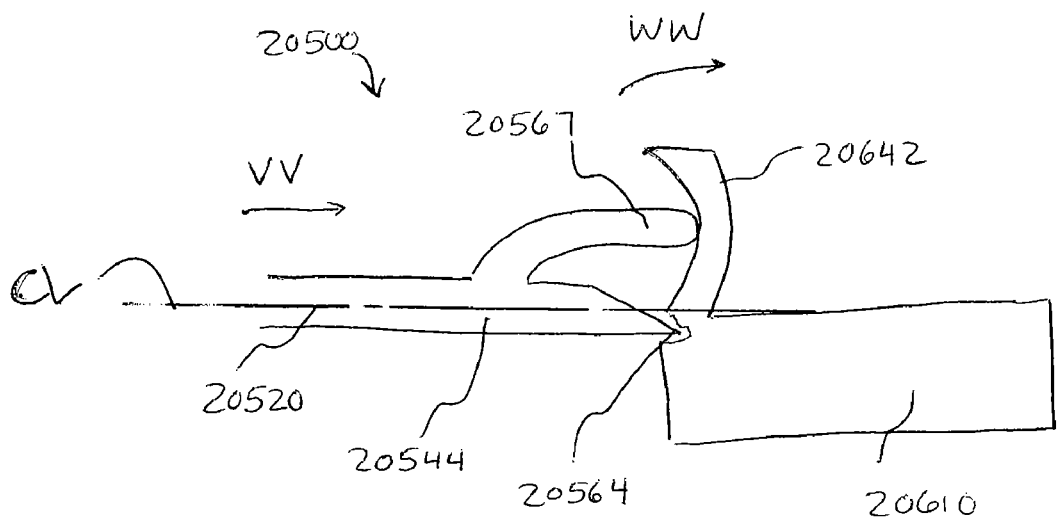
FIG. 88 is a schematic illustration of a medical device according to an embodiment of the invention.

Although not shown in FIGS. 86-88, the rod 19570 can be rotated and/or translated within the shaft 19520 by a knob assembly of the type shown and described above.

Although the cutting edges are shown and described above as being monolithically formed with an elongate member, in other embodiments, a medical device can include a cutting member that is formed separately from the elongate member. In such embodiments, for example, the cutting member can include one or more cutting edges and can be coupled to a distal end portion of the elongate member. In some embodiments, a cutting member can be fixedly coupled to a distal end portion of an elongate member. In other embodiments, a cutting member can be movably coupled to a distal end portion of an elongate. In some embodiments, for example, a medical device can include an elongate member, a cutting member disposed at a distal end portion of the elongate member, and an actuator configured to move the cutting member relative to the elongate member. In such embodiments, the actuator can be an actuator of the types shown and described above, such as, for example, a mechanical actuator (e.g., cable driven, spring driven or the like), a hydraulic actuator, a pneumatic actuator and/or an electronic actuator. In such embodiments, the cutting member can be moved relative to a spinal implant without moving the elongate member.

FIG. 88 is a schematic illustration of a medical device 20500 according to an embodiment of the invention. The medical device 20500 includes an elongate member 20520 having a distal end portion 20544 and defining a center line CL. The distal end portion 20544 of the elongate member 20520 has cutting portion (e.g., a cutting edge) 20564 and a protrusion 20567. When the elongate member 20520 moves relative to a spinal implant 20610, as shown by the arrow VV, the cutting edge 20564 cuts a portion 20642 of the spinal implant 20610. Additionally, after the cutting edge 20564 has cut the portion 20642, the protrusion 20567 moves the portion 20642 relative to the spinal implant 20610, as shown by the arrow WW. In this manner, the cutting edge 20564 and the protrusion 20567 cooperatively cut and bend the portion 20642 of the spinal implant 20610, thereby facilitating the insertion, removal and/or repositioning of the spinal implant 20610 within the body.

Figure 89:
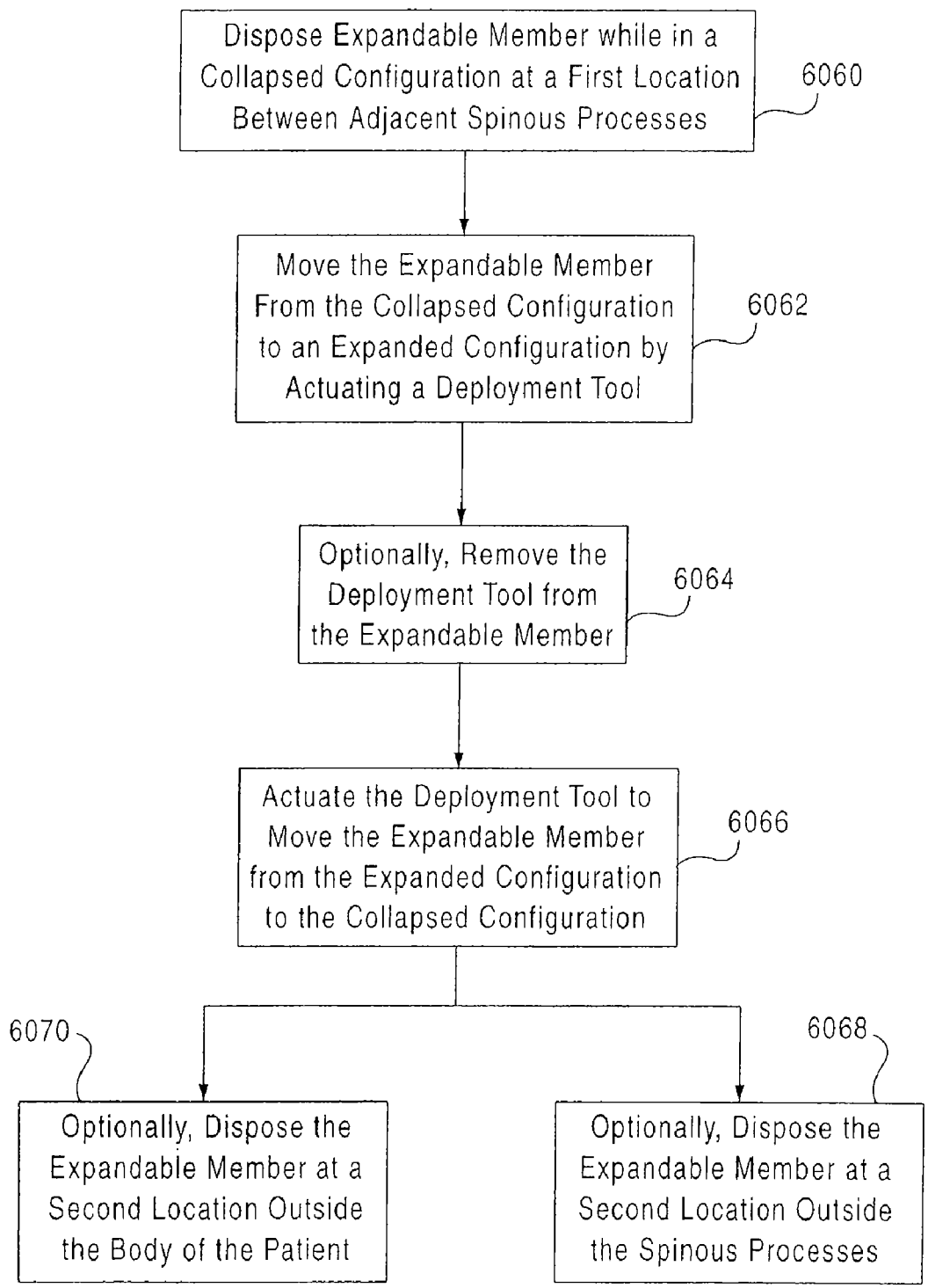
FIG. 89 is a flow chart of a method according to an embodiment of the invention.

FIG. 89 is a flow chart illustrating a method according to an embodiment of the invention. A method includes at 6060, percutaneously disposing an expandable member at a first location between adjacent spinous processes within a body of a patient while the expandable member is in a collapsed configuration. The expandable member is coupled to a deployment tool that includes an engaging portion configured to be received through an opening defined by the expandable member. In other embodiments, the deployment tool can be coupled to the implant after the implant has been disposed between the spinous processes. After the implant has been disposed between the adjacent spinous processes, the expandable member can be moved from the collapsed configuration to an expanded configuration at 6062. To do this, the deployment tool can be actuated while the expandable member is disposed between the adjacent spinous processes such that the engaging portion of the deployment tool imparts a force to a first location on the expandable member and causes the expandable member to move from the collapsed configuration to an expanded configuration. After actuating the deployment tool such that the expandable member is moved from the collapsed configuration to the expanded configuration, the deployment tool can optionally be removed from the expandable member, at 6064. In embodiments where the deployment tool has been removed, the deployment tool can be subsequently reinserted into the expandable member.

At 6066, the deployment tool can be actuated again such that the engaging portion imparts a force to a second location on the expandable member different from the first location on the expandable member, and the implant is moved from the expanded configuration to the collapsed configuration.

After actuating the deployment tool such that the expandable member is moved from the expanded configuration to the collapsed configuration, the expandable member can optionally be disposed at a second location between the adjacent spinous processes different from the first location, at 6068. In some embodiments, after the deployment tool is actuated such that the expandable member is moved from the expanded configuration to the collapsed configuration, the expandable member can optionally be disposed at a second location outside of the body of the patient, at 6070.

Figure 90:
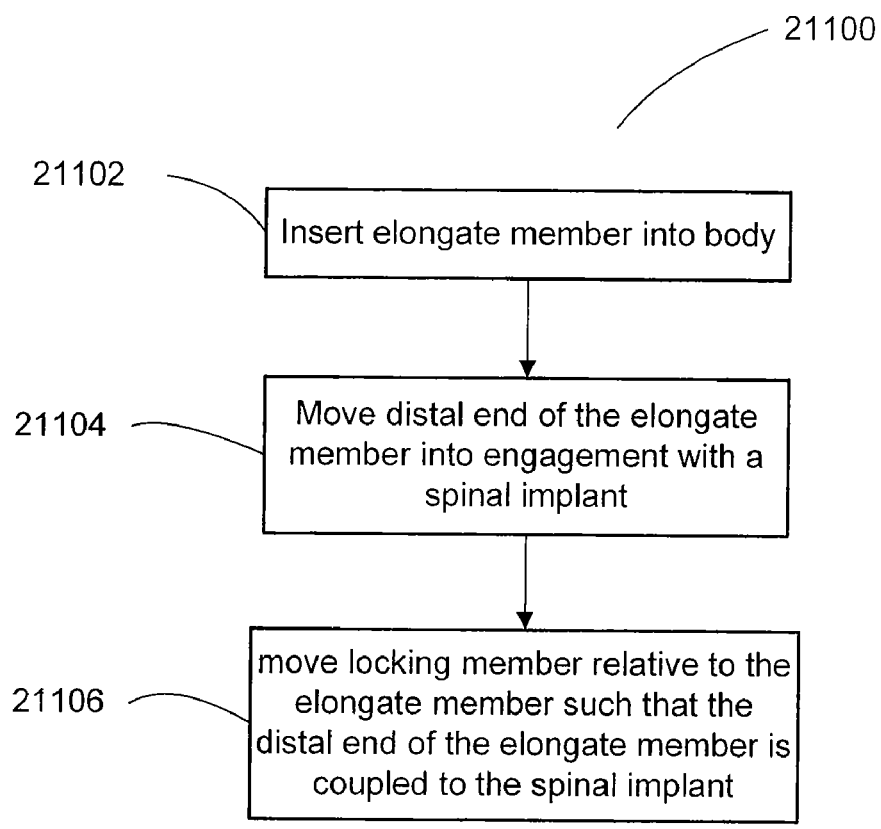
FIG. 90 is a flow chart of a method according to an embodiment of the invention.

FIG. 90 is a flow chart illustrating a method 21100 according to an embodiment of the invention. The method 21100 includes inserting an elongate member of a deployment tool having a centerline into a body, 21102. The elongate member can be any suitable elongate member of the types shown and described above. The elongate member includes a locking member disposed at a distal end portion thereof. In some embodiments, the elongate member can be inserted percutaneously. For example, in some embodiments, the elongate member can be inserted percutaneously via a lateral incision. In other embodiments, the elongate member can be inserted via a mid-line incision.

A distal end portion of the elongate member is then moved into engagement with a spinal implant disposed within the body, 21104. The spinal implant can be any suitable spinal implant as shown and described above. In some embodiments, the distal end portion of elongate member can disposed about a portion of the spinal implant. In other embodiments, the distal end portion of elongate member can received within an interior portion of the spinal implant.

The locking member is then moved relative to the elongate member between a first position and a second position, in a direction substantially perpendicular to a center line of the elongate member, 21106. In this manner, the distal end portion of the elongate member is coupled to the spinal implant. In some embodiments, the locking member can be extended within an opening defined by the elongate member such that a portion of the locking member is outside of the opening. The portion fits within an opening defined by the spinal implant to couple the elongate member to the spinal implant.

In some embodiments, the method 21100 can optionally include moving a sleeve disposed about an outer surface of the elongate member such that the locking member is retained within the opening defined by the spinal implant. In other embodiments, the method 21100 can optionally include moving the elongate member after the elongate member is coupled to the spinal implant such that the spinal implant is removed from the body. In yet other embodiments, the method 21100 can optionally include changing the spinal implant from a first configuration to a second configuration after the elongate member is coupled to the spinal implant, to facilitate removal of the spinal implant from the body and/or repositioning of the spinal implant within the body.

Figure 91:
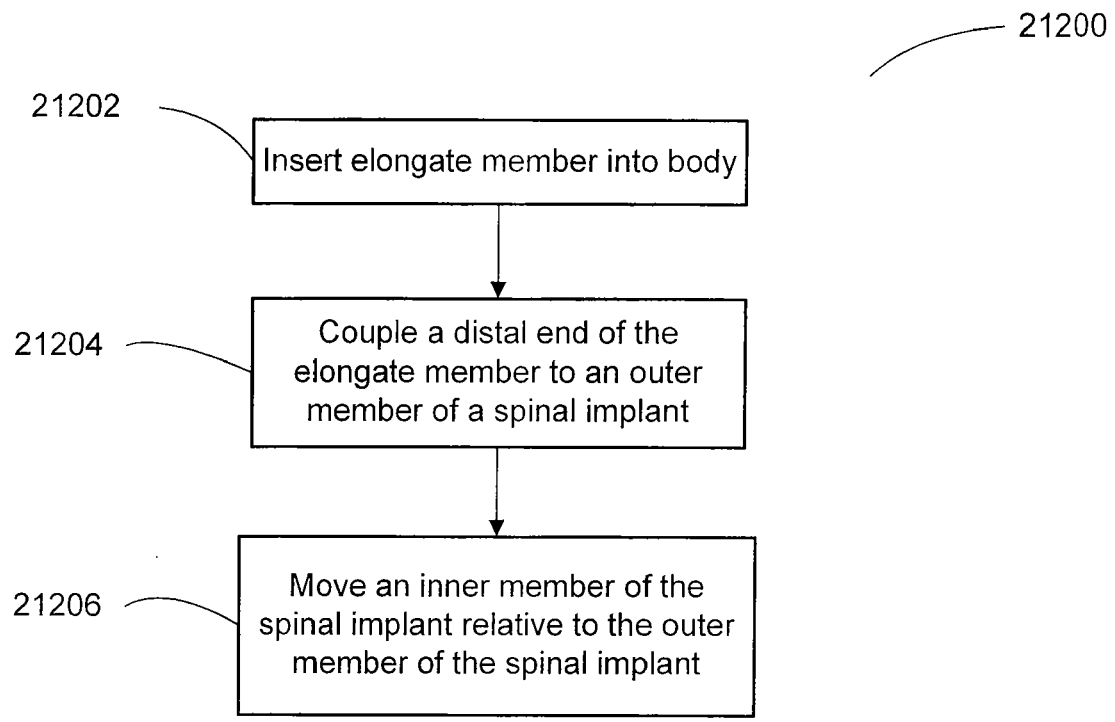
FIG. 91 is a flow chart of a method according to an embodiment of the invention.

FIG. 91 is a flow chart illustrating a method 21200 according to an embodiment of the invention. The method 21200 includes inserting an elongate member of a deployment tool into a body, 21202. The elongate member can be any suitable elongate member of the types shown and described above. In some embodiments, the elongate member can be inserted percutaneously. For example, in some embodiments, the elongate member can be inserted percutaneously via a lateral incision. In other embodiments, the elongate member can be inserted via a mid-line incision.

A distal end portion of the elongate member is then coupled to an outer member of a spinal implant disposed within the body, 22104. The spinal implant can be any suitable spinal implant as shown and described above. In some embodiments, for example, the elongate member includes multiple tines extending from the distal end portion, each of which are configured to be received within an opening defined by the outer portion of the spinal implant. In such embodiments, the distal portion of the elongate member can be coupled to the outer member of the spinal implant by disposing the tines within the openings defined by the outer member of the spinal implant. In some embodiments, the distal portion of the elongate member can be coupled to the outer member of the spinal implant such that the outer member of the implant is prevented from moving distally relative to the first elongate member.

An inner member of the spinal implant is then moved relative to the outer member of the spinal implant after the elongate member is coupled to the outer member of the spinal implant coupling, 21206. In some embodiments, for example, the elongate member can be a first elongate member of the deployment tool and the inner member of the spinal implant can be moved by moving a second elongate member of the deployment tool within the first elongate member. The second elongate member is configured to engage the inner member of the spinal implant such that the inner member of the spinal implant is moved distally relative to the outer member of the spinal implant when the second elongate member is moved within the first elongate member. In this manner, for example, the spinal implant can be plastically deformed and/or moved from a first configuration to a second configuration.

The second elongate member of the deployment tool can be, for example, a drive member, a shaft or a rod of the types shown and described above. The second elongate member can be moved within the first elongate member by any suitable manner. For example, in some embodiments, the second elongate member can be translated and/or rotated within the first elongate member by a knob assembly disposed at a proximal end portion of the first elongate member, as shown and described above.

In some embodiments, the method 21200 can optionally include moving the spinal implant within the body and/or removing the spinal implant from the body after the inner member of the spinal implant has been moved.

Figure 92:
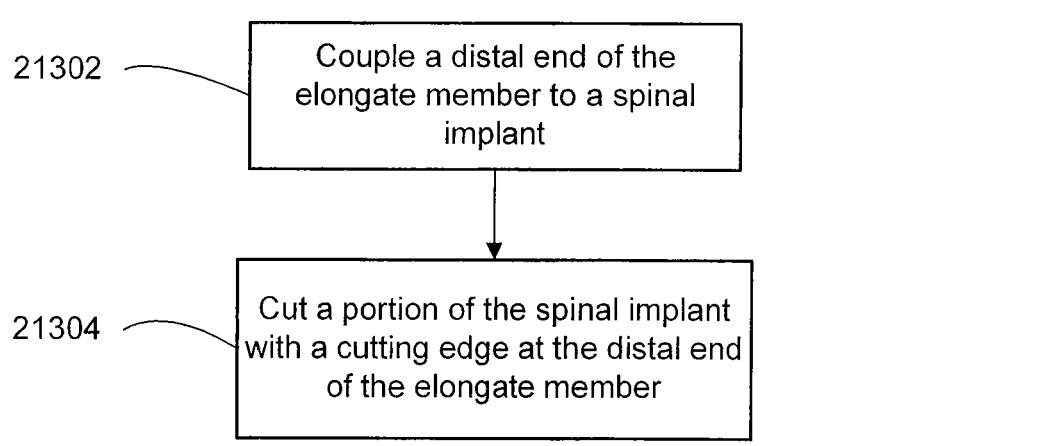
FIG. 92 is a flow chart of a method according to an embodiment of the invention.

FIG. 92 is a flow chart illustrating a method 21300 according to an embodiment of the invention. The method 21300 includes coupling a distal end of an elongate member to a spinal implant within a body, 21302. The elongate member can be any suitable elongate member of the types shown and described above. In some embodiments, the method can optionally include inserting percutaneously the elongate member. For example, in some embodiments, the elongate member can be inserted percutaneously via a lateral incision. In other embodiments, the elongate member can be inserted via a mid-line incision.

In some embodiments, the elongate member is a first elongate member within which a second elongate member is disposed. In such embodiments, the first elongate member can be coupled to the spinal implant by removably coupling the second elongate member to the spinal implant. In some embodiments, for example, the second elongate member can be a threaded rod configured to complimentarily fit within a threaded opening of the spinal implant.

A portion of the spinal implant is then cut with a cutting edge disposed at the distal end portion of the elongate member, 21304. In some embodiments, for example, the cutting edge can be moved relative to the elongate member such that the portion of the spinal implant is cut. In some embodiments, a retention member of the spinal implant can be cut with the cutting edge.

In some embodiments, the elongate member is a first elongate member within which a second elongate member is disposed. In such embodiments, the first elongate member can be coupled to the spinal implant by removably coupling the second elongate member to the spinal implant. Moreover, the cutting edge can be moved relative to the portion of the spinal implant by moving the second elongate member within the first elongate member.

In some embodiments, the method 21300 can optionally include deforming the portion of the spinal implant (either plastically or elastically) after the portion of the spinal implant has been cut. In some embodiments, the method 21300 can optionally include removing the spinal implant from the body after the portion of the spinal implant has been cut.

The various implants and deployment tools described herein can be constructed with various biocompatible materials such as, for example, titanium, titanium alloyed, surgical steel, biocompatible metal alloys, stainless steel, plastic, polyetheretherketone (PEEK), carbon fiber, ultra-high molecular weight (UHMW) polyethylene, biocompatible polymeric materials, etc. The material of a central portion of the implant can have, for example, a compressive strength similar to or higher than that of bone. In one embodiment, the central portion of the implant, which is placed between the two adjacent spinous processes, is configured with a material having an elastic modulus higher than the elastic modulus of the bone, which forms the spinous processes. In another embodiment, the central portion of the implant is configured with a material having a higher elastic modulus than the materials used to configure the distal and proximal portions of the implant. For example, the central portion of the implant may have an elastic modulus higher than bone, while the proximal and distal portions have a lower elastic modulus than bone. In yet another embodiment, where the implant is configured with an outer shell and an inner core. The outer shell can be configured with material having a higher elastic modulus than the inner core (e.g., outer shell is made with titanium alloyed, while the inner core is made with a polymeric material). Alternatively, the outer shell can be configured with a material having a lower elastic modulus than the inner core (e.g., the outer shell is made with a polymeric material while the inner core is made with a titanium alloyed material).

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Thus, the breadth and scope of the invention should not be limited by any of the above-described embodiments, but should be defined only in accordance with the following claims and their equivalents.

While the invention has been particularly shown and described with reference to specific embodiments thereof, it will be understood that various changes in form and details may be made.

For example, although the embodiments above are primarily described as being spinal implants configured to be positioned between adjacent spinous processes, in alternative embodiments, the implants are configured to be positioned adjacent any bone, tissue or other bodily structure where it is desirable to maintain spacing while preventing axial or longitudinal movement of the implant.

Although the medical devices are shown and described as including an implant and/or a deployment tool, in some embodiments a kit can include any number of implants and/or any number of deployment tools as described above. For example, a kit can include an implant and two deployment tools, one deployment tool configured to be used to move the implant from a collapsed configuration to an expanded configuration, and another deployment tool configured to be used to move the implant from the expanded configuration to the collapsed configuration. Alternatively, a kit can include a single deployment tool have multiple engaging portions as described herein, that can be releasably coupled to an elongate member of a deployment tool. For example, one type or style of engaging portion can be used to move the implant from a collapsed configuration to an expanded configuration, and another type or style of engaging portion can be used to move the implant from the expanded configuration to the collapsed configuration. The kit can include engaging portions having one of a variety of different shapes and sizes, such that a user can select a particular engaging portion(s) for use in a particular application.

Similarly, although various embodiments have been described as having particular features and/or combinations of components, other embodiments are possible having a combination of any features and/or components from any of embodiments as discussed above. For example, one such embodiment includes an elongate member having multiple tines extending from a distal end thereof, the tines configured to be received within a portion of a spinal implant, similar to the deployment tool 17500 shown and described above. The embodiment further includes a spring-biased outer sleeve configured to retain the tines within the spinal implant, similar to the sleeves shown in the deployment tool 12500 shown and described above.

Similarly, in some embodiments, a deployment tool, an expansion device and/or an insertion tool can be configured to perform any combination of functions described herein. For example, in some embodiments, a deployment tool, an expansion devices and/or an insertion tool can be configured to insert a spinal implant into a body, move a spinal implant between a retracted configuration and an expanded configuration within a body, reposition a spinal implant within the body and/or remove a spinal implant within the body. In some embodiments, a deployment tool, an expansion device and/or an insertion tool can be configured to perform only a single function, such as, for example, removing a spinal implant from body. In other embodiments, a kit can include a deployment tool, an expansion device and/or an insertion tool along with various implements so that the deployment tool, expansion device and/or insertion tool can be re-configured to perform any combination of functions described herein.

What is claimed is:

1. A method for moving an implant from an expanded configuration to a retracted configuration, comprising:
   coupling a distal end portion of an elongate body to an implant when the implant is already in the expanded configuration and disposed within a patient's body, the distal end portion of the elongate body comprising a cutting edge;

cutting a portion of the implant with the cutting edge to form a cut in the implant;

changing the implant from the expanded configuration to the retracted configuration by deforming the implant proximate the cut.

2. The method of claim 1 wherein the implant is disposed within the body between adjacent spinous processes.

3. The method of claim 1 further comprising inserting percutaneously the elongate member into the body before the coupling.

4. The method of claim 1 wherein:
the elongate body includes first and second elongate members, the second elongate member being disposed within the first elongate member;
the coupling includes removably coupling the second elongate member to the implant.

5. The method of claim 4 wherein an implant support portion is disposed at a distal end of the first elongate member and the second elongate member extends through the first elongate member and the implant support portion and wherein coupling a distal end of the elongate body to the implant includes:
receiving the implant in a recess formed in the implant support portion;
coupling a distal end of the second elongate member to a distal end of the implant.

6. The method of claim 1 wherein:
the elongate body includes first and second elongate members, the second elongate member being disposed within the first elongate member;
the coupling includes removably coupling a distal end portion of the second elongate member to the implant;
the cutting includes moving the second elongate member in a proximal direction within the first elongate member, while the second elongate member is coupled to the implant, such that the cutting edge engages the portion of the implant.

7. The method of claim 6 wherein the cutting includes cutting a portion of a retention member of the implant and wherein changing the implant further comprises moving the implant in a distal direction past the spinous processes such that as the retention member passes the spinous processes, the retention member bends inwardly towards a center line of the implant.

8. The method of claim 1 wherein the cutting includes cutting a retention member of the implant.

9. The method of claim 1 wherein:
the implant includes an outer member having a tubular body and an inner member having a cylindrical body, the inner member being disposed within the tubular body of the outer member;
the cutting includes cutting a portion of the outer member of the implant.

10. The method of claim 1 wherein the cutting includes moving the cutting edge relative to the elongate body such that the portion of the implant is cut.

11. The method of claim 1 further comprising removing the implant from the body after the cutting.

12. The method of claim 1 wherein:
the implant includes an outer member having a tubular body and an inner member having a cylindrical body, the inner member being disposed within the tubular member;
the cutting includes cutting a portion of the inner member of the implant.

\* \* \* \* \*